United States Patent
Schork et al.

(10) Patent No.: US 6,291,182 B1
(45) Date of Patent: Sep. 18, 2001

(54) METHODS, SOFTWARE AND APPARATI FOR IDENTIFYING GENOMIC REGIONS HARBORING A GENE ASSOCIATED WITH A DETECTABLE TRAIT

(75) Inventors: Nicholas J. Schork, Shaker Heights, OH (US); Laurent Essioux, Paris (FR); Annick Cohen-Akenine, Paris (FR); Marta Blumenfeld, Paris (FR); Daniel Cohen, Neuilly-sur-Seine (FR)

(73) Assignee: Genset, Paris (FR)

( * ) Notice: Subject to any disclaimer, the term of this patent is extended or adjusted under 35 U.S.C. 154(b) by 0 days.

(21) Appl. No.: 09/438,016

(22) Filed: Nov. 10, 1999

Related U.S. Application Data

(60) Provisional application No. 60/140,785, filed on Jun. 23, 1999, and provisional application No. 60/107,986, filed on Nov. 10, 1998.

(51) Int. Cl.[7] ............................. C12Q 1/68; G01N 31/00
(52) U.S. Cl. ................................... 435/6; 702/27
(58) Field of Search ..................... 435/6; 530/300, 530/324, 325, 326; 712/200; 702/27

(56) References Cited

U.S. PATENT DOCUMENTS 5,945,522    8/1999   Cohen et al. .

FOREIGN PATENT DOCUMENTS

WO 98/20165   5/1998   (WO) .
WO 99/04038   1/1999   (WO) .
WO 99/32644   7/1999   (WO) .

OTHER PUBLICATIONS

Morell et al.: *Human Molecular Genetics*, "Analysis of short tandem repeat (STR) allele frequency distributions in a Balinese population," (1995) 4: 85–91.
Hawley et al.: *Nucleic Acids Research*, "HAPLO: A Program Using the EM Algorithm to Estimate the Frequencies of Multi–site Haplotypes,"(1995) 18: 6531–6535.
Xiong et al.: *American Journal of Human Genetics*, "Biallelic Markers in Genetics Studies of Human Diseases: Their Power, Accuracy, and Density In Population–based Linkage Analyses," (1997) 61 (Supp): 1759.
van Lieshout et al., "Polymorphic expression of the glutathione S–transferase P1 gene and its susceptibility to Barrett's esophagus and esophageal carcinoma," Cancer Research, 1999, vol. 59, No. 3, pp. 586–589.*
Dempster, A.P., et al., *Maximum Likelihood from Incomplete Data via the EM Algorithm*: Statistical Society Presentation, Harvard University: 39:1–38 (1977).
Drigalenko, et al., *False Discoveries in Genome Scanning*: Genetic Epidemiology: 14:779–784 (1997).
Excoffier, et al., *Maximum–Likelihood Estimation of Molecular Haplotype Frequencies in a Diploid Population*: Mol. Biol. Evol.: 12(5):921–927 (1995).
Excoffier, et al., *Incorporating Genotypes of Relatives into a Test of Linkage Disequilibrium*: Am.J.Hum. Genet.: 62:171–180 (1998).
Ginns, et al., *A genome–wide search for chromosomal loci linked to mental health wellness in relatives at high risk for bipolar affective disorder among the Old Order Amish*: Proc. Natl. Acad. Sci. USA, 95:15531–15536 (1998).
Hawley, et al., *HAPLO: A Program Using the EM Algorithm to Estimate the Frequencies of Multi–site Haplotypes*: The Journal of Heredity: 86(5)409–411 (1995).
Kruglyak, Leonid, *The use of a genetic map of biallelic markers in linkage studies*: Nature Genetics: 17:21–24 (1997).
Schork, et al., *Linkage Disequilibrium mapping for quantitative traits within case/control settings*: American Journal of Human Genetics: 61(4) (1997).
Schweder, et al. *Plots of P–values to evaluate many tests simultaneously*: Biometrika: 69(3):493–502 (1982).
Thomas, et al. *The Problem of Multiple Inference in Studies Designed to Generate Hypotheses*: American Journal of Epidemiology 122(6): 1080–1094 (1985).
Wang, et al., *Toward a third generation genetic map of the human genome based on bi–allelic polymorphisms*: American Journal of Human Genetics 59(4) (1997).

* cited by examiner

*Primary Examiner*—John S. Brusca
*Assistant Examiner*—Young Kim
(74) *Attorney, Agent, or Firm*—Knobbe Martens Olson & Bear, L.L.P.

(57) ABSTRACT

The present invention relates to methods, software, and apparati for determining whether a genomic region harbors a gene associated with a detectable trait. In one embodiment, the present invention relates to a method of confirming that a genomic region harbors a gene associated with a detectable trait comprising the steps of identifying a candidate genomic region suspected of harboring the gene associated with the detectable trait, constructing a trait-associated distribution of association values using the biallelic markers in the candidate genomic region, identifying a plurality of biallelic markers in random genomic regions which are not suspected of harboring the gene associated with the detectable trait, constructing a random distribution of association values using the biallelic markers in the random genomic regions, comparing the trait-associated distribution of association values to the random distribution of association values, and determining whether the trait-associated distribution of association values and the random distribution of association values are significantly different from one another. In other embodiments, the present invention comprises software for performing the above method and devices comprising the software in a retrievable form.

46 Claims, 32 Drawing Sheets

LD IN A RANDOM FRENCH CAUCASIAN POPULATION

- 54 sized « random » BACs covering 8100 kb
- 213 SNP ; 2 to 6 / BAC, mean allele frequency = 0.3
- Order and distance unknown
- For 1 BAC :

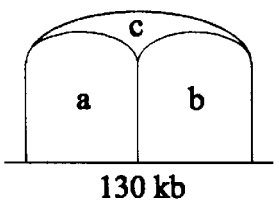

* $\overline{m}$ intermarker distance : 130/3 = 43 kb
  * $\overline{m}$ LD strength estimate : m (a,b,c) = 0.51

- For 54 BACs :

* $\overline{m}$ intermarker distance = 38 kb
  * $\overline{m}$ LD strength estimate = 0.63 ± 0.05
  (324 pairs)

- For 19 unlinked SNPs : m LD strength estimate = 0.12 ± 0.007
  (171 pairs)

FIG. 2C p-VALUE DISTRIBUTION

| # aff | 150 | | | | | |
|---|---|---|---|---|---|---|
| # non aff | 150 | | | | | |
| pAi non aff | 0 | 0.1 | 0.2 | 0.3 | 0.4 | 0.5 |
| Δ pAi 0.05 | 8.77E-05 | 0.06407752 | 0.14252002 | 0.19106311 | 0.21543442 | 0.22009395 |
| Δ pAi 0.1 | 1.91E-08 | 0.00060364 | 0.00467774 | 0.01023571 | 0.01382303 | 0.01382303 |
| Δ pAi 0.15 | 3.06E-12 | 1.3319E-06 | 3.8827E-05 | 0.0001478 | 0.0002343 | 0.00020218 |
| Δ pAi 0.2 | 3.22E-16 | 9.1413E-10 | 9.0305E-08 | 5.733E-07 | 9.6336E-07 | 5.733E-07 |
| Δ pAi 0.25 | 2.08E-20 | 2.2614E-13 | 6.2679E-11 | 5.873E-10 | 8.7113E-10 | 2.5396E-10 |
| Δ pAi 0.3 | 7.82E-25 | 2.152E-17 | 1.3261E-14 | 1.5189E-13 | 1.5189E-13 | 1.3261E-14 |
| Δ pAi 0.35 | 1.62E-29 | 7.9823E-22 | 8.4152E-19 | 9.1669E-18 | 4.2713E-18 | 5.5844E-20 |
| Δ pAi 0.4 | 1.73E-34 | 1.1282E-26 | 1.524E-23 | 1.1488E-22 | 1.524E-23 | 1.1282E-26 |

| # aff | 200 | | | | | |
|---|---|---|---|---|---|---|
| # non aff | 200 | | | | | |
| pAi non aff | 0 | 0.1 | 0.2 | 0.3 | 0.4 | 0.5 |
| Δ pAi 0.05 | 5.92E-06 | 0.03250945 | 0.09039173 | 0.13111935 | 0.15260313 | 0.15678006 |
| Δ pAi 0.1 | 8.65E-11 | 7.4765E-05 | 0.00109084 | 0.00302686 | 0.00447365 | 0.00447365 |
| Δ pAi 0.15 | 8.02E-16 | 2.3653E-08 | 2.0257E-06 | 1.1771E-05 | 2.1573E-05 | 1.7772E-05 |
| Δ pAi 0.2 | 4.18E-21 | 1.5375E-12 | 6.7374E-10 | 7.764E-09 | 1.5417E-08 | 7.764E-09 |
| Δ pAi 0.25 | 1.13E-26 | 2.525E-17 | 4.4025E-14 | 8.5532E-13 | 1.4423E-12 | 2.8149E-13 |
| Δ pAi 0.3 | 1.47E-32 | 1.1488E-22 | 5.8424E-19 | 1.4886E-17 | 1.4886E-17 | 5.8424E-19 |
| Δ pAi 0.35 | 8.62E-39 | 1.4784E-28 | 1.5457E-24 | 3.6958E-23 | 1.3394E-23 | 4.197E-26 |
| Δ pAi 0.4 | 2.09E-45 | 5.2308E-35 | 7.6438E-31 | 1.1224E-29 | 7.6438E-31 | 5.2308E-35 | aff    affected individuals
non aff    non affected individuals
pAi non aff    allele frequency in non affected individuals
Δ pAi    % Difference in allele frequency between affected and non-affected individuals

FIG. 3 (I)

p-VALUE DISTRIBUTION

| # aff | 500 | | | | | |
|---|---|---|---|---|---|---|
| # non aff | 500 | | | | | |
| | pAi non aff | 0 | 0.1 | 0.2 | 0.3 | 0.4 | 0.5 |
| Δ pAi | 0.05 | 8E-13 | 0.00072323 | 0.00741965 | 0.0169842 | 0.02371865 | 0.02516449 |
| Δ pAi | 0.1 | 1.07E-24 | 3.7948E-10 | 2.4176E-07 | 2.7579E-06 | 6.9679E-06 | 6.9679E-06 |
| Δ pAi | 0.15 | 3.81E-37 | 1.0719E-18 | 5.8344E-14 | 1.8601E-11 | 1.111E-11 | 1.1611E-11 |
| Δ pAi | 0.2 | 2.96E-50 | 5.0895E-29 | 1.6881E-22 | 6.9321E-20 | 3.7441E-19 | 6.9321E-20 |
| Δ pAi | 0.25 | 4.27E-64 | 7.2043E-41 | 7.7528E-33 | 1.194E-29 | 4.3462E-29 | 7.6438E-31 |
| Δ pAi | 0.3 | 9.7E-79 | 3.9328E-54 | 6.3017E-45 | 1.9429E-41 | 1.9429E-41 | 6.3017E-45 |
| Δ pAi | 0.35 | 2.91E-94 | 8.8513E-69 | 8.7879E-59 | 2.3478E-55 | 1.8839E-56 | 1.1206E-62 |
| Δ pAi | 0.4 | 9.5E-111 | 7.7199E-85 | 1.8063E-74 | 1.4484E-71 | 1.8063E-74 | 7.7199E-85 |

| # aff | 150 | | | | | |
|---|---|---|---|---|---|---|
| # non aff | 850 | | | | | |
| | pAi non aff | 0 | 0.1 | 0.2 | 0.3 | 0.4 | 0.5 |
| Δ pAi | 0.05 | 2.16E-20 | 0.00994614 | 0.04896055 | 0.08358651 | 0.104177953 | 0.11025423 |
| Δ pAi | 0.1 | 2.01E-39 | 5.571E-07 | 0.00010149 | 0.00058665 | 0.00119145 | 0.00139743 |
| Δ pAi | 0.15 | 1.11E-58 | 2.7555E-13 | 8.462E-09 | 2.9851E-07 | 1.2395E-06 | 1.6229E-06 |
| Δ pAi | 0.2 | 3.27E-78 | 2.1683E-21 | 3.2211E-14 | 1.1049E-11 | 1.111E-10 | 1.5638E-10 |
| Δ pAi | 0.25 | 4.96E-98 | 4.4952E-31 | 6.5226E-21 | 3.1015E-17 | 2.5169E-16 | 1.1763E-15 |
| Δ pAi | 0.3 | 3.7E-118 | 3.6987E-42 | 8.129E-29 | 6.9335E-24 | 5.4331E-22 | 6.5657E-22 |
| Δ pAi | 0.35 | 1.4E-138 | 1.6797E-54 | 7.1058E-38 | 1.2938E-31 | 2.9415E-29 | 2.5869E-29 |
| Δ pAi | 0.4 | 2.4E-159 | 5.4915E-68 | 4.8846E-48 | 2.1003E-40 | 1.3332E-37 | 6.8178E-38 |

\# aff      affected individuals
\# non aff    non affected individuals
pAi non aff   allele frequency in non affected individuals
Δ pAi      % Difference in allele frequency between affected and non-affected individuals

FIG. 3 (II)

p-VALUE DISTRIBUTION

| # aff | 200 | | | | | |
|---|---|---|---|---|---|---|
| # non aff | 500 | | | | | |
| | pAi non aff | 0 | 0.1 | 0.2 | 0.3 | 0.4 | 0.5 |
| Δ pAi | 0.05 | 1.06E-12 | 0.00789803 | 0.03942584 | 0.06867566 | 0.08621572 | 0.09083704 |
| Δ pAi | 0.1 | 3.45E-24 | 4.4217E-07 | 5.6883E-05 | 0.00031976 | 0.0006363 | 0.00070881 |
| Δ pAi | 0.15 | 5.9E-36 | 4.3025E-13 | 3.3635E-09 | 9.2134E-08 | 3.319E-07 | 3.5871E-07 |
| Δ pAi | 0.2 | 4.73E-48 | 1.5566E-20 | 1.0346E-14 | 1.7218E-12 | 1.1512E-11 | 1.0047E-11 |
| Δ pAi | 0.25 | 1.67E-60 | 3.5436E-29 | 2.0473E-21 | 2.2178E-18 | 1.1498E-17 | 1.3524E-17 |
| Δ pAi | 0.3 | 2.46E-73 | 7.2498E-39 | 3.0748E-29 | 2.0601E-25 | 3.4525E-24 | 7.4807E-25 |
| Δ pAi | 0.35 | 1.44E-86 | 1.6945E-49 | 3.9559E-38 | 1.4118E-33 | 2.662E-32 | 1.4118E-33 |
| Δ pAi | 0.4 | 3.2E-100 | 5.3051E-61 | 4.7325E-48 | 7.1282E-43 | 1.0691E-41 | 7.2652E-44 |

| # aff | 500 | | | | | |
|---|---|---|---|---|---|---|
| # non aff | 1000 | | | | | |
| | pAi non aff | 0 | 0.1 | 0.2 | 0.3 | 0.4 | 0.5 |
| Δ pAi | 0.05 | 6.48E-24 | 5.7827E-05 | 0.00172627 | 0.00551541 | 0.00882876 | 0.00978249 |
| Δ pAi | 0.1 | 6.53E-47 | 3.065E-14 | 1.0301E-09 | 4.3205E-08 | 1.8833E-07 | 2.2731E-07 |
| Δ pAi | 0.15 | 1.2E-70 | 2.0716E-27 | 3.7441E-19 | 4.6626E-16 | 6.9719E-15 | 6.9719E-15 |
| Δ pAi | 0.2 | 3.33E-95 | 1.1636E-43 | 1.6614E-31 | 8.5632E-27 | 4.1421E-25 | 1.9885E-25 |
| Δ pAi | 0.25 | 1.2E-120 | 1.7683E-62 | 1.5329E-46 | 3.1722E-40 | 8.6765E-39 | 3.6071E-39 |
| Δ pAi | 0.3 | 5.3E-147 | 1.526E-83 | 4.2697E-64 | 2.5968E-56 | 3.9328E-54 | 2.5968E-56 |
| Δ pAi | 0.35 | 2.4E-174 | 1.184E-106 | 4.5658E-84 | 4.7426E-75 | 4.2624E-73 | 4.0958E-77 |
| Δ pAi | 0.4 | 9.4E-203 | 1.082E-131 | 2.137E-106 | 1.8014E-96 | 3.3252E-95 | 6.725E-102 |

FIG. 3 (III)

aff     affected individuals
non aff     non affected individuals
pAi non aff     allele frequency in non affected individuals
Δ pAi     % Difference in allele frequency between affected and non-affected individuals

APO E REGION HAPLOTYPE FREQUENCY ANALYSIS

| POPULATIONS | | | | | AD CASES (225) | | AD CONTROLS (248) | | |
|---|---|---|---|---|---|---|---|---|---|
| markers | 99-366 | 99-344 | 99-359 | 99-355 | haplotype frequencies | | odds-ratio | P value | |
| p value | 3.01E-01 | 1.11E-01 | 6.63E-01 | 1.38E-01 | cases | controls | | | |
| haplotype 1 | C | G | | | 0.404 | 0.308 | 1.52 | 3.05E-03 | *** |
| haplotype 2 | | G | A | | 0.203 | 0.165 | 1.29 | 1.24E-01 | * |
| haplotype 3 | | | G | G | 0.375 | 0.306 | 1.36 | 2.83E-02 | ** |
| haplotype 4 | C | G | A | A | 0.264 | 0.209 | 1.36 | 5.95E-02 | ** |
| haplotype 5 | | | | A | 0.115 | 0.071 | 1.70 | 1.64E-02 | ** |
| haplotype 6 | C | | | | 0.15 | 0.129 | 1.19 | 3.59E-01 | * |
| haplotype 7 | T | | G | G | 0.225 | 0.122 | 2.09 | 4.76E-05 | ***** |
| haplotype 8 | T | A | G | G | 0.228 | 0.108 | 2.44 | 2.05E-06 | ****** |

FIG. 7

PROSTATE CANCER HAPLOTYPE FREQUENCY ANALYSIS

| characteristics of populations | PROSTATE CANCER CASES (281) | NON-AFFECTED CONTROLS (130) |
|---|---|---|
| | 143 sporadic cases + 138 familial cases | > 65 years PSA<4 |

| markers | 99-123 | 4-26 | 4-14 | 4-77 | 99-217 | 4-67 | 99-213 | 99-221 | 99-135 | haplotype frequencies | | relative risk | pvalue |
|---|---|---|---|---|---|---|---|---|---|---|---|---|---|
| bacs | H0287B09 | B0189E08 | | | | B0463F01 | | | B0725B12 | | | | |
| genes | | | | | | <----PG1----> | | | | | | | |
| p value | 2.00 E-01 | 1.00 E-01 | 1.00 E-01 | 2.00 E-02 | 2.00 E-02 | 6.00 E-04 | 9.00 E-02 | 7.00 E-01 | 2.00 E-01 | cases | controls | | |
| haplotype 8 >304kb< | C | A | C | G | T | T | C | A | A | 0.075 | 0.018 | 4.42 | 9.00E-04 *** |
| haplotype 7 >286kb< | | A | C | G | T | T | C | A | A | 0.095 | 0.016 | 6.46 | 6.00E-05 **** |
| haplotype 6 <186kb> | | A | C | G | T | T | C | A | | 0.116 | 0.019 | 6.78 | 1.00E-05 ***** |
| haplotype 5 <171kb> | | | C | G | T | T | C | A | | 0.117 | 0.013 | 10.06 | 9.00E-07 ****** |
| haplotype 4 <83kb> | | | | G | T | T | C | A | | 0.117 | 0.025 | 5.17 | 2.00E-05 ***** |
| haplotype 3.1 <54kb> | | | | | T | T | C | A | | 0.117 | 0.027 | 4.78 | 2.00E-05 ***** |
| haplotype 3.2 <54kb> | | | | G | | T | C | A | | 0.222 | 0.109 | 2.33 | 4.00E-05 ***** |
| haplotype 2.2 <39kb> | | | | G | | T | C | | | 0.251 | 0.134 | 2.17 | 2.00E-04 **** |
| haplotype 2 <32kb> | | | | | | T | C | | | 0.226 | 0.112 | 2.32 | 1.00E-04 **** |
| haplotype 1.1 <17 kb> | | | | | | T | C | | | 0.256 | 0.146 | 2.01 | 3.00E-04 **** |
| haplotype 1.2 <15 kb> | | | | | | | C | | | 0.233 | 0.129 | 2.05 | 6.00E-04 *** |

FIG. 12

AVERAGE LD PATTERN GENOMIC HETEROGENEITY

| Recombination rate | Lower<br>A | Higher<br>B |
|---|---|---|
| Nb markers | 89 | 69 |
| All SNP | 0.61<br>(749) | 0.42<br>(1190) |
| Rare < 0.2<br>Rare vs rare | 0.75<br>(65) | 0.17<br>(158) |
| Frequent > 0.2<br>Frequent vs frequent | 0.51<br>(410) | 0.49<br>(544) |
| Rare vs frequent | 0.72<br>(274) | 0.41<br>(488) |

FIG. 14

EXONIC/NONEXONIC LD

|  | Nb pairs | Average intermarker distance | Average LD |
|---|---|---|---|
| Exonic SNPs | 36 | 26 kb | 0.65±0.021 |
| Non exonic SNPs | 60 | 36 kb | 0.48±0.018 |
| Exonic/Non exonic | 96 | 32 kb | 0.60±0.015 |

FIG. 15

METHODS, SOFTWARE AND APPARATI FOR IDENTIFYING GENOMIC REGIONS HARBORING A GENE ASSOCIATED WITH A DETECTABLE TRAIT

RELATED APPLICATIONS

This application claims the benefit of U.S. Provisional Application No. 60/107,986, filed Nov. 10, 1998, and U.S. Provisional Application No. 60/140,785, filed Jun. 23, 1999, the entire disclosures of which are incorporated herein by reference.

FIELD OF THE INVENTION

The present invention relates to methods and apparati using nucleic acid markers having a statistical association with a detectable trait to identify one or more genes responsible for the trait or for a predisposition for expressing the trait.

BACKGROUND OF THE INVENTION

Recent advances in genetic engineering and bioinformatics have enabled the manipulation and characterization of large portions of the human genome. While efforts to obtain the full sequence of the human genome are rapidly progressing, there are many practical uses for genetic information which can be implemented with partial knowledge of the sequence of the human genome.

As the full sequence of the human genome is assembled, the partial sequence information available can be used to identify genes responsible for detectable human traits, such as genes associated with human diseases, and to develop diagnostic tests capable of identifying individuals who express a detectable trait as the result of a specific genotype or individuals whose genotype places them at risk of developing a detectable trait at a subsequent time. Each of these applications for partial genomic sequence information is based upon the assembly of genetic and physical maps which order the known genomic sequences along the human chromosomes.

The present invention relates to methods and apparati using nucleic acid markers having a statistical association with a detectable trait to identify one or more genes responsible for the trait or for a predisposition for expressing the trait.

SUMMARY OF THE INVENTION

The present invention relates to methods and apparati for identifying one or more genes associated with a detectable phenotype. As described in more detail below, the present invention involves the use of biallelic markers, which are polymorphic nucleic acid sequences which differ from one another at a single nucleotide. The allelic frequencies of the biallelic markers are compared in nucleic acid samples derived from individuals expressing the detectable trait and individuals who do not express the detectable trait. In this manner, candidate genomic regions suspected of harboring a gene associated with the detectable trait under investigation are identified.

The existence of one or more genes associated with the detectable trait within the candidate region is confirmed by identifying more biallelic markers lying in the candidate region. A first haplotype analysis is performed for each possible combination of groups of biallelic markers within the genomic region suspected of harboring a trait-associated gene. For example, each group may comprise three biallelic markers. For each of the groups of markers, the frequency of each possible haplotype (for groups of three markers there are 8 possible haplotypes) in individuals expressing the trait and individuals who do not express the trait is estimated. For example, the haplotype frequencies may be estimated using the Expectation-Maximization method of Excoffier L and Slatkin M, *Mol. Biol. Evol.* 12:921–927 (1995), the disclosure of which is incorporated herein by reference and which is described in more detail below. In some embodiments, the Expectation-Maximization method may be performed using the EM-HAPLO program (Hawley M E, Pakstis A J & Kidd K K, *Am. J. Phys. Anthropol.* 18:104 (1994), the disclosure of which is incorporated herein by reference). Alternatively, the frequency of each allele of individual biallelic markers may be determined in nucleic acid samples from individuals who express the trait under investigation and control individuals who do not express the trait.

The frequencies of each of the possible haplotypes of the grouped markers (or each allele of individual markers) in individuals expressing the trait and individuals who do not express the trait are compared. For example, the frequencies may be compared by performing a chi-squared analysis. Within each group, the haplotype (or the allele of each individual marker) having the greatest association with the trait is selected. This process is repeated for each group of biallelic markers (or each allele of the individual markers) to generate a distribution of association values, which will be referred to herein as the "candidate region" distribution.

A second haplotype analysis is performed for each possible combination of groups of biallelic markers within random genomic regions. For example, each group may comprise three biallelic markers. For each of the groups of markers, the frequency of each possible haplotype (for groups of three markers there are 8 possible haplotypes) in individuals expressing the trait and individuals who do not express the trait is estimated. For example, the haplotype frequencies may be estimated using the Expectation-Maximization method of Excoffier L and Slatkin M, as described above. In some embodiments, the Expectation-Maximization method may be performed using the EM-HAPLO program as described above. Alternatively, the frequency of each allele of individual biallelic markers may be determined in nucleic acid samples from individuals who express the trait under investigation and control individuals who do not express the trait.

The frequencies of each of the possible haplotypes of the grouped markers (or each allele of individual markers) in individuals expressing the trait and individuals who do not express the trait are compared. For example, the frequencies may be compared by performing a chi-squared analysis. Within each group, the haplotype (or the allele of each individual marker) having the greatest association with the trait is selected. This process is repeated for each group of biallelic markers (or each allele of the individual markers) to generate a distribution of association values, which will be referred to herein as the "random region" distribution.

The "candidate region" distribution and the "random region" distribution of are then compared to one another to determine if there are significant differences between them. For example, the candidate region distribution and the random region distribution can be compared using either the Wilcoxon rank test (Noether, G. E. (1991) Introduction to statistics: "The nonparametric way", Springer-Verlag, New York, Berlin, the disclosure of which is incorporated herein by reference) or the Kolmogorov-Smirnov test (Saporta, G. (1990) "Probalites, analyse des donnees et statistiques" Technip editions, Paris, the disclosure of which is incorporated herein by reference) or both the Wilcoxon rank test and the Kolmogorov-Smirnov test.

If the candidate region distribution and the random region distribution are found to be significantly different, the candidate genomic region is highly likely to contain a gene associated with the detectable trait. Accordingly, the candidate genomic region is evaluated more fully to isolate the trait-associated gene. Alternatively, if the candidate region distribution and the random region distribution are equal using the above analyses, the candidate genomic region is unlikely to contain a gene associated with the detectable trait. Accordingly, no further analysis of the candidate genomic region is performed.

The present invention solves the need for empirical assessments of the statistical significance of the association of biallelic markers with detectable traits. The present invention considers the trait being investigated as well as the populations of individuals utilized to determine the significance of the association. In particular, the present invention allows the reference points (i.e. the controls) for evaluating significance to be derived from the same populations as those used to detect the association between the biallelic markers and the trait. In addition, in some embodiments, the present invention allows all the data available for candidate genomic regions suspected of harboring a gene associated with a detectable trait to be utilized in the determination of whether the candidate region does in fact harbor such a gene. Accordingly, the present invention avoids the risk of failing to detect a significant association between the markers and the trait as a consequence of selecting non-optimal markers or haplotypes for the analysis.

BRIEF DESCRIPTION OF THE DRAWINGS

FIG. 2C shows the results of a linkage disequilibrium analysis in a random French caucasian population.

FIG. 3 shows, for a series of hypothetical sample sizes, the p-value significance obtained in association studies performed using individual markers from the high-density biallelic map, according to various hypotheses regarding the difference of allelic frequencies between the T+ and T− samples.

FIG. 7 is a haplotype analysis using biallelic markers in the Apo E region.

FIG. 12 is a haplotype analysis using the biallelic markers in the genomic region of the gene associated with prostate cancer.

FIG. 14 shows the results of a linkage disequilibrium analysis indicating that rare biallelic markers may be in linkage disequilibrium with more frequent markers or with other rare markers.

FIG. 15 shows the results of a linkage disequilibrium analysis indicating that non-exonic markers may be in linkage disequilibrium with exonic markers or other non-exonic markers.

DETAILED DESCRIPTION OF THE PREFERRED EMBODIMENT

Figure 1:
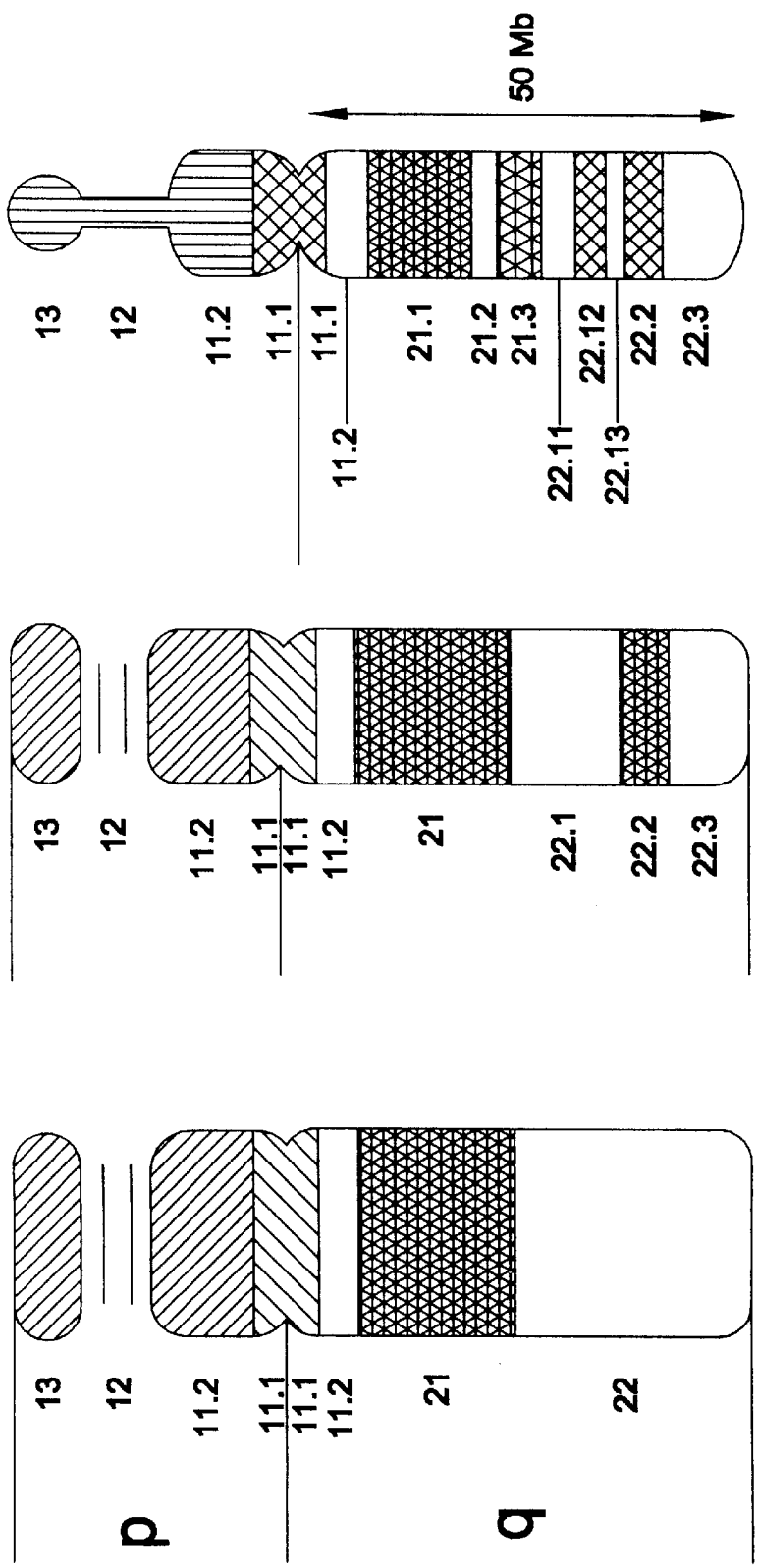
FIG. 1 is a cytogenetic map of chromosome 21.

The human haploid genome contains an estimated 80,000 to 100,000 or more genes scattered on a $3 \times 10^9$ base-long double stranded DNA shared among the 24 chromosomes. Each human being is diploid, i.e. possesses two haploid genomes, one from paternal origin, the other from maternal origin. The sequence of the human genome varies among individuals in a population. About $10^7$ sites scattered along the $3 \times 10^9$ base pairs of DNA are polymorphic, existing in at least two variant forms called alleles. Most of these polymorphic sites are generated by single base substitution mutations and are biallelic. Less than $10^5$ polymorphic sites are due to more complex changes and are very often multi-allelic, i.e. exist in more than two allelic forms. At a given polymorphic site, any individual (diploid), can be either homozygous (twice the same allele) or heterozygous (two different alleles). A given polymorphism or rare mutation can be either neutral (no effect on trait), or functional, i.e. responsible for a particular genetic trait.

Genetic Maps

The first step towards the identification of genes associated with a detectable trait, such as a disease or any other detectable trait, consists in the localization of genomic regions containing trait-causing genes using genetic mapping methods. The preferred traits contemplated within the present invention relate to fields of therapeutic interest; in particular embodiments, they will be disease traits and/or drug response traits, reflecting drug efficacy or toxicity. Traits can either be "binary", e.g. diabetic vs. non-diabetic, or "quantitative", e.g. elevated blood pressure. Individuals affected by a quantitative trait can be classified according to an appropriate scale of trait values, e.g. blood pressure ranges. Each trait value range can then be analyzed as a binary trait. Patients showing a trait value within one such range will be studied in comparison with patients showing a trait value outside of this range. In such a case, genetic analysis methods will be applied to subpopulations of individuals showing trait values within defined ranges.

Genetic mapping involves the analysis of the segregation of polymorphic loci in trait positive and trait negative populations. Polymorphic loci constitute a small fraction of the human genome (less than 1%), compared to the vast majority of human genomic DNA which is identical in sequence among the chromosomes of different individuals. Among all existing human polymorphic loci, genetic markers can be defined as genome-derived polynucleotides which are sufficiently polymorphic to allow a reasonable probability that a randomly selected person will be heterozygous, and thus informative for genetic analysis by methods such as linkage analysis or association studies.

A genetic map consists of a collection of polymorphic markers which have been positioned on the human chromosomes. Genetic maps may be combined with physical maps, collections of ordered overlapping fragments of genomic DNA whose arrangement along the human chromosomes is known. The optimal genetic map should possess the following characteristics:

- the density of the genetic markers scattered along the genome should be sufficient to allow the identification and localization of any trait-related polymorphism,
- each marker should have an adequate level of heterozygosity, so as to be informative in a large percentage of different meioses,
- all markers should be easily typed on a routine basis, at a reasonable expense, and in a reasonable amount of time,
- the entire set of markers per chromosome should be ordered in a highly reliable fashion.

However, while the above maps are optimal, it will be appreciated that individual marker and haplotype association analyses such as those described below may be performed without the necessity of determining the order of biallelic markers derived from a single BAC with respect to one another.

Genetic Maps Based on RFLPs or VNTRs

The analysis of DNA polymorphisms has relied on the following types of polymorphisms. The first generation of genetic markers were restriction fragment length polymorphisms (RFLPs), single nucleotide polymorphisms which occur at restriction sites, thereby modifying the cleavage pattern of the corresponding restriction enzyme. Though the original methods used to type RFLPs were material-, effort- and time-consuming, today these markers can easily be typed by PCR-based technologies. Since they are biallelic markers (they present only two alleles, the restriction site being either present or absent), their maximum heterozygosity is 0.5. The theoretical number of RFLPs distributed along the entire human genome is more than $10^5$, which leads to a potential average inter-marker distance of 30 kilobases. However, in reality, the number of evenly distributed RFLPs which occur at a sufficient frequency in the population to make them useful for tracking of genetic polymorphisms is very limited.

The second generation of genetic markers was VNTRs (Variable Number of Tandem Repeats), which can be categorized as either minisatellites or microsatellites. Minisatellites are tandemly repeated DNA sequences present in units of 5–50 repeats which are distributed along regions of the human chromosomes ranging from 0.1 to 20 kilobases in length. Since they present many possible alleles, their polymorphic informative content is very high. Minisatellites are scored by performing Southern blots to identify the number of tandem repeats present in a nucleic acid sample from the individual being tested. However, there are only $10^4$ potential VNTRs that can be typed by Southern blotting.

Microsatellites (also called simple tandem repeat polymorphisms, or simple sequence length polymorphisms) constitute the most developed category of genetic markers. They include small arrays of tandem repeats of simple sequences (di-,tri-,tetra-nucleotide repeats) which exhibit a high degree of length polymorphism and thus a high level of informativeness. Slightly more than 5,000 microsatellites easily typed by PCR-derived technologies, have been ordered along the human genome (Dib et al., *Nature* 380:152 (1996), the disclosure of which is incorporated herein by reference).

A number of these available microsatellites were used to construct integrated physical and genetic maps containing less than 5,000 markers. For example, CEPH (Chumakov et al., *Nature* 377: 175–298 (1995) and Cohen et al., *Nature* 366: 698–701 (1993), the disclosures of which are incorporated herein by reference), and Whitehead Institute and Genethon (Hudson et al., 1995), constructed genetic and physical maps covering 75% to 95% of the human genome, based on 2500 to 5000 microsatellite markers.

However, the number of easily typed informative markers in these maps was too small for the average distance between informative markers to fulfill the above-listed requirements for genetic maps.

Biallelic Markers

Biallelic markers are genome-derived polynucleotides which exhibit biallelic polymorphism. As used herein, the term biallelic marker means a biallelic single nucleotide polymorphism. As used herein, the term polymorphism may include a single base substitution, insertion, or deletion. By definition, the lowest allele frequency of a biallelic polymorphism is 1% (sequence variants which show allele frequencies below 1% are called rare mutations). There are potentially more than $10^7$ biallelic markers which can easily be typed by routine automated techniques, such as sequence- or hybridization-based techniques, out of which $10^6$ are sufficiently informative for mapping purposes. However, a biallelic marker will show a sufficient degree of informativeness for use in genetic mapping only if the frequency of its less frequent allele is not less than about 10% (i.e. a heterozygosity rate of at least 0.18) (the heterozygosity rate for a biallelic marker is $2\ P_a\ (1-P_a)$, where $P_a$ is the frequency of allele a). Preferably, the frequency of the less frequent allele of the biallelic markers in the present maps is at least 20% (i.e. a heterozygosity rate of at least 0.32). More preferably, the frequency of the less frequent allele of the biallelic markers in the present maps is at least 30% (i.e. its heterozygosity rate is higher than about 0.42).

Initial attempts to construct genetic maps based on non-RFLP biallelic markers have focused on identifying biallelic markers lying within sequence tagged sites (STS), pieces of genomic DNA having a known sequence and averaging about 250 bases in length. More than 30,000 STSs have been identified and ordered along the genome (Hudson et al., *Science* 270:1945–1954 (1995); Schuler et al., *Science* 274:540–546 (1996), the disclosures of which are incorporated herein by reference). For example, the Whitehead Institute and Genethon's integrated map contains 15,086 STSs.

These sequence tagged sites can be screened to identify polymorphisms, preferably Single Nucleotide Polymorphisms (SNPs), more preferably non RFLP biallelic markers therein. Generally polymorphisms are identified by determining the sequence of the STSs in 5 to 10 individuals.

Wang et al. (Cold Spring harbor laboratory: *Abstracts of papers presented on genome Mapping and sequencing* p.17 (May 14–18, 1997), the disclosure of which is incorporated herein by reference) recently announced the identification and mapping of 750 Single Nucleotide Polymorphisms issued from the sequencing of 12,000 STSs from the Whitehead/MIT map, in eight unrelated individuals. The map was assembled using a high throughput system based on the utilization of DNA chip technology available from Affymetrix (Chee et al., *Science* 274:610–614 (1996), the disclosure of which is incorporated herein by reference).

However, according to experimental data and statistical calculations, less than one out of 10 of all STSs mapped today will contain an informative Single Nucleotide Polymorphism. This is primarily due to the short length of existing STSs (usually less than 250 bp). If one assumes $10^6$ informative SNPs spread along the human genome, there would on average be one marker of interest every $3 \times 10^9/10^6$, i.e. every 3,000 bp. The probability that one such marker is present on a 250 bp stretch is thus less than 1/10.

While it could produce a high density map, the STS approach based on currently existing markers does not put any systematic effort into making sure that the markers obtained are optimally distributed throughout the entire genome. Instead, polymorphisms are limited to those locations for which STSs are available.

The even distribution of markers along the chromosomes is critical to the future success of genetic analyses. In particular, a high density map having appropriately spaced markers is essential for conducting association studies on sporadic cases, aiming at identifying genes responsible for detectable traits such as those which are described below.

As will be further explained below, genetic studies have mostly relied in the past on a statistical approach called linkage analysis, which took advantage of microsatellite markers to study their inheritance pattern within families from which a sufficient number of individuals presented the studied trait. Because of intrinsic limitations of linkage analysis, which will be further detailed below, and because these studies necessitate the recruitment of adequate family pedigrees, they are not well suited to the genetic analysis of all traits, particularly those for which only sporadic cases are available (e.g. drug response traits), or those which have a low penetrance within the studied population.

Association studies offer an alternative to linkage analysis. Combined with the use of a high density map of appropriately spaced, sufficiently informative markers, association studies, including linkage disequilibrium-based genome wide association studies, will enable the identification of most genes involved in complex traits.

The present invention relates to a method for generating a high density linkage disequilibrium-based genetic map of the human genome which will allow the identification of sufficiently informative markers spaced at intervals which permit their use in identifying genes responsible for detectable traits using genome-wide association studies and linkage disequilibrium mapping.

Construction of a Physical Map

The first step in constructing a high density genetic map of biallelic markers is the construction of a physical map. Physical maps consist of ordered, overlapping cloned fragments of genomic DNA covering a portion of the genome, preferably covering one or all chromosomes. Obtaining a physical map of the genome entails constructing and ordering a genomic DNA library.

Physical mapping in complex genomes such as the human genome (3,000 Megabases) requires the construction of DNA libraries containing large inserts (on the order of 0.1 to 1 Megabase). It is crucial that such libraries be easy to construct, screen and manipulate, and that the DNA inserts be stable and relatively free of chimerism.

Yeast artificial chromosomes (YACs; Burke et al., *Science* 236:806–812 (1987), the disclosure of which is incorporated herein by reference) have provided an invaluable tool in the analysis of complex genomes since their cloning capacity is extremely high (in the Mb range). YAC libraries containing large DNA inserts (up to 2 Mb) have been used to generate STS-content maps of individual chromosomes or of the entire human genome (Chumakov et al. (1995), supra; Hudson et al. (1995), supra; Cohen et al., *Nature* 366: 698–701 (1993; Chumakov et al., *Nature* 359:380–387 (1992); Gemmill et al., *Nature* 377:299–319 (1995); Doggett et al., *Nature* 377:335–365 (1995); the disclosures of which are incorporated herein by reference).

The present genetic maps may be constructed using currently available YAC genomic libraries such as the CEPH human YAC library as a starting material. (Chumakov et al. (1995), supra). Alternatively, one may construct a YAC genomic library as described in Chumakov et al., 1995, the disclosure of which is incorporated herein by reference, or as described below.

Once a YAC genomic library has been obtained, the genomic DNA fragments therein are ordered. Ordering may be performed directly on the genomic DNA in the YAC library. However, direct ordering of YAC inserts is not preferred because YAC libraries often exhibit a high rate of chimerism (40 to 50% of YAC clones contain fragments from more than one genomic region), often suffer from clonal instability within their genomic DNA inserts, and require tedious procedures to manipulate and isolate the insert DNA. Instead, it is preferable to conduct the mapping and sequencing procedures required for ordering the genomic DNA in a system which enables the stable cloning of large inserts while being easy to manipulate using standard molecular biology techniques.

Accordingly, it is preferable to clone the genomic DNA into bacterial single copy plasmids, for example BACs (Bacterial Artificial Chromosomes), rather than into YACs. Bacterial artificial chromosomes are well suited for use in ordering genomic DNA fragments. BACs provide a low rate of chimerism and fragment rearrangement, together with relative ease of insert isolation. Thus BAC libraries are well suited to integrate genetic, STS and cytogenetic information while providing direct access to stable, readily-sequenceable genomic DNA. An example of bacterial artificial chromosome is the BAC cloning system of Shizuya et al., which is capable of stably propagating and maintaining relatively large genomic DNA fragments (up to 300 kb long) as single-copy plasmids in *E.coli* (Shizuya et al., *Proc. Natl. Acad. Sci. USA* 89:8794–8797 (1992), the disclosure of which is incorporated herein by reference).

Example 1 below describes the construction of a BAC library containing human genomic DNA. It will be appreciated that the source of the genomic DNA, the enzymes used to digest the DNA, the vectors into which the genomic DNA is inserted, and the size of the DNA inserts which are cloned into said vectors need not be identical to those described in Example 1 below. Rather, the genomic DNA may be obtained from any appropriate source, may be digested with any appropriate enzyme, and may be cloned into any suitable vector. Insert size may vary within any range compatible with the cloning system chosen and with the intended purpose of the library being constructed. Typically, using BAC vectors to construct DNA libraries covering the entire human genome, insert size may vary between 50 kb and 300 kb, preferably 100 kb and 200 kb.

To construct a physical map of the genome from genomic DNA libraries, the library clones have to be ordered along the human chromosomes. In a preferred embodiment, a minimal subset of the ordered clones will then be chosen that completely covers the entire genome.

For example the genomic DNA in the inserts of the BAC vectors may be ordered using STS markers whose positions relative to one another and locations along the genome are known using procedures such as those described herein. The STS markers used to order the BAC inserts may be the STS markers contained in the integrated maps described above. Alternatively, the STSs may be STSs which are not contained in any of the physical maps described above. In another embodiment, the STSs may be a combination of STSs included in the physical maps described above and STSs which are not included in the integrated maps described above.

The BAC vectors are screened with STSs until there is at least one positive BAC clone per STS. Preferably, a minimally overlapping set of 10,000 to 30,000 BACs having genomic inserts spanning the entire human genome are identified. More preferably, a minimally overlapping set of 10,000 to 30,000 BACs having genomic inserts of about 100–300 kb in length spanning the entire human genome are identified. In a preferred embodiment, a minimally overlapping set of 10,000 to 30,000 BACs having genomic inserts of about 100–150 kb in length spanning the entire human genome is identified. In a highly preferred embodiment, a minimally overlapping set of 15,000 to 25,000 BACs having genomic inserts of about 100–200 kb in length spanning the entire human genome is identified. Alternatively, a smaller number of BACs spanning a set of chromosomes, a single chromosome, a particular subchromosomal region, or any other desired portion of the genome may be ordered. The BACs may be screened for the presence of STSs as described in Example 2 below.

Alternatively, a YAC (Yeast Artificial Chromosome) library can be used. The very large insert size, of the order of 1 megabase, is the main advantage of the YAC libraries. The library can typically include about 33,000 YAC clones as described in Chumakov et al. (1995, supra). The YAC screening protocol may be the same as the one used for BAC screening.

The known order of the STSs is then used to align the BAC inserts in an ordered array (contig) spanning the whole human genome. If necessary new STSs to be tested can be generated by sequencing the ends of selected BAC inserts. Subchromosomal localization of the BACs can be established and/or verified by fluorescence in situ hybridization (FISH), performed on metaphasic chromosomes as described by Cherif et al. 1990 and in Example 8 below. BAC insert size may be determined by Pulsed Field Gel Electrophoresis after digestion with the restriction enzyme NotI.

Finally, a minimally overlapping set of BAC clones, with known insert size and subchromosomal location, covering the entire genome, a set of chromosomes, a single chromosome, a particular subchromosomal region, or any other desired portion of the genome is selected from the DNA library. For example, the BAC clones may cover at least 100 kb of contiguous genomic DNA, at least 250 kb of contiguous genomic DNA, at least 500 kb of contiguous genomic DNA, at least 2 Mb of contiguous genomic DNA, at least 5 Mb of contiguous genomic DNA, at least 10 Mb of contiguous genomic DNA, or at least 20 Mb of contiguous genomic DNA.

Identification of biallelic markers

In order to generate polymorphisms having the adequate informative content to be used as biallelic markers for genetic mapping, the sequences of random genomic fragments from an appropriate number of unrelated individuals are compared. Genomic sequences to be screened for biallelic markers may be generated by partially sequencing BAC inserts, preferably by sequencing the ends of BAC subclones. Sequencing the ends of an adequate number of BAC subclones derived from a minimally overlapping array of BACs such as those described above will allow the generation of biallelic markers spanning the entire genome, a set of chromosomes, a single chromosome, a particular subchromosomal region, or any other desired portion of the genome with an optimized inter-marker spacing. For example, portions of the BACs in the selected ordered array may be subcloned and sequenced using, for example, the procedures described in Examples 3 and 4 below.

To identify biallelic markers using partial sequence information derived from subclone ends, such as the ends of the BAC subclones prepared above, pairs of primers, each one specifically defining a 500 bp amplification fragment, are designed using the above mentioned partial sequences. The primers used for the genomic amplification of fragments derived from the subclones, such as the BAC subclones prepared above, may be designed using the OSP software (Hillier L. and Green P., *Methods Appl.*, 1:124–8 (1991), the disclosure of which is incorporated herein by reference). The GC content of the amplification primers preferably ranges between 10 and 75%, more preferably between 35 and 60%, and most preferably between 40 and 55%. The length of amplification primers can range from 10 to 100 nucleotides, preferably from 10 to 50, 10 to 30 or more preferably 10 to 20 nucleotides. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures.

All primers may contain, upstream of the specific target bases, a common oligonucleotide tail that serves as a sequencing primer. Those skilled in the art are familiar with primer extensions which can be used for these purposes.

To identify biallelic markers, the sequences corresponding to the partial sequences determined above are determined and compared in a plurality of individuals. The population used to identify biallelic markers having an adequate informative content preferably consists of ca. 100 unrelated individuals from a heterogeneous population. In such procedures, DNA samples, such as peripheral venous blood samples, are obtained from each donor using methods such as those described in Example 5 below. The DNA obtained from peripheral blood as described above is amplified using amplification primers. The sequences of the amplicons are determined and biallelic markers within the amplicons are identified as provided in Example 6 below.

In some embodiments, the biallelic markers are identified by sequencing pools of DNA samples from 100 individuals. The detection limit for the frequency of biallelic polymorphisms detected by sequencing pools of 100 individuals is about 10% for the minor allele, as verified by sequencing pools of known allelic frequencies. However, more than 90% of the biallelic polymorphisms detected by the pooling method have a frequency for the minor allele higher than 25%. Therefore, the biallelic markers selected by this method have a frequency of at least 10% for the minor allele and 90% or less for the major allele, preferably at least 20% for the minor allele and 80% or less for the major allele, more preferably at least 30% for the minor allele and 70% or less for the major allele, thus a heterozygosity rate higher than 0.18, preferably higher than 0.32, more preferably higher than 0.42.

In an initial study to determine the frequency of biallelic markers in the human genome that can be obtained using the above methods the following results were obtained. 300 different amplicons derived from 100 individuals, and covering a total of 150 kb obtained from different genomic regions, were sequenced. A total of 54 biallelic polymorphisms were identified, indicating that there is one biallelic polymorphism with a heterozygosity rate higher than 0.18 (frequency of the minor allele higher than 10%), preferably higher than 0.38 (frequency of the minor allele higher than 25%), every 2.5 to 3 kb. Given that the human genome is about $3.10^6$ kb long, this indicates that, out of the $10^7$ biallelic markers present on the human genome, approximately $10^6$ have adequate heterozygosity rates for genetic mapping purposes.

Using the procedures of Examples 1–6 below, sets containing increasing numbers of biallelic markers may be constructed. For example, in some embodiments, the procedures of Examples 1–6 are used to identify 1 to about 50 biallelic markers. In some embodiments, the procedures of Examples 1–6 are used to identify about 50 to about 200 biallelic markers. In other embodiments, the procedures of Examples 1–6 are used to identify about 200 to about 500 biallelic markers. In some embodiments, the procedures of Examples 1–6 are used to identify about 1,000 biallelic markers. In other embodiments, the procedures of Examples 1–6 are used to identify about 3,000 biallelic markers. In further embodiments, the procedures of Examples 1–6 are used to identify about 5,000 biallelic markers. In another embodiment, the procedures of Examples 1–6 are used to identify about 10,000 biallelic markers, In still another embodiment, the procedures of Examples 1–6 are used to identify about 20,000 biallelic markers. In still another embodiment, the procedures of Examples 1–6 are used to identify about 40,000 biallelic markers. In still another embodiment, the procedures of Examples 1–6 are used to identify about 60,000 biallelic markers. In still another embodiment, the procedures of Examples 1–6 are used to identify about 80,000 biallelic markers. In a still another embodiment, the procedures of Examples 1–6 are used to identify more than 100,000 biallelic markers. In a further embodiment, the procedures of Examples 1–6 are used to identify more than 120,000 biallelic markers.

As discussed above, the ordered nucleic acids, such as the inserts in BAC clones, which contain the biallelic markers of the present invention may span a portion of the genome. For example, the ordered nucleic acids may span at least 100 kb of contiguous genomic DNA, at least 250 kb of contiguous genomic DNA, at least 500 kb of contiguous genomic DNA, at least 2 Mb of contiguous genomic DNA, at least 5 Mb of contiguous genomic DNA, at least 10 Mb of contiguous genomic DNA, or at least 20 Mb of contiguous genomic DNA.

In addition, groups of biallelic markers located in proximity to one another along the genome may be identified within these portions of the genome for use in haplotyping analyses as described below. The biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1 Mb, or more than 1 Mb. It will be appreciated that the ordered DNA fragments containing these groups of biallelic markers need not completely cover the genomic regions of these lengths but may instead be incomplete contigs having one or more gaps therein. As discussed in further detail below, biallelic markers may be used in single maker and haplotype association analyses regardless of the completeness of the corresponding physical contig harboring them.

Ordering of biallelic markers

Biallelic markers can be ordered to determine their positions along chromosomes, preferably subchromosomal regions, most preferably along the above-described minimally overlapping ordered BAC arrays, as follows.

The positions of the biallelic markers along chromosomes may be determined using a variety of methodologies. In one approach, radiation hybrid mapping is used. Radiation hybrid (RH) mapping is a somatic cell genetic approach that can be used for high resolution mapping of the human genome. In ibis approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. (*Genomics* 4:509–517, 1989) and Cox et al., (*Science* 250:245–250, 1990), the entire contents of which are hereby incorporated by reference. The random and independent nature of the subclones permits efficient mapping of any human genome marker. Human DNA isolated from a panel of 80–100 cell lines provides a mapping reagent for ordering biallelic markers. In this approach, the frequency of breakage between markers is used to measure distance, allowing construction of fine resolution maps as has been done for ESTs (Schuler et al., *Science* 274:540–546, 1996, hereby incorporated by reference).

RH mapping has been used to generate a high-resolution whole genome radiation hybrid map of human chromosome 17q22-q25.3 across the genes for growth hormone (GH) and thymidine kinase (TK) (Foster et al., *Genomics* 33:185–192, 1996), the region surrounding the Gorlin syndrome gene (Obemayr et al., *Eur. J. Hum. Genet.* 4:242–245, 1996), 60 loci covering the entire short arm of chromosome 12 (Raeymaekers et al., *Genomics* 29:170–178, 1995), the region of human chromosome 22 containing the neurofibromatosis type 2 locus (Frazer et al., *Genomics* 14:574–584, 1992) and 13 loci on the long arm of chromosome 5 (Warrington et al., *Genomics* 11:701–708, 1991). These publications are all incorporated herein by reference.

Alternatively, PCR based techniques and human-rodent somatic cell hybrids may be used to determine the positions of the biallelic markers on the chromosomes. In such approaches, oligonucleotide primer pairs which are capable of generating amplification products containing the polymorphic bases of the biallelic markers are designed Preferably, the oligonucleotide primers are 18–23 bp in length and are designed for PCR amplification. The creation of PCR primers from known sequences is well known to those with skill in the at. For a review of PCR technology see Erlich, H. A., *PCR Technology; Principles and Applications for DNA Amplification.* 1992. W. H. Freeman and Co., New York, incorporated herein by reference.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 mCi of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the length expected for an amplification product containing the polymorphic base of the biallelic marker, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given biallelic marker. DNA is isolated from the somatic hybrids and used as starting templates for PCR reactions using the primer pairs from the biallelic marker. Only those somatic cell hybrids with chromosomes containing the human sequence corresponding to the biallelic marker will yield an amplified fragment. The biallelic markers are assigned to a chromosome by analysis of the segregation pattern of PCR products from the somatic hybrid DNA templates. The single human chromosome present in all cell hybrids that give rise to an amplified fragment is the chromosome containing that biallelic marker. For a review of techniques and analysis of results from somatic cell gene mapping experiments. (See Ledbetter et al., *Genomics* 6:475–481 (1990), incorporated herein by reference.)

Example 7 below describes a preferred method for positioning of biallelic markers on clones, such as BAC clones, obtained from genomic DNA libraries.

Using such procedures, a number of BAC clones carrying selected biallelic markers can be isolated. The position of these BAC clones on the human genome can be defined by performing STS screening as described in Example 2. Preferably, to decrease the number of STSs to be tested, each BAC can be localized on chromosomal or subchromosomal regions by procedures such as those described in Examples 8 and 9 below. This localization will allow the selection of a subset of STSs corresponding to the identified chromosomal or subchromosomal region. Testing each BAC with such a subset of STSs and taking account of the position and order of the STSs along the genome will allow a refined positioning of the corresponding biallelic marker along the genome.

If the DNA library used to isolate BAC inserts or any type of genomic DNA fragments harboring the selected biallelic markers already constitutes a physical map of the genome or any portion thereof, using the known order of the DNA fragments will allow the order of the biallelic markers to be established.

As discussed above, it will be appreciated that markers carried by the same fragment of genomic DNA, such as the insert in a BAC clone, need not necessarily be ordered with respect to one another within the genomic fragment to conduct single point or haplotype association analyses. However, in other embodiments of the maps, the order of biallelic markers carried by the same fragment of genomic DNA may be determined.

The positions of the biallelic markers used to construct the maps of the present invention may be assigned to subchromosomal locations using Fluorescence In Situ Hybridization (FISH) (Cherifet al., *Proc. Natl. Acad. Sci. U.S.A.*, 87:6639–6643 (1990), the disclosure of which is incorporated herein by reference). FISH analysis is described in Example 8 below. This procedure was used to confirm the subchromosomal location of numerous biallelic markers obtained using the methods described above. Simple identification numbers were attributed to each BAC from which the markers were derived. FIG. 1 is a cytogenetic map of chromosome 21 indicating the subchromosomal regions therein. Amplification primers for generating amplification products containing the polymorphic bases of these markers and microsequencing primers for use in determining the identities of the polymorphic bases of these biallelic markers were also designed.

The rate at which biallelic markers may be assigned to subchromosomal regions may be enhanced through automation. For example, probe preparation may be performed in a microtiter plate format, using adequate robots. The rate at which biallelic markers may be assigned to subchromosomal regions may be enhanced using techniques which permit the in situ hybridization of multiple probes on a single microscope slide, such as those disclosed in Larin et al., Nucleic Acids Research 22: 3689–3692 (1994), the disclosure of which is incorporated herein by reference. In the largest test format described, different probes were hybridized simultaneously by applying them directly from a 96-well microtiter dish which was inverted on a glass plate. Software for image data acquisition and analysis that is adapted to each optical system, test format, and fluorescent probe used, can be derived from the system described in Lichter et al. *Science* 247: 64 69 (1990), the disclosure of which is incorporated herein by reference. Such software measures the relative distance between the center of the fluorescent spot corresponding to the hybridized probe and the telomeric end of the short arm of the corresponding chromosome, as compared to the total length of the chromosome. The rate at which biallelic markers are assigned to subchromosomal locations may be further enhanced by simultaneously applying probes labeled with different fluorescent tags to each well of the 96 well dish. A further benefit of conducting the analysis on one slide is that it facilitates automation, since a microscope having a moving stage and the capability of detecting fluorescent signals in different metaphase chromosomes could provide the coordinates of each probe on the metaphase chromosomes distributed on the 96 well dish.

Example 9 below describes an alternative method to position biallelic markers which allows their assignment to human chromosomes.

The ordering analyses described above may be conducted to generate an integrated genome wide genetic map comprising about 20,000 biallelic markers (1 biallelic marker per BAC if 20,000 BAC inserts are screened). In another embodiment, the above procedures are conducted to generate a map comprising about 40,000 markers (an average of 2 biallelic markers per BAC if 20,000 BAC inserts are screened). In a further embodiment preferred embodiment, the above procedures are conducted to generate a map comprising about 60,000 markers (an average of 3 biallelic markers per BAC if 20,000 BAC inserts are screened). In a further embodiment preferred embodiment, the above procedures are conducted to generate a map comprising about 80,000 markers (an average of 4 biallelic markers per BAC if 20,000 BAC inserts are screened). In yet another embodiment, the above procedures are conducted to generate a map comprising about 100,000 markers (an average of 5 biallelic markers per BAC if 20,000 BAC inserts are screened). In a further embodiment, the above procedures are conducted to generate a map comprising about 120,000 markers (an average of 6 biallelic markers per BAC if 20,000 BAC inserts are screened).

Alternatively, maps having the above-specified average numbers of biallelic markers per BAC which comprise smaller portions of the genome, such as a set of chromosomes, a single chromosome, a particular subchromosomal region, or any other desired portion of the genome, may also be constructed using the procedures provided herein.

In some embodiments, the biallelic markers in the map are separated from one another by an average distance of 10–200 kb. In further embodiments, the biallelic markers in the map are separated from one another by an average distance of 15–150 kb. In yet another embodiment, the biallelic markers in the map are separated from one another by an average distance of 20–100 kb. In other embodiments, the biallelic markers in the map are separated from one another by an average distance of 100–150 kb. In further embodiments, the biallelic markers in the map are separated from one another by an average distance of 50–100 kb. In yet another embodiment, the biallelic markers in the map are separated from one another by an average distance of 25–50 kb. Maps having the above-specified intermarker distances which comprise smaller portions of the genome, such as a set of chromosomes, a single chromosome, a particular subchromosomal region, or any other desired portion of the genome, may also be constructed using the procedures provided herein.

FIG. 2, showing the results of computer simulations of the distribution of inter-marker spacing on a randomly distributed set of biallelic markers, indicates the percentage of biallelic markers which will be spaced a given distance apart for a given number of markers/BAC in the genomic map (assuming 20,000 BACs constituting a minimally overlapping array covering the entire genome are evaluated). One hundred iterations were performed for each simulation (20,000 marker map, 40,000 marker map, 60,000 marker map, 120,000 marker map).

Figure 2A:
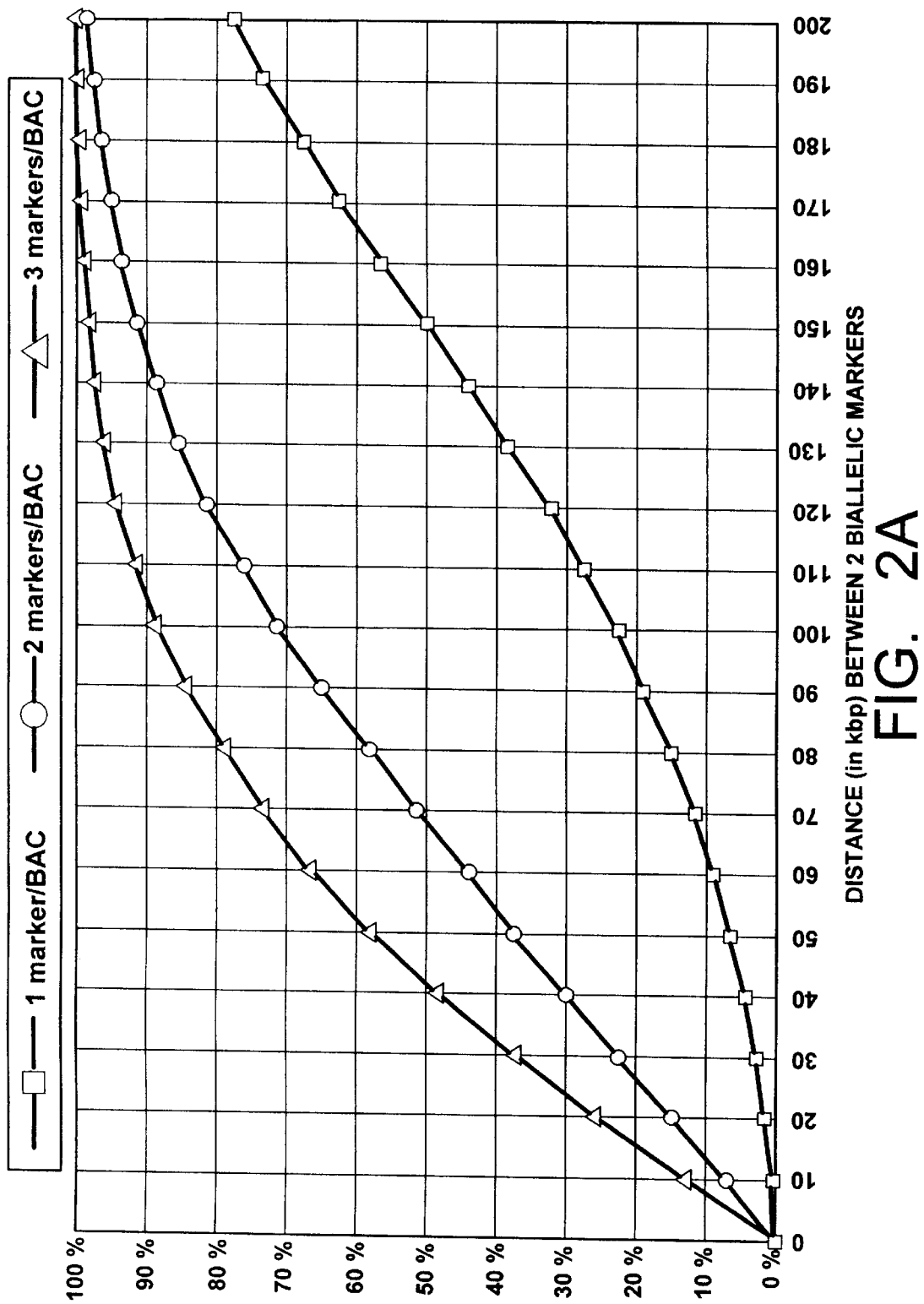
FIG. 2A shows the results of a computer simulation of the distribution of inter-marker spacing on a randomly distributed set of biallelic markers indicating the percentage of biallelic markers which will be spaced a given distance apart for 1, 2, or 3 markers/BAC in a genomic map (assuming a set of 20,000 minimally overlapping BACs covering the genome are evaluated).

As illustrated in FIG. 2A, 98% of inter-marker distances will be lower than 150 kb provided 60,000 evenly distributed markers are generated (3 per BAC); 90% of inter-marker distances will be lower than 150 kb provided 40,000 evenly distributed markers are generated (2 per BAC); and 50% of inter-marker distances will be lower than 150 kb provided 20,000 evenly distributed markers are generated (1 per BAC).

Figure 2B:
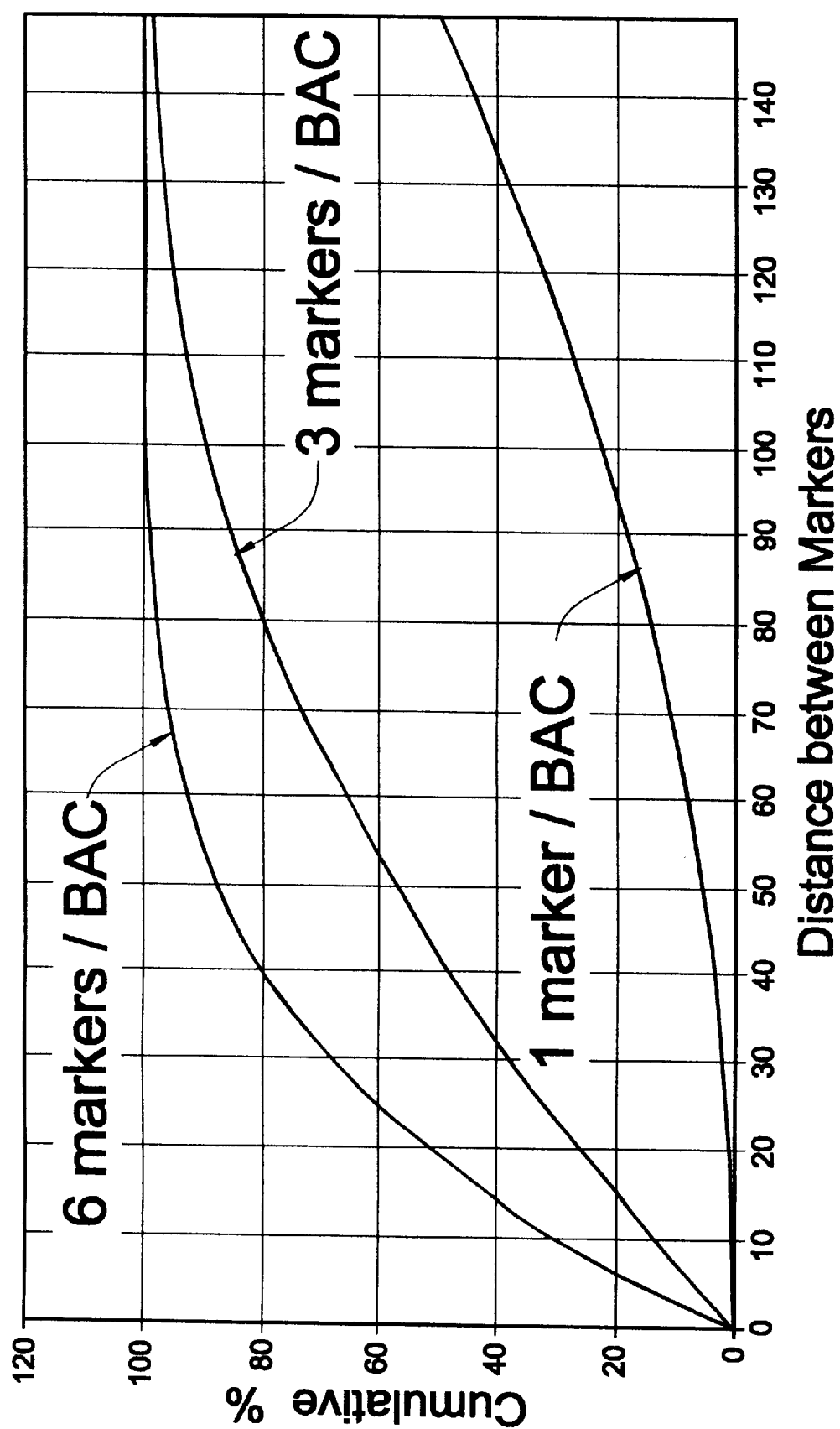
FIG. 2B shows the results of a computer simulation of the distribution of inter-marker spacing on a randomly distributed set of biallelic markers indicating the percentage of biallelic markers which will be spaced a given distance apart for 1, 3, or 6 markers/BAC in a genomic map (assuming a set of 20,000 minimally overlapping BACs covering the genome are evaluated).

As illustrated in FIG. 2B, 98% of inter-marker distances will be lower than 80 kb provided 120,000 evenly distributed markers are generated (6 per BAC); 80% of inter-marker distances will be lower than 80 kb provided 60,000 evenly distributed markers are generated (3 per BAC); and 15% of inter-marker distances will be lower than 80 kb provided 20,000 evenly distributed markers are generated (1 per BAC).

As already mentioned, high density biallelic marker maps allow association studies to be performed to identify genes involved in complex traits.

Association studies examine the frequency of marker alleles in unrelated trait positive (T+) individuals compared with trait negative (T−) controls, and are generally employed in the detection of polygenic inheritance.

Association studies as a method of mapping genetic traits rely on the phenomenon of linkage disequilibrium, which is described below.

Linkage Disequilibrium

If two genetic loci lie on the same chromosome, then sets of alleles on the same chromosomal segment (called haplotypes) tend to be transmitted as a block from generation to generation. When not broken up by recombination, haplotypes can be tracked not only through pedigrees but also through populations. The resulting phenomenon at the population level is that the occurrence of pairs of specific alleles at different loci on the same chromosome is not random, and the deviation from random is called linkage disequilibrium (LD).

If a specific allele in a given gene is directly involved in causing a particular trait T, its frequency will be statistically increased in a T+ population when compared to the frequency in a T− population. As a consequence of the existence of LD, the frequency of all other alleles present in the haplotype carrying the trait-causing allele (TCA) will also be increased in T+ individuals compared to T− individuals. Therefore, association between the trait and any allele in linkage disequilibrium with the trait-causing allele will suffice to suggest the presence of a trait-related gene in that particular allele's region. Linkage disequilibrium allows the relative frequencies in T+ and T− populations of a limited number of genetic polymorphisms (specifically biallelic markers) to be analyzed as an alternative to screening all possible functional polymorphisms in order to find trait-causing alleles.

LD among a set of biallelic markers having an adequate heterozygosity rate can be determined by genotyping between 50 and 1000 unrelated individuals, preferably between 75 and 200, more preferably around 100. Genotyping a biallelic marker consists of determining the specific allele carried by an individual at the given polymorphic base of the biallelic marker. Genotyping can be performed using similar methods as those described above for the generation of the biallelic markers, or using other genotyping methods such as those further described below.

LD between any pair of biallelic markers comprising at least one of the biallelic markers of the present invention ($M_i$, $M_j$) can be calculated for every allele combination ($M_{i1},M_{j1}$; $M_{i1},M_{j2}$; $M_{i2},M_{j1}$ and $M_{i2},M_{j2}$), according to the Piazza formula:

$$\Delta M_{ik},M_{jl}=\sqrt{\theta 4}-\sqrt{(\theta 4+\theta 3)(\theta 4+\theta 2)},$$

where:

θ4=−−=frequency of genotypes not having allele k at $M_i$ and not having allele l at $M_j$ θ3=−+=frequency of genotypes not having allele k at $M_i$ and having allele l at $M_j$ θ2=+−=frequency of genotypes having allele k at Mi and not having allele l at $M_j$ Linkage disequilibrium (LD) between pairs of biallelic markers (Mi, Mj) can also be calculated for every allele combination (Mi1,Mj1; Mi1,Mj2; Mi2,Mj1; Mi2,Mj2) according to the maximum likelihood estimate (MLE) for delta (the composite linkage disequilibrium coefficient), as described by Weir (B. S. Weir, *Genetic Data Analysis*, (1996), Sinauer Ass. Eds, the disclosure of which is incorporated herein by reference). This formula allows linkage disequilibrium between alleles to be estimated when only genotype, and not haplotype, data are available. This LD composite test makes no assumption for random mating in the sampled population, and thus seems to be more appropriate than other LD tests for genotypic data.

Another means of calculating the linkage disequilibrium between markers is as follows. For a couple of biallelic markers, Mi ($a_i/b_i$) and Mj ($a_j/b_j$), fitting the Hardy-Weinberg equilibrium, one can estimate the four possible haplotype frequencies in a given population according to the approach described above.

The estimation of gametic disequilibrium between ai and aj is simply:

$$D_{aiaj}=pr(\text{halotype}(a_i,a_j))-pr(a_i).pr(a_j).$$

Where pr(ai) is the probability of allele ai and aj is the probability of allele aj. and where pr(haplotype (ai, aj)) is estimated as in eq3 above. For a couple of biallelic marker only one measure of disequilibrium is necessary to describe the association between Mi and Mj.

Then a normalized value of the above is calculated as follows:

$$D'aiaj=Daiaj/\max(-pr(ai).pr(aj),-pr(bi).(bj)) \text{ with Daiji}<0$$

$$D'aiaj=Daiaj/\min(pr(bi).pr(aj),-pr(ai).(bj)) \text{ with Daiji}>0$$

The skilled person will readily appreciate that other LD calculation methods can be used without undue experimentation.

As depicted in FIG. 2c, the above method was utilized on 54 random BACs covering 8100 kb. The average inter-marker distances and linkage disequilibrium between markers were determined. At an average intermarker distance of 38 kb the average linkage disequilibrium estimate was 0.63. In contrast, for 19 unlinked markers the average linkage disequilibrium estimate was 0.12.

Example 10 illustrates the measurement of LD between a publicly known biallelic marker, the "ApoE Site A", located within the Alzheimer's related ApoE gene, and other biallelic markers randomly derived from the genomic region containing the ApoE gene.

Genome-wide LD mapping aims at identifying, for any TCA being searched, at least one biallelic marker in LD with said TCA. Preferably, in order to enhance the power of LD maps, in some embodiments, the biallelic markers therein have average inter-marker distances of 150 kb or less, 75 kb or less, or 50 kb or less, 30 kb or less, or 25 kb or less to accommodate the fact that, in some regions of the genome, the detection of LD requires lower inter-marker distances.

The methods described herein allow the generation of biallelic marker maps with average inter-marker distances of 150 kb or less. In some embodiments, the mean distance between biallelic markers constituting the high density map will be less than 75 kb, preferably less than 50 kb. Further preferred maps according to the present invention contain markers that are less than 37.5 kb apart. In highly preferred embodiments, the average inter-marker spacing for the biallelic markers constituting very high density maps is less than 30 kb, most preferably less than 25 kb.

Genetic maps containing biallelic markers may be used to identify and isolate genes associated with detectable traits. The use of the genetic maps of the present invention is described in more detail below.

Use of the High Density Biallelic Marker Map to Identify Genes Associated with a Detectable Trait The biallelic marker maps described above may be used in methods for identifying and isolating genes associated with a detectable trait.

In the past, the identification of genes linked with detectable traits has relied on a statistical approach called linkage analysis. Linkage analysis is based upon establishing a correlation between the transmission of genetic markers and that of a specific trait throughout generations within a family. In this approach, all members of a series of affected families are genotyped with a few hundred markers, typically microsatellite markers, which are distributed at an average density of one every 10 Mb. By comparing genotypes in all family members, one can attribute sets of alleles to parental haploid genomes (haplotyping or phase determination). The origin of recombined fragments is then determined in the offspring of all families. Those that co-segregate with the trait are tracked. After pooling data from all families, statistical methods are used to determine the likelihood that the marker and the trait are segregating independently in all families. As a result of the statistical analysis, one or several regions having a high probability of harboring a gene linked to the trait are selected as candidates for further analysis. The result of linkage analysis is considered as significant (i.e. there is a high probability that the region contains a gene involved in a detectable trait) when the chance of independent segregation of the marker and the trait is lower than 1 in 1000 (expressed as a LOD score >3). Generally, the length of the candidate region identified using linkage analysis is between 2 and 20 Mb.

Once a candidate region is identified as described above, analysis of recombinant individuals using additional markers allows further delineation of the candidate linked region.

Linkage analysis studies have generally relied on the use of a maximum of 5,000 microsatellite markers, thus limiting the maximum theoretical attainable resolution of linkage analysis to ca. 600 kb on average.

Linkage analysis has been successfully applied to map simple genetic traits that show clear Mendelian inheritance patterns and which have a high penetrance (penetrance is the ratio between the number of trait positive carriers of allele a and the total number of a carriers in the population). About 100 pathological trait-causing genes were discovered using linkage analysis over the last 10 years. In most of these cases, the majority of affected individuals had affected relatives and the detectable trait was rare in the general population (frequencies less than 0.1%). In about 10 cases, such as Alzheimer's Disease, breast cancer, and Type II diabetes, the detectable trait was more common but the allele associated with the detectable trait was rare in the affected population. Thus, the alleles associated with these traits were not responsible for the trait in all sporadic cases.

Linkage analysis suffers from a variety of drawbacks. First, linkage analysis is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis.

In addition, linkage analysis approaches have proven difficult when applied to complex genetic traits, such as those due to the combined action of multiple genes and/or environmental factors. In such cases, too large an effort and cost are needed to recruit the adequate number of affected families required for applying linkage analysis to these situations, as recently discussed by Risch, N. and Merikangas, K. (*Science* 273:1516–1517 (1996), the disclosure of which is incorporated herein by reference).

Finally, linkage analysis cannot be applied to the study of traits for which no large informative families are available. Typically, this will be the case in any attempt to identify trait-causing alleles involved in sporadic cases, such as alleles associated with positive or negative responses to drug treatment.

The maps and biallelic markers obtained as described herein may be used to identify and isolate genes associated with detectable traits using association studies, an approach which does not require the use of affected families and which permits the identification of genes associated with sporadic traits.

Association studies are described in more detail below.

Association Studies

As already mentioned, any gene responsible or partly responsible for a given trait will be in LD with some flanking markers. To map such a gene, specific alleles of these flanking markers which are associated with the gene or genes responsible for the trait are identified. Although the following discussion of techniques for finding the gene or genes associated with a particular trait using linkage disequilibrium mapping, refers to locating a single gene which is responsible for the trait, it will be appreciated that the same techniques may also be used to identify genes which are partially responsible for the trait.

Association studies may be conducted within the general population (as opposed to the linkage analysis techniques discussed above which are limited to studies performed on related individuals in one or several affected families).

Association between a biallelic marker A and a trait T may primarily occur as a result of three possible relationships between the biallelic marker and the trait.

First, allele a of biallelic marker A may be directly responsible for trait T (e.g., Apo E ∈4 site A and Alzheimer's disease). However, since the majority of the biallelic markers used in genetic mapping studies are selected randomly, they mainly map outside of genes. Thus, the likelihood of allele a being a functional mutation directly related to trait T is very low.

Second, an association between a biallelic marker A and a trait T may also occur when the biallelic marker is very closely linked to the trait locus. In other words, an association occurs when allele a is in linkage disequilibrium with the trait-causing allele. When the biallelic marker is in close proximity to a gene responsible for the trait, more extensive genetic mapping will ultimately allow a gene to be discovered near the marker locus which carries mutations in people with trait T (i.e. the gene responsible for the trait or one of the genes responsible for the trait). As will be further exemplified below, using a group of biallelic markers which are in close proximity to the gene responsible for the trait the location of the causal gene can be deduced from the profile of the association curve between the biallelic markers and the trait. The causal gene will usually be found in the vicinity of the marker showing the highest association with the trait.

Finally, an association between a biallelic marker and a trait may occur when people with the trait and people without the trait correspond to genetically different subsets of the population who, coincidentally, also differ in the frequency of allele a (population stratification). This phenomenon may be avoided by using large ethnically matched samples.

Association studies are particularly suited to the efficient identification of genes that present common polymorphisms, and are involved in multifactorial traits whose frequency is relatively higher than that of diseases with monofactorial inheritance.

Association studies mainly consist of four steps: recruitment of trait-positive (T+) and trait-negative (T−) populations with well-defined phenotypes, identification of a candidate region suspected of harboring a trait causing gene, identification of said gene among candidate genes in the region, and finally validation of mutation(s) responsible for the trait in said trait causing gene.

In a first step, trait+ and trait− phenotypes have to be well-defined. In order to perform efficient and significant association studies such as those described herein, the trait under study should preferably follow a bimodal distribution in the population under study, presenting two clear non-overlapping phenotypes, trait + and trait −.

Nevertheless, in the absence of such a bimodal distribution (as may in fact be the case for complex genetic traits), any genetic trait may still be analyzed using the association method proposed herein by carefully selecting the individuals to be included in the trait + and trait − phenotypic groups. The selection procedure involves selecting individuals at opposite ends of the non-bimodal phenotype spectrum of the trait under study, so as to include in these trait + and trait − populations individuals who clearly represent non-overlapping, preferably extreme phenotypes.

The definition of the inclusion criteria for the trait + and trait − populations is an important aspect of the present invention. The selection of those drastically different but relatively uniform phenotypes enables efficient comparisons in association studies and the possible detection of marked differences at the genetic level, provided that the sample sizes of the populations under study are significant enough.

Generally, trait + and trait − populations to be included in association studies such as those proposed in the present invention consist of phenotypically homogeneous populations of individuals each representing 100% of the corresponding phenotype if the trait distribution is bimodal. If the trait distribution is non-bimodal, trait + and trait − populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and selected among individuals exhibiting non-overlapping phenotypes. In some embodiments, the $T^+$ and $T^-$ groups consist of individuals exhibiting the extreme phenotypes within the studied population. The clearer the difference between the two trait phenotypes, the greater the probability of detecting an association with biallelic markers.

In preferred embodiments, a first group of between 50 and 300 trait + individuals, preferably about 100 individuals, are recruited according to their phenotypes. In each case, a similar number of trait negative individuals are included in such studies who are preferably both ethnically- and age-matched to the trait positive cases. Both trait + and trait − individuals should correspond to unrelated cases.

FIG. 3 shows, for a series of hypothetical sample sizes, the p-value significance obtained in association studies performed using individual markers from the high-density biallelic map, according to various hypotheses regarding the difference of allelic frequencies between the T+ and T− samples. It indicates that, in all cases, samples ranging from 150 to 500 individuals are numerous enough to achieve statistical significance. It will be appreciated that bigger or smaller groups can be used to perform association studies according to the methods of the present invention.

In a second step, a marker/trait association study is performed that compares the genotype frequency of each biallelic marker in the above described T+ and T− populations by means of a chi square statistical test (one degree of freedom). In addition to this single marker association analysis, a haplotype association analysis is performed to define the frequency and the type of the ancestral carrier haplotype. Haplotype analysis, by combining the informativeness of a set of biallelic markers increases the power of the association analysis, allowing false positive and/or negative data that may result from the single marker studies to be eliminated.

Genotyping can be performed using the microsequencing procedure described in Example 13, or any other genotyping procedure suitable for this intended purpose.

If a positive association with a trait is identified using an array of biallelic markers having a high enough density, the causal gene will be physically located in the vicinity of the associated markers, since the markers showing positive association with the trait are in linkage disequilibrium with the trait locus. Regions harboring a gene responsible for a particular trait which are identified through association studies using high density sets of biallelic markers will, on average, be 20–40 times shorter in length than those identified by linkage analysis.

Once a positive association is confirmed as described above, a third step consists of completely sequencing the BAC inserts harboring the markers identified in the association analyzes. These BACs are obtained through screening human genomic libraries with the markers probes and/or primers, as described herein. Once a candidate region has been sequenced and analyzed, the functional sequences within the candidate region (e.g. exons, splice sites, promoters, and other potential regulatory regions) are scanned for mutations which are responsible for the trait by comparing the sequences of the functional regions in a selected number of T+ and T− individuals using appropriate software. Tools for sequence analysis are further described in Example 14.

Finally, candidate mutations are then validated by screening a larger population of T+ and T− individuals using genotyping techniques described below. Polymorphisms are confirmed as candidate mutations when the validation population shows association results compatible with those found between the mutation and the trait in the test population.

In practice, in order to define a region bearing a candidate gene, the trait + and trait − populations are genotyped using an appropriate number of biallelic markers. The markers used to define a region bearing a candidate gene may be distributed at an average density of 1 marker per 10–200 kb. Preferably, the markers used to define a region bearing a candidate gene are distributed at an average density of 1 marker every 15–150 kb. In further preferred methods, the markers used to define a region bearing a candidate gene are distributed at an average density of 1 marker every 20–100 kb. In yet another preferred method, the markers used to define a region bearing a candidate gene are distributed at an average density of 1 marker every 100 to 150 kb. In a further highly preferred method, the markers used to define a region bearing a candidate gene are distributed at an average density of 1 marker every 50 to 100 kb. In yet another method, the biallelic markers used to define a region bearing a candidate gene are distributed at an average density of 1 marker every 25–50 kilobases. As mentioned above, in order to enhance the power of linkage disequilibrium based maps, in a preferred embodiment, the marker density of the map will be adapted to take the linkage disequilibrium distribution in the genomic region of interest into account.

In some methods, the initial identification of a candidate genomic region harboring a gene associated with a detectable phenotype may be conducted using a preliminary map containing a few thousand biallelic markers. Thereafter, the genomic region harboring the gene responsible for the detectable trait may be better delineated using a map containing a larger number of biallelic markers. Furthermore, the genomic region harboring the gene responsible for the detectable trait may be further delineated using a high density map of biallelic markers. Finally, the gene associated with the detectable trait may be identified and isolated using a very high density biallelic marker map.

Example 11 describes a hypothetical procedure for identifying a candidate region harboring a gene associated with a detectable trait. It will be appreciated that although Example 11 compares the results of analyzes using markers derived from maps having 3,000, 20,000, and 60,000 markers, the number of markers contained in the map is not restricted to these exemplary figures. Rather, Example 11 exemplifies the increasing refinement of the candidate region with increasing marker density. As increasing numbers of markers are used in the analysis, points in the association analysis become broad peaks. The gene associated with the detectable trait under investigation will lie within or near the region under the peak.

The statistical power of LD mapping using a high density marker map is also reinforced by complementing the single point association analysis described in Example 11 with a multi-marker association analysis, called haplotype analysis.

When a chromosome carrying a disease allele is first introduced into a population as a result of either mutation or migration, the mutant allele necessarily resides on a chromosome having a unique set of linked markers: the ancestral haplotype. As already mentioned, a haplotype association analysis allows the frequency and the type of the ancestral carrier haplotype to be defined.

A haplotype analysis is performed by estimating the frequencies of all possible haplotypes for a given set of biallelic markers in the T+ and T− populations, and comparing these frequencies by means of a chi square statistical test (one degree of freedom).

In a diploid population of unrelated individuals, the estimation of multi-locus haplotype frequencies based on observed genotypes is problematic because the gametic phase of genotype (i.e. the sets of alleles of the different markers transmitted together by the parents) cannot be unambiguously inferred, as simply shown in the following example:

Suppose two biallelic markers Mi and Mj with alleles ai/bi and aj/bj. Suppose an individual, heterozygote at the two markers. His genotype is thus (ai,bi;aj,bj). Without any additional information, the possible phases are either:

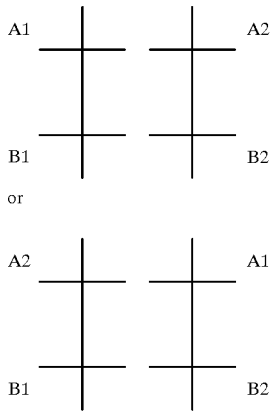

This example for two loci can be easily generalized for an arbitrary number of biallelic loci. For a given set of markers, ambiguous phase occur for each individual being heterozyguous at two or more sites. To overcome this difficulty, an algorithm was described and implemented (Excoffier L, Slatkin M (1995) Maximum-likelihood estimation of molecular haplotype frequencies in a diploid population. Mol.Biol.Evol. 12: 921–927, the disclosure of which is incorporated herein by reference) which allows maximum likelihood estimation of haplotypes frequencies using the general framework of E-M algorithms (Dempster A. P. (1977) Maximum likelihood from incomplete data via the EM algorithm. J. Roy. Stat. Soc. 39: 1–38, the disclosure of which is incorporated herein by reference).

This type of algorithm is used for handling data where categories of interest (here the haplotypes) cannot be directly distinguished from the observed data (unknown-phase multi-locus genotypes).

The present approach relies on the hypothesis that all markers fit the Hardy-Weinberg equilibrium.

In the present invention, the estimations may be performed by applying the Expectation-Maximization (EM) algorithm (Excoffier L and Slatkin M, Mol. Biol. Evol. 12:921–927 (1995), the disclosure of which is incorporated herein by reference), using the EM-HAPLO program (Hawley M E, Pakstis A J & Kidd K K, Am. J. Phys. Anthropol. 18:104 (1994), the disclosure of which is incorporated herein by reference). The EM algorithm is used to estimate haplotype frequencies in the case when only genotype data from unrelated individuals are available. The EM algorithm is a generalized iterative maximum likelihood approach to estimation that is useful when data are ambiguous and/or incomplete.

In the E-M algorithm, the assumption is made that the Hardy-Weinberg equilibrium holds for the markers in the markers involved in the haplotype whose frequencies are estimated in the population at study.

Hardy-Weinberg equilibrium is a hypothesis relative to one marker and one population. It supposes that the population is sufficiently large and that the mating is random at that locus. Hence, if, at that polymorphic locus, there are no perturbing forces such as migration, selection, or mutation, the genotype frequencies will be the products of allelic frequencies of each of the two alleles involved in the genotype, i.e. alleles are statistically independent in a genotype.

Consider one biallelic marker M with allele A and B, and $p_A$ and $p_B$ the allelic frequencies and $p_{AA}$, $p_{AB}$ and $p_{BB}$ the genotypes frequencies.

One parameter, $D_A$, can measure the departure from Hardy-Weinberg equilibrium, which is:

$$D_A = p_{AA} - (p_A)^2$$

It should be noted that $D_A$ is also:

$$D_A = p_{BB} - (p_B)^2 - 2D_A = p_{AB} - 2*(p_A \cdot p_B)$$

In a sample of N individuals, one can test the Hardy-Weinberg hypothesis using the statistical test:

$$X^2 = \frac{N \cdot \hat{D}_A}{\hat{p}_A^2 \cdot (1 - \hat{p}_A^2)},$$

where $\hat{p}_A$ and $\hat{D}_A$ are the estimation of allelic frequency and the departure from Hardy-Weinberg equilibrium estimations in the sample of N individuals.

For a large sample, as described in Weir (supra), the statistics follow a chi-square with one degree of freedom. For large estimation of departure from Hardy-Weinberg equilibrium, the statistic will have large values leading to the rejection of the hypothesis of equilibrium for the considered marker in the population. For testing Hardy-Weinberg equilibrium one can also use exact tests (Weir 1996, supra).

In the following part of this text, phenotypes will refer to multi-locus genotypes with unknown phase. Genotypes will refer to known-phase multi-locus genotypes.

Suppose a sample of N unrelated individuals typed for K markers. The data observed are the unknown-phase K-locus phenotypes that can categorized in F different phenotypes. Suppose that we have H underlying possible haplotypes (in case of K biallelic markers, $H=2^K$).

For phenotype j, suppose that cj genotypes are possible. We thus have the following equation:

$$P_j = \sum_{i=1}^{c_j} pr(genotype_i) = \sum_{i=1}^{c_j} pr(h_k, h_l) \qquad \text{eq. 1}$$

where Pj is the probability of the phenotype j, hk and hl are the two haplotypes constituent the genotype i. Under the Hardy-Weinberg equilibrium, pr(hk,hl) becomes:

$$pr(h_k,h_l)=pr(h_k)^2 \text{ if } h_k=h_l, \ pr(h_k,h_l)=2pr(h_k).pr(h_l) \text{ if } h_k\neq h_l. \qquad \text{eq.2}$$

The successive steps of the E-M algorithm can be described as follows: Starting with initial values of the of haplotypes frequencies, noted, $p_1^{(0)}, p_2^{(0)}, \ldots p_T^{(0)}$. these initial values serves to estimate the genotypes frequencies (Expectation step) and then estimate another set of haplotype frequencies (Maximisation step): $p_1^{(1)}, p_2^{(1)}, \ldots p_T^{(1)}$. these two steps are iterated until change in the sets of haplotypes frequency are very small.

A stop criterion can be that the maximum difference between haplotype frequencies between wo iterations is less than $10^{-7}$. This values can be adjusted according to the desired precision of estimations.

In details, at a given iteration s, the Expectation step consists in calculating the genotypes frequencies by the following equation:

$$pr(genotype_i)^{(s)} = pr(phenotype_j) \cdot pr(genotype_i | phenotype_j)^{(s)} \qquad \text{eq. 3}$$
$$= \frac{n_j}{N} \cdot \frac{pr(h_k, h_l)^{(s)}}{p_j^{(s)}}$$

where genotype i occurs in phenotype j, and where hk and hi constitute genotype i. Each probability are derived according to eq.1, and eq.2 above.

Then the Maximisation step simply estimates another set of haplotype frequencies given the genotypes frequencies. This approach is also known as gene-counting method (Smith CAB (1957) Counting methods in genetical statistics, Ann. Hum. Genet. 21:254–276, the disclosure of which is incorporated herein by reference).

$$p_t^{(s+1)} = \frac{1}{2}\sum_{j=1}^{F}\sum_{i=1}^{c_j} \delta_{it} \cdot pr(genotype_i)^{(s)} \qquad \text{eq. 4}$$

where $\delta_{it}$ is an indicator variable which count the number of time haplotype t in genotype i. It takes the values of 0, 1 or 2.

To ensure that the estimation finally obtained are the maximum-likelihood estimations several values of departures are required. The estimations obtained are compared and if they differ the estimations leading to the best likelihood are kept.

To improve the statistical power of the individual marker association analyses using maps of increasing marker densities, haplotype studies can be performed using groups of markers located in proximity to one another within regions of the genome. For example, using the methods in which the association of an individual marker with a detectable phenotype was analyzed using maps of 3,000 markers, 20,000 markers, and 60,000 markers, a series of haplotype studies can be performed using groups of contiguous markers from such maps or from maps having higher marker densities.

In a preferred embodiment, a series of successive haplotype studies including groups of markers spanning regions of more than 1 Mb may be performed. In some embodiments, the biallelic markers included in each of these groups may be located within a genomic region spanning less than 1 kb, from 1 to 5 kb, from 5 to 10 kb, from 10 to 25 kb, from 25 to 50 kb, from 50 to 150 kb, from 150 to 250 kb, from 250 to 500 kb, from 500 kb to 1 Mb, or more than 1 Mb. Preferably, the genomic regions containing the groups of biallelic markers used in the successive haplotype analyses are overlapping. It will be appreciated that the groups of biallelic markers need not completely cover the genomic regions of the above-specified lengths but may instead be obtained from incomplete contigs having one or more gaps therein. As discussed in further detail below, biallelic markers may be used in single point and haplotype association analyses regardless of the completeness of the corresponding physical contig harboring them.

It will be appreciated that the above approaches may be conducted on any scale (i.e. over the whole genome, a set of chromosomes, a single chromosome, a particular subchromosomal region, or any other desired portion of the genome). As mentioned above, once significance thresholds have been assessed, population sample sizes may be adapted as exemplified in FIG. 3.

The methods described in Examples 20–23 below allow the determination of whether a candidate genomic region suspected of harboring one or more genes associated with a detectable trait warrants further evaluation. The candidate genomic region may be identified as described above or, alternatively, the candidate genomic region may be selected on the basis of an already suspected association with the detectable trait as described in Examples 12–19 below.

The methods of the present invention involve performing haplotype analyses on groups of biallelic markers. Example 12 below illustrates the increase in statistical power brought to an association study by a haplotype analysis.

Once a given polymorphic site has been found and characterized as a biallelic marker according to the methods of the present invention, several methods can be used in order to determine the specific allele carried by an individual at the given polymorphic base.

Most genotyping methods require the previous amplification of a DNA region carrying the polymorphic site of interest.

The identification of biallelic markers described previously, allows the design of appropriate oligonucleotides, which can be used as primers to amplify a DNA fragment containing the polymorphic site of interest and for the detection of such polymorphisms.

For example, in the examples below, pairs of primers of SEQ ID Nos: 13–18 and 19–23 may be used to generate amplicons harboring the markers of SEQ ID Nos: 1–6 and 7–12 or the sequences complementary thereto.

It will be appreciated that amplification primers may be designed having any length suitable for their intended purpose, in particular any length allowing their hybridization with a region of the DNA fragment to be amplified.

It will be further appreciated that the hybridization site of said amplification primers may be located at any distance from the polymorphic base to be genotyped, provided said amplification primers allow the proper amplification of a DNA fragment carrying said polymorphic site. The amplification primers may be oligonucleotides of 10, 15, 20 or more bases in length which enable the amplification of the polymorphic site in the markers. In some embodiments, the amplification product produced using these primers may be at least 100 bases in length (i.e. on average 50 nucleotides on each side of the polymorphic base). In other embodiments, the amplification product produced using these primers may be at least 500 bases in length (i.e. on average 250 nucleotides on each side of the polymorphic base). In still further embodiments, the amplification product produced using these primers may be at least 1000 bases in length (i.e. on average 500 nucleotides on each side of the polymorphic base).

The amplification of polymorphic fragments can be performed as described in Example 6 on DNA samples extracted as described in Example 5.

As already mentioned, allele frequencies of biallelic markers tested in association studies (individual or haplotype) may be determined using microsequencing procedures.

A first step in microsequencing procedures consists in designing microsequencing primers adapted to each biallelic marker to be genotyped. Microsequencing primers hybridize upstream of the polymorphic base to be genotyped, either with the coding or with the non-coding strand. Microsequencing primers may be oligonucleotides of 8, 10, 15, 20 or more bases in length. Preferably, the 3' end of the microsequencing primer is immediately upstream of the polymorphic base of the biallelic marker being genotyped, such that upon extension of the primer, the polymorphic base is the first base incorporated.

It will be appreciated that the biallelic markers of the present invention may be genotyped using microsequencing primers having any desirable length and hybridizing to any of the strands of the marker to be tested, provided their design is suitable for their intended purpose. In some embodiments, the amplification primers or microsequencing primers may be labeled. For example, in some embodiments, the amplification primers or microsequencing primers may be biotinylated.

Typical microsequencing procedures that can be used in the context of the present invention are described in Example 13 below.

As another alternative, solid phase microsequencing reactions have been developed, for which either the oligonucleotide microsequencing primers or the PCR-amplified products derived from the DNA fragment of interest are immobilized. For example, immobilization can be carried out via an interaction between biotinylated DNA and streptavidin-coated microtitration wells or avidin-coated polystyrene particles.

As a further alternative, the PCR reaction generating the amplicons to be genotyped can be performed directly in solid phase conditions, following procedures such as those described in WO 96/13609, the disclosure of which is incorporated herein by reference.

In such solid phase microsequencing reactions, incorporated ddNTPs can either be radiolabeled (see Syvänen, *Clin. Chim. Acta.* 226:225–236 (1994), the disclosure of which is incorporated herein by reference) or linked to fluorescein (see Livak and Hainer, *Hum. Metat.* 3:379–385 (1994), the disclosure of which is incorporated herein by reference). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate).

Other possible reporter-detection couples for use in the above microsequencing procedures include:
- ddNTP linked to dinitrophenyl (DNP) and anti-DNP alkaline phosphatase conjugate (see Harju et al., *Clin Chem*:39(11Pt 1):2282–2287 (1993), incorporated herein by reference)
- biotinylated ddNTP and horseradish peroxidase-conjugated streptavidin with o-phenylenediamine as a substrate (see WO 92/15712, incorporated herein by reference).

A diagnosis kit based on fluorescein-linked ddNTP with antifluorescein antibody conjugated with alkaline phosphatase has been commercialized under the name PRONTO by GamidaGen Ltd.

As yet another alternative microsequencing procedure, Nyren et al. (*Anal. Biochem.* 208:171–175 (1993), the disclosure of which is incorporated herein by reference) have described a solid-phase DNA sequencing procedure that relies on the detection of DNA polymerase activity by an enzymatic luminometric inorganic pyrophosphate detection assay (ELIDA). In this procedure, the PCR-amplified products are biotinylated and immobilized on beads. The microsequencing primer is annealed and four aliquots of this mixture are separately incubated with DNA polymerase and one of the four different ddNTPs. After the reaction, the resulting fragments are washed and used as substrates in a primer extension reaction with all four dNTPs present. The progress of the DNA-directed polymerization reactions is monitored with the ELIDA. Incorporation of a ddNTP in the first reaction prevents the formation of pyrophosphate during the subsequent dNTP reaction. In contrast, no ddNTP incorporation in the first reaction gives extensive pyrophosphate release during the dNTP reaction and this leads to generation of light throughout the ELIDA reactions. From the ELIDA results, the identity of the first base after the primer is easily deduced.

It will be appreciated that several parameters of the above-described microsequencing procedures may be successfully modified by those skilled in the art without undue experimentation. In particular, high throughput improvements to these procedures may be elaborated, following principles such as those described further below.

It will be further appreciated that any other genotyping procedure may be applied to the genotyping of biallelic markers.

Examples 14–19 below illustrate the application of methods using biallelic markers to identify a gene associated with a complex disease, prostate cancer, within a ca. 450 kb candidate region. Additional details of the identification of the gene associated with prostate cancer are provided in the U.S. patent application entitled "Prostate Cancer Gene" (GENSET.018A, Ser. No. 08/996,306), the disclosure of which is incorporated herein by reference.

Once a candidate genomic region, such as a BAC insert, which is suspected of harboring a gene associated with a detectable trait has been identified, it is evaluated using the methods of Examples 20–23 in order to determine whether it is in fact likely to harbor a gene associated with the detectable trait.

If it appears likely that the candidate genomic region harbors a gene associated with the trait, the existence of one or more genes associated with the detectable trait within the candidate region is confirmed by identifying more biallelic markers lying in the candidate region using the techniques described above. Preferably, the biallelic markers in the candidate genomic region have an average intermarker spacing of less than 1 kb, 1–3 kb, 3 kb–5 kb, about 5 kb, about 10 kb, about 20 kb or about 30 kb. In a highly preferred embodiment, the biallelic markers span the entire candidate genomic region. In particular embodiments, all the biallelic markers located in the candidate gene or in the vicinity of the candidate gene may be used in the analysis. In some embodiments, biallelic markers which lie within coding regions may be used. In other embodiments, the biallelic markers used in the analyses may be biallelic markers in which the frequency of the least common allele in the population is at least 30%, at least 20%, or at least 10%. FIG. 14 illustrates that rare biallelic markers may be in linkage disequilibrium with more frequent markers or with other rare markers. Alternatively, biallelic markers inside noncoding exons or inside introns may be used. FIG. 15 illustrates that non-exonic markers may be in linkage disequilibrium with exonic markers or other non-exonic markers. In FIG. 15, Nb pairs are the number of marker pairs for which linkage disequilibrium was calculated.

A first haplotype analysis is performed for each possible combination of groups of biallelic markers within the genomic region suspected of harboring a trait-associated gene. The number of biallelic markers in each group is preferably at least three, but may be two, 4, 5, 6 or groups comprising any number of markers which are compatible with the computer system being used for the analysis. It will be appreciated that the greater the number of markers per group, the greater the number of markers required to perform the analysis and the greater the number of haplotype results which are generated. Thus, with increasing numbers of markers per group, the sample size of the populations needed for the analysis also increases. It will also be appreciated that the relationship between the number of haplotypes generated in the analysis and the number of individuals in the control population and the population expressing the trait which are needed to run the analysis may be influenced by the penetrance of the trait-associated gene, the degree of risk attributable to the gene, and the linkage disequilibrium pattern between the markers around the candidate gene which are used in the analysis. Alternatively, rather than performing haplotype analyses with groups of markers, the association of individual markers with the detectable trait may be measured.

For purposes of exemplifying the present methods, groups of three biallelic markers will be used in the examples below, such that a total of eight combinations of marker alleles are possible for each group. However, it will be appreciated that the methods may be performed with groups of two markers, groups of 3 markers, groups of 4 markers, groups of 5 markers, groups of 6 markers or groups comprising any number of markers which are compatible with the computer system being used for the analysis The frequency of each combination (i.e. each haplotype, or, if individual markers are used, of each allele of the individual markers) is estimated in individuals expressing the trait and individuals who do not express the trait. For example, the frequency of each haplotype (or each allele of the individual markers) in each of the populations of individuals may be estimated using the Expectation-Maximization method of Excoffier L and Slatkin M, *Mol. Biol. Evol.* 12:921–927 (1995), the disclosure of which is incorporated herein by reference and which was described above, using the EM-HAPLO program (Hawley M E, Pakstis A J & Kidd K K, *Am. J. Phys. Antrhopol.* 18:104 (1994), the disclosure of which is incorporated herein by reference). Alternatively, the analysis may be performed using single markers.

The frequencies of each of the possible haplotypes (or each allele of the individual markers) in individuals expressing the trait and individuals who do not express the trait are compared. Preferably, the frequency of each of the possible haplotypes in individuals expressing the trait and individuals who do not express the trait are compared by performing a chi-squared analysis. Within each group of markers, the haplotype (or allele of the individual markers) having the best value (i.e. the greatest association with the trait) is selected for inclusion in a distribution of association values which will be referred to herein as the "candidate region" distribution. For example, if the haplotype or allele frequencies are compared using a chi-squared analysis, the chi-squared value for the combination of markers in each group which has the strongest association with the trait is included in the "candidate region" distribution.

A second haplotype analysis is performed for each possible combination of groups of biallelic markers or individual markers within random genomic regions. For purposes of exemplifying the present methods, groups of three biallelic markers will be used in the examples below, such that a total of eight combinations of marker alleles are possible for each group. However, it will be appreciated that the methods may be performed with groups of two markers, groups of 3 markers, groups of 4 markers, groups of 5 markers, groups of 6 markers or groups comprising any number of markers which are compatible with the computer system being used for the analysis. Preferably, the markers in the random genomic regions have an average intermarker spacing of one marker every 3 kb, one marker every 5 kb, one marker every 10 kb, one marker every 20 kb, or one marker every 30 kb. Alternatively, the markers in the random genomic regions may comprise markers which are not in total linkage disequilibrium with one another. In an alternative embodiment, rather than performing haplotype analyses with groups of markers, the association of individual markers in the random genomic regions with the detectable trait may be measured.

The frequency of each combination (i.e. each haplotype, or, if an individual marker is used, of each allele of the individual marker) is estimated in individuals expressing the trait and individuals who do not express the trait. For example, the frequency of each haplotype (or each allele of an individual marker) in each of the populations of individuals may be estimated using the Expectation-Maximization method of Excoffier and Slatkin and the EM-HAPLO program as described above.

The frequencies of each of the possible haplotypes (or each allele of an individual marker) in individuals expressing the trait and individuals who do not express the trait are compared. Preferably, the frequency of each of the possible haplotypes (or each allele of an individual marker) in individuals expressing the trait and individuals who do not express the trait are compared by performing a chi-squared analysis. Within each group of markers, the chi squared value from the haplotype (or allele of an individual marker) having the the greatest association with the trait is selected for inclusion in a distribution of test values which will be referred to herein as the "random region" distribution.

In some embodiments, the haplotype frequencies (or allele frequencies of individual markers) of biallelic markers in the random genomic regions being considered for inclusion in the construction of the random region distribution are compared to those obtained with markers located in other random genomic regions to ensure that the random genomic regions being considered for inclusion in the random region distribution do not in fact include markers having a significant association with the trait.

Alternatively, to confirm that the markers included in the random genomic regions are suitable for use in the random region distribution, the biallelic markers from the random genomic regions can be randomly split into two halves. A distribution can then be established on each half. It can be assessed whether these two distributions are different. If the difference between the two distributions is not significant, the random marker set is proper. In this manner, all the biallelic markers within the random genomic regions may be included within the random region distribution. This approach is described below.

The candidate distribution of association values and the random region distribution of association values are then compared to one another to determine whether there are significant differences between the two distributions. If there are significant differences between the two distributions, the candidate genomic region is likely to harbor a gene associated with the detectable trait. In contrast if there are not significant differences between the two distributions, the candidate genomic region is unlikely to harbor a gene associated with the detectable trait.

The two distributions may compared to one another using any means familiar to those skilled in the art including, but not limited to, the chi-squared test, tests based on empirical distribution, likelihood ratio test, permutation test, sign test, median test, Wilcoxon rank test and Komogorov-Smirnov test. Preferably, the two distributions are compared to one another using tests which do not assume that the two distributions have a normal distribution. In some preferred embodiments, the two distributions are compared to one another using either the Wilcoxon rank test (Noether, G. E. (1991) *Introduction to statistics: "The nonparametric way"*, Springer-Verlag, New York, Berlin, the disclosure of which is incorporated herein by reference) or the Kolmogorov-Smirnov test (Saporta, G. (1990) *"Probabilités, analyse des donnees et statistiques"* Technip editions, Paris, the disclosure of which is incorporated herein by reference) or both the Wilcoxon rank test and the Kolmogorov-Smirnov test.

In the Wilcoxon rank test, one compares two samples of respectively $n_1$ and $n_2$ values of a continuous variable, here the chi-square values based on haplotypes frequency differences between cases and controls. All $n_1$ and $n_2$ values are pooled and then ordered. Each value gets assigned its rank in such ordered set. Let:

$W_1$=the sum of the rank assigned to the first sample of $n_1$ values, $W_2$=the sum of the rank assigned to the second sample of $n_2$ values.

If $N=n_1+n_2$, the sum of ranks W, is fixed and equals to:

$$W=W_1+W_2=N(N+1)/2.$$

Under the null hypothesis, i.e. the two distributions are equivalent, the expectation and variance of $W_1$ are respectively:

$$E(W_1)=n_1(N+1)/2 \text{ and } V(W_1)=n_1 \times n_2(N+1)/12$$

It is worth noting that the above equations allow the calculation of expectation and variances of $W_1$ provided that no test values have the same rank. In such a situation, expectation and variance should be calculated by assigning an average rank to each of such test values. Such adjustments to the variance calculation are described by Hajek (Hajek (1969) A course in non parametric statistics, 2$^{nd}$ edition, New York, John Wiley & sons, Inc.).

Accordingly, the statistic Z can be defined as follows:

$$Z = \frac{W_1 - E(W_1)}{\sqrt{V(W_1)}}$$

Under the null hypothesis, i.e. the two distributions are equivalent, for an overall sample size greater than 8 (N greater than or equal to 8) Z will have a normal distribution with an expectation of 0 and a variance of 1.

For an observed value z of Z, a p-value can be derived which defines the probability that Z is greater than the observed value. A probability of less than 1%, corresponding to an observed value greater than 2.32 or less than −2.32 indicates that there is a significant difference between the random region distribution and the candidate region distribution (i.e. that the candidate genomic region is likely to contain a gene associated with the detectable trait and should be investigated further).

Alternatively, the random region distribution and the candidate region distribution may be compared to one another using the Kolmogorov-Smirnov test as follows. As described above, $n_1$ and $n_2$ are observations of a continuous variable. If $n_1$ and $n_2$ are random sets of quantities distributed according to two random variables $X_1$ and $X_2$ then the cumulative distribution functions $F_1(x)$ of $X_1$ is defined (and respectively $F_2(x)$, the cumulative function of $X_2$ is defined) as follows:

$$F_1(x)=pr(X_1<x) \text{ and } F_2(x)=pr(X_2<x)$$

where x is a value in the definition domain of $X_1$ or $X_2$ respectively.

The estimates of the two cumulative functions $F_1^*(x)$ and $F_2^*(x)$ can be calculated. For each observed x the following difference may be calculated based on the $n_1$ and $n_2$ observation sets:

$$D(x)=|F_1^*(x)-F_2^*(x)|$$

Over the N ($N=n_1+n_2$) observed values, Dmax denotes the maximum value of D(x). Based on the foregoing the following statistic was derived:

$$T = \sqrt{\frac{n_1 n_2}{(n_1 + n_2)}} D_{max}$$

Under the null hypothesis of equivalence between the two distributions, it is known that the probability of observing a value t superior to the observed value of T follows a distribution known as the Kolmogorov function (Ka(t)). Important deviations, corresponding to a probability inferior to 0.01 are considered significant (i.e. the candidate genomic region is likely to harbor a gene associated with the detectable trait). The p-value associated with the observed value of T is an indication of how the distributions are different.

Given a sample size, the Dmax value corresponding to the p-value threshold of 0.01 can easily be found as in Kim and Jenrich (*Selected tables in mathematical statistics*, Harter & Owenn eds., Chicago, Markham publishing Co., 1990), incorporated herein by reference.

Alternatively, the random region distribution and the candidate region distribution may be compared to one another using both the Wilcoxon test and the Smirnov test.

An alternative method of confirming that a genomic region harbors a gene associated with a detectable trait comprises the steps of:

constructing a candidate region distribution of test values using a plurality of biallelic markers in a candidate genomic region suspected of harboring said gene associated with said detectable trait, said candidate region distribution of test values being indicative of the difference in the frequencies of said plurality of biallelic markers in said candidate region in individuals who possess said detectable trait and control individuals who do not possess said detectable trait;

constructing a simulated distribution of test values using a plurality of biallelic markers randomly selected from biallelic markers located in random genomic regions and biallelic markers located in a candidate genomic region suspected of harboring said gene associated with said detectable trait, said simulated distribution of test values being indicative of the difference in the frequencies of said plurality of biallelic markers in said random genomic regions in individuals who possess said detectable trait and control individuals who do not possess said detectable trait; and determining whether said candidate region distribution of test values and said simulated distribution of test values are significantly different from one another.

Preferably said step of constructing a candidate region distribution of test values comprises:

performing a haplotype analysis on each possible combination of biallelic markers in each group in a series of groups of biallelic markers in said candidate region;

calculating test values for each possible combination; and including the test value for the haplotype which has the greatest association with said trait in said candidate region distribution of test values for each group in said series of groups of biallelic markers in said candidate genomic region, and wherein said step of constructing a simulated distribution of test values comprises:

assigning each of said biallelic markers in said candidate genomic region and each of said biallelic markers in said random genomic regions an identification number;

defining groups of biallelic markers by randomly selecting combinations of identification numbers using a random number generator wherein the markers assigned the selected identification numbers are included in said groups;

performing a haplotype analysis on each possible combination of biallelic markers in each group in a series of groups of biallelic markers which have been assigned identification numbers;

calculating test values for each possible combination; and including the test value for the haplotype which has the greatest association with said trait in said simulated distribution of test values for each group in said series of groups of biallelic markers.

Examples 20–23 below exemplify the application of the present method to the candidate genomic region harboring the gene associated with prostate cancer. All of the analyses below were performed using the NPAR1WAY procedure of the SAS program (SAS Institute Inc. (1996) SAS/STAT User's Guide VolII. Release 6.12, Ed. Cary, N.C., U.S.A., the disclosure of which is incorporated herein by reference).

If the candidate genomic region is found likely to harbor a gene associated with the detectable trait after the above analysis, it is evaluated further to isolate the gene which is responsible for the trait. Those skilled in the art are familiar with techniques for isolating the trait-associated gene. Essentially, the sequence of the candidate genomic region is determined and genes lying therein are identified using software which identifies open reading frames, introns and exons, homologies to known protein sequences or known nucleic acid sequences, or homologies to known protein motifs. For example the potential gene sequences may be compared to numerous databases to identify potential exons using a set of scoring algorithms such as trained Hidden Markov Models, statistical analysis models (including promoter prediction tools) and the GRAIL neural network.

In fact, the preceding techniques were utilized to identify the protein coding sequences lying within the candidate region of example 20 and 21 suspected of harboring the gene associated with prostate cancer used in the above analysis and a single protein coding region designated the PG1 gene was identified.

Preferably, the above methods are implemented using a computer program stored on a computer.

The procedures for determining whether a particular biallelic marker, or group of biallelic markers (haplotype) are associated with a particular genetic trait are preferably automated, as described below. The automated system would comprise a combination of hardware and software that can rapidly screen through thousands, tens of thousands, or millions of potential haplotypes to determine those haplotypes that are associated with a particular genetic trait.

The automated system can be implemented through a variety of combinations of computer hardware and software. In one implementation, the computer hardware is a high-speed multi-processor computer running a well-known operating system, such as UNIX. The computer should preferably be able to calculate millions, tens of millions, billions or more possible allelic variations per second. This amount of speed is advantageous for determining the statistical significance of the various distributions of haplotypes within a reasonable period of time. Such computers are manufactured by companies such as International Business Machines, Hitachi, DEC, and Cray.

While it is envisioned that currently available personal computers using single or multiple microprocessors might also function within the parameters of the present invention, such a computer system might be too slow to generate the numbers of possible haplotype combinations necessary to carry out the methods of the present invention. However, as the efficiency and speed of microprocessor-based computer systems increases, the likelihood that a conventional personal computer would be useful for the present invention also increases.

Preferably, the software that runs the calculations for the present invention is written in a language that is designed run within the UNIX operating system. The software language can be, for example, C, C++, Fortran, Perl, Pascal, Cobol or any other well-known computer language. It should be noted that the nucleic acid sequence data will be stored in a database and accessed by the software of the present invention. These programming languages are commercially available from a variety of companies such as Microsoft, Digital Equipment Corporation, and Borland International.

In addition, the software described herein can be stored on several different types of media. For example, the software can be stored on floppy disks, hard disks, CD-ROMs, Electrically Eraseable Programable Read Only Memory, Random Access Memory or any other type of programmed storage media.

The Figures described below provide an overview of the entire process of determining whether a marker, or set of markers (haplotype), within a nucleotide sequence is actually associated with a particular trait in individuals. While most of the processes can be performed manually, it is particularly advantageous to perform many of these processes with the assistance of a computer system, as described above.

Figure 18:
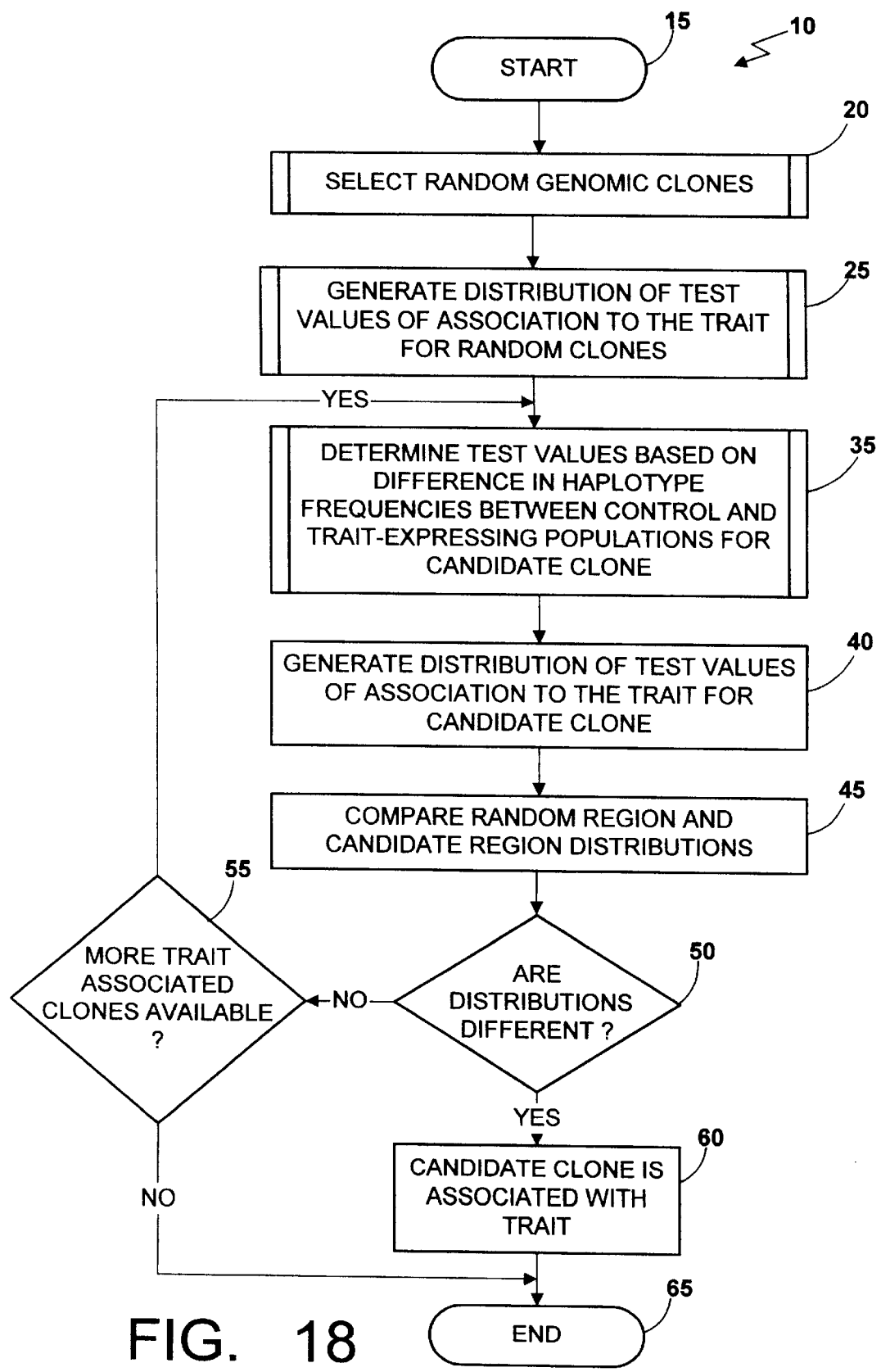
FIG. 18 is a flow diagram illustrating the process for identifying a genomic region harboring a gene associated with a detectable trait.

Referring to FIG. 18, a process 10 of determining whether a candidate clone is associated with a trait is illustrated. The process 10 begins at a start state 15 and then moves to a process state 20 wherein a set of random genomic clones are selected. These genomic clones may be chosen at random. They allow the estimation of the general frequency difference between the two groups throughout the genome. The number of genomic clones obtained is preferably at least about 30, but can be from 10 to 60 or more genomic clones. The number of clones is chosen so that the estimation of the distribution of the test statistic is accurate enough. The process 20 is described more completely with reference to FIGS. 19 and 22 below.

Once a set of random genomic clones are identified at the process state 20, the process 10 moves to a process state 25 wherein the test-value distribution of association to the trait in the random clones is generated by instructions stored in the computer. Herein, the test-values are chi-square values based on haplotype frequency differences between cases and controls. Process state 25 is described more specifically in FIG. 20 below. The distribution plot is a set of data points that, when displayed on a coordinate system, form a diagram indicating the chi-squared values for each haplotype in each of the random genomic clones. It should be noted that the distribution does not necessarily need to be generated from chi-squared values derived from haplotype frequency differences between the two groups of individuals. Any similar measurment of difference between control and trait-expressing individuals based on groups of markers found within the selected random genomic clones may be used in the present invention.

The process 10 then moves to a process state 35 wherein the test values of haplotype frequency differences between the control and trait-expressing populations within the candidate clone are determined. The process 10 then moves to a state 40 wherein the distribution of the test-values in the candidate clone is generated. Prior to the generation of the distribution of test-values, it is advantageous to "saturate" the candidate clone so that as many biallelic markers as possible are known within the clone. The number of markers in the candidate clone is preferably twenty-five or more but may be 10, 15 or 20. Once a large number of biallelic markers are known in the candidate clone, haplotypes comprising groups of three markers can be chosen at random and haplotype frequency estimations in cases and in controls can be compared by means of chi-square statistics. For one group of markers, one chi-square value (i.e. the chi squared value for the haplotype having the greatest association with the trait) is stored to a computer memory for later processing.

The data plot distribution generated in state 40 is derived from all chi-square values and the chi-squares are stored as described above. Of course, it should be understood that any other statistical mechanism for generating a distribution of test values based on haplotype frequencies or any measured observation of haplotypes is useful in the present invention. Once the distribution plot is calculated in the computer at the state 40, the process 10 moves to a state 45 wherein the distribution plots from the test values in the random clones and the test values in the candidate clone are compared. The process 45 of comparing random region distributions and candidate region distribuations is described in FIG. 24 below.

Once the distributions are compared, the process 10 moves to a decision state 50 to determine whether the distributions are different. If the random region and the candidate region distributions are determined to be different at decision state 50, the process moves to a decision state 55 wherein a determination is made whether more trait associated clones are available. If more trait associated clones are available, the process 10 returns to the state 35. However, if no more trait associated clones are available, the process 10 terminates at an end state 65.

If a determination is made at the state 50 that the distributions are different, the process 10 moves to a state 60 wherein the computer system indicates that the candidate clone was found to be effectively associated to the studied trait. This indication can be through computer's display, printer or any other well-known mechanism for notifying a computer user of the results of a particular process. The process then terminates at the end state 65.

Figure 25:
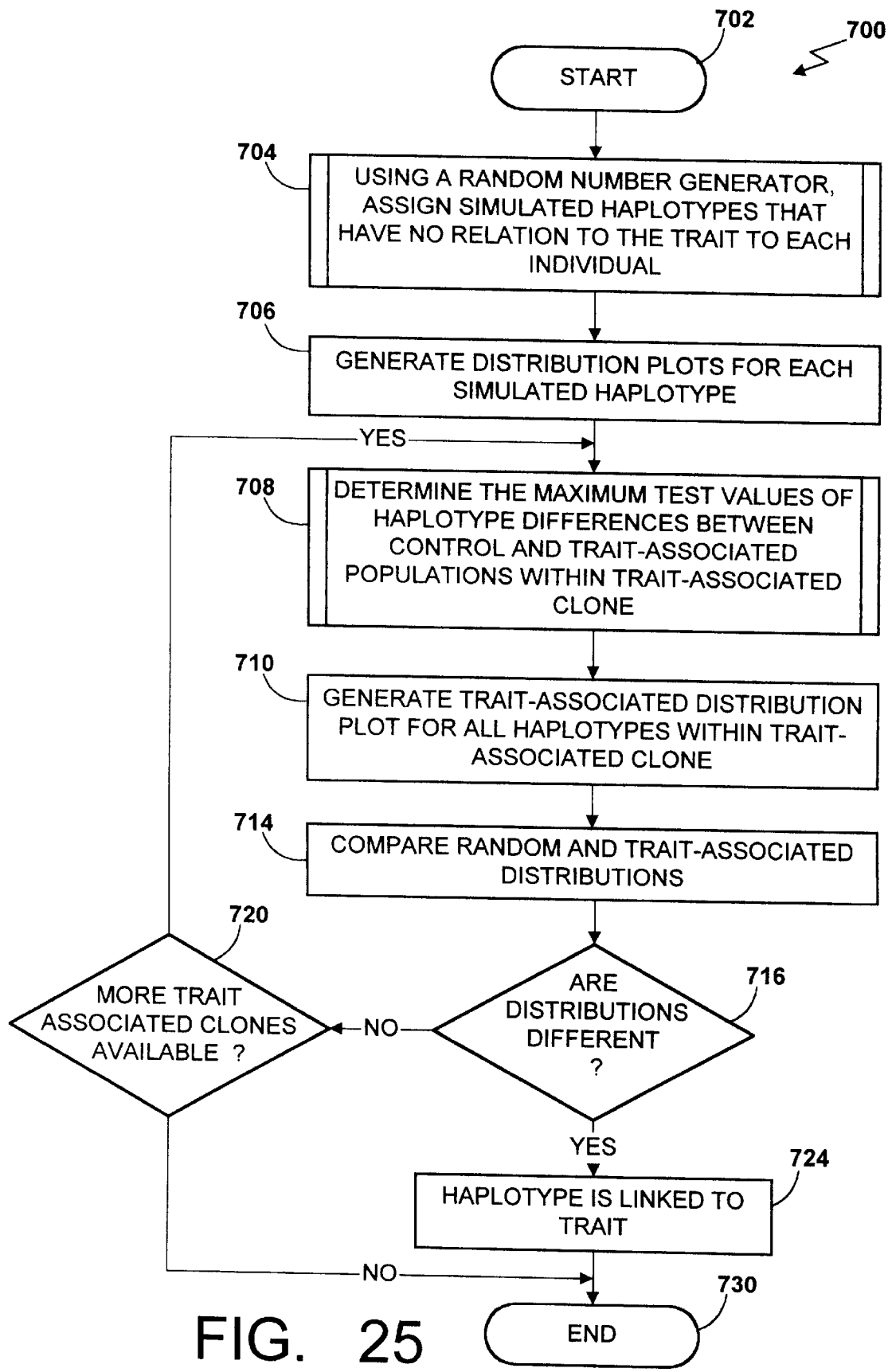
FIG. 25 is a flow diagram illustrating the process for identifying a genomic region harboring a gene associated with a detectable trait.

As one alternative, the process 10 of FIG. 18 can be altered as shown in FIG. 25 below. Referring to FIG. 25, a process 700 of determining whether an individual biallelic marker or set of biallelic markers (haplotype) is linked to a particular trait is described. The process 700 begins at a start state 702 and then moves to a process state 704 wherein, using a random number generator, the simulated haplotypes that have no relation to the trait are assigned to each individual.

The process 700 then moves to a state 706 wherein the test-value distribution of each of the simulated haplotypes is generated by instructions stored in the computer. Herein, the test-values are chi-square values based on haplotype frequency differences between cases and controls. The distribution plot is a set of data points that, when displayed on a coordinate system, form a diagram indicating the chi-squared values for each haplotype in each of the random genomic clones. It should be noted that the distribution plot does not necessarily need to be generated from frequencies derived from chi-squared values. Any similar measurement of a statistical difference between control and trait-associated individuals having the haplotypes found within the selected random genomic clones may be used within the present invention.

The process 700 then moves to a state 708 wherein the maximum test values of haplotype differences between the control and trait-associated populations within the trait-associated clone is determined. The process 700 then moves to a state 710 wherein the distribution of the test-value in the trait-associated clone is generated. Prior to the generation of the distribution of test-value, it is advantageous to "saturate" the trait-associated clone so that as many biallelic markers as possible are known within the clone.

The number of markers in the trait-associated clone is preferably twenty-five or more but may be 10, 15 or 20. Once a large number of biallelic markers are known in the trait-associated clone, haplotypes comprising groups of three markers can be chosen at random and haplotype frequency estimations in cases and in controls can be compared by means of chi-square statistics. For one group of markers, one chi-square value (i.e. the chi squared value for the haplotype having the greatest association with the trait) is stored to a computer memory for later processing.

The data plot distribution generated in state 710 is derived from all chi-square values and the chi-squares are stored as described above. Of course, it should be understood that any other statistical mechanism for generating a distribution of test values based on haplotype frequencies or any measured observation of haplotypes is useful in the present invention. Once the distribution plot is calculated in the computer at the state 710, the process 700 moves to a state 714 wherein the distribution plots from the haplotypes in the random clones and the haplotypes in the trait-associated clone are compared.

Once the distributions are compared, the process 700 moves to a decision state 716 to determine whether the distributions are different. If the random and the trait-associated distributions are not determined to be different at decision state 716, the process moves to a state 720 wherein a determination is made whether more trait-associated clones are available. If more trait-associated clones are available, the process 700 returns to the state 708. However, if no more trait-associated clones are available, the process 700 terminates at an end state 730.

If a determination is made at the state 716 that the distributions are different, the process 700 moves to a state 724 wherein the computer system indicates that the suspected trait-associated clone was found to be effectively associated to the studied trait. This indication can be through computer's display, printer or any other well-known mechanism for notifying a computer user of the results of a particular process. The process then terminates at the end state 730.

Figure 19:
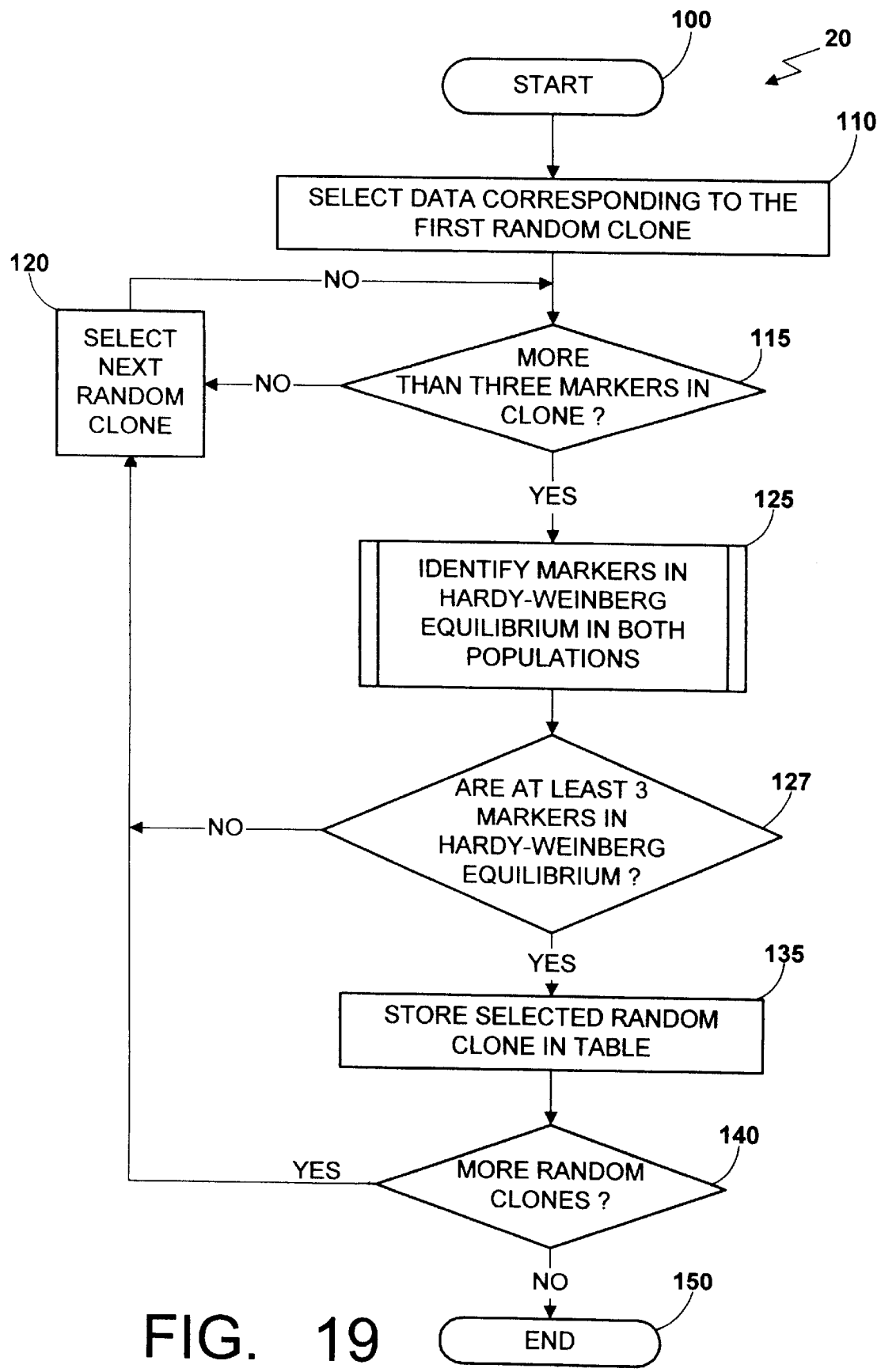
FIG. 19 illustrates a process for identifying random genomic clones.

Referring now to FIG. 19, the process 20 of identifying suitable random genomic clones is illustrated. The process 20 begins at a start state 100 and then moves to a state 110 wherein data representing a DNA sequence corresponding to the first random clone to be analyzed is selected. Normally, this data is stored on the hard disk of the computer. However, it should be noted that this data can be stored in any conventional memory within the computer system or outside the computer on a server or other data storage computer.

The data representing the DNA sequence is preferably derived from nucleotide sequencing of a bacterial artificial chromosome (BAC). However, the data can be derived from the nucleotide sequence of any type of clone that carries DNA sequences.

Once data representing the first random clone is selected at the state 110, the process 20 moves to a decision state 115 wherein a determination is made whether there are more than three biallelic markers within the clone. Prior to performing this process, the data representing the DNA sequence is matched against several databases of genes to determine whether any biallelic markers exist within the sequence. If any biallelic markers do exist, that data is held in a marker table on the computer. The marker table holds the name of each file corresponding to nucleic acid sequence data from a random clone and the description of any biallelic markers within the DNA sequence. Through the marker table, one can access the number of biallelic markers in the data corresponding to each random and candidate clone.

At the decision state 115, a determination is made by reference to the marker table whether more than three biallelic markers are found in the data from the selected clone. If more than three markers are not found in the clone, the process 20 moves to a state 120 wherein the next random clone is selected since this clone does not have enough biallelic markers for an efficient analysis. Following the state 120, the process 20 then returns to the decision state 115 to determine if more than three biallelic markers are available in the nucleic acid sequence data from newly selected clone.

If more than three markers are found in the clone, the process 20 moves to a process state 125 where markers that are in Hardy-Weinberg equilibrium in case and control populations are identified. Process 125 is described in FIG. 22 below. Process 20 then moves to a decision state 127 to determine if there are at least three markers in Hardy-Weinberg equilibrium in both populations. If there are not at least three markers in H-W equilibrium, the process returns to state 120 to select another random clone. If there are at least three markers in H-W equilibrium, process 20 moves to a state 135 wherein the selected random clone is stored to a random clone table on the computer's hard disk.

The process 20 then moves to a decision state 140 to determine whether more random clones exist that need to be analyzed. As described above, it is advantageous to have at least 25 random clones with biallelic markers to be used as chi-squared data points in the distribution plot. If more random clones do exist, the process 20 returns to the state 120 to select the data from the nucleotide sequence of the next random clone. If no more data is available for nucleotide sequences of random clones at the decision state 140, the process 20 terminates at an end state 150.

Figure 22:
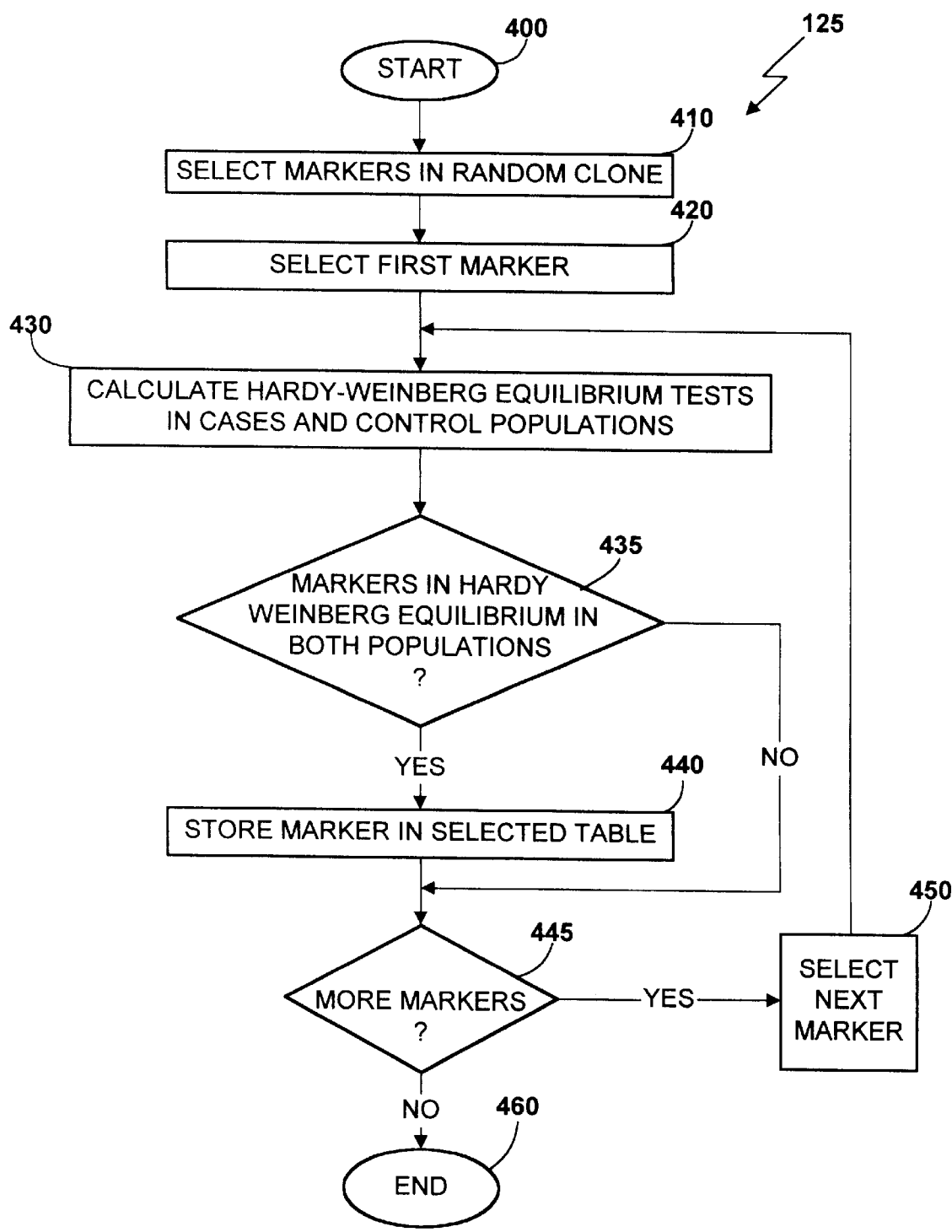
FIG. 22 illustrates the process for identifying markers in random clones which are in H-W equilibrium in the case and control populations.

Now referring to FIG. 22, the process 125 of identifying markers in Hardy-Weinberg equilibrium in case and control populations (FIG. 19) is described in more detail. The process 125 begins at start state 400 and moves to a state 410 where the markers in the random clone are selected from the table described above. The process 125 then moves to a state 420 where the first marker is selected. The process 125 then moves to state 430 wherein the Hardy-Weinberg equilibrium calculations are performed in cases and in control populations as described above.

Once the test calculations in cases and in control populations are performed at state 430, the process 125 moves to a decision state 435 to determine whether the selected marker is in Hardy-Weinberg equilibrium in both populations. If a determination is made at decision state 435 that the marker is in Hardy-Weinberg equilibrium in both populations, the process 125 moves to state 440 where the marker is stored in a table. The process then moves to a decision state 445 to determine whether there is another marker in the clone.

If a determination is made at decision state 435 that the marker is not in Hardy-Weinberg equilibrium in one or the other population, the process 125 moves directly to state 445 to determine whether more markers are available in the clone.

If a determination is made at decision state 445 that other markers are available for testing in the clone, the process 125 moves to state 450 where another marker is selected. The process 125 then returns to state 430. If a determination is made at decision state 445 that all markers were tested for Hardy-Weinberg equilibrium, the process 125 ends at an end state 460.

Figure 20:
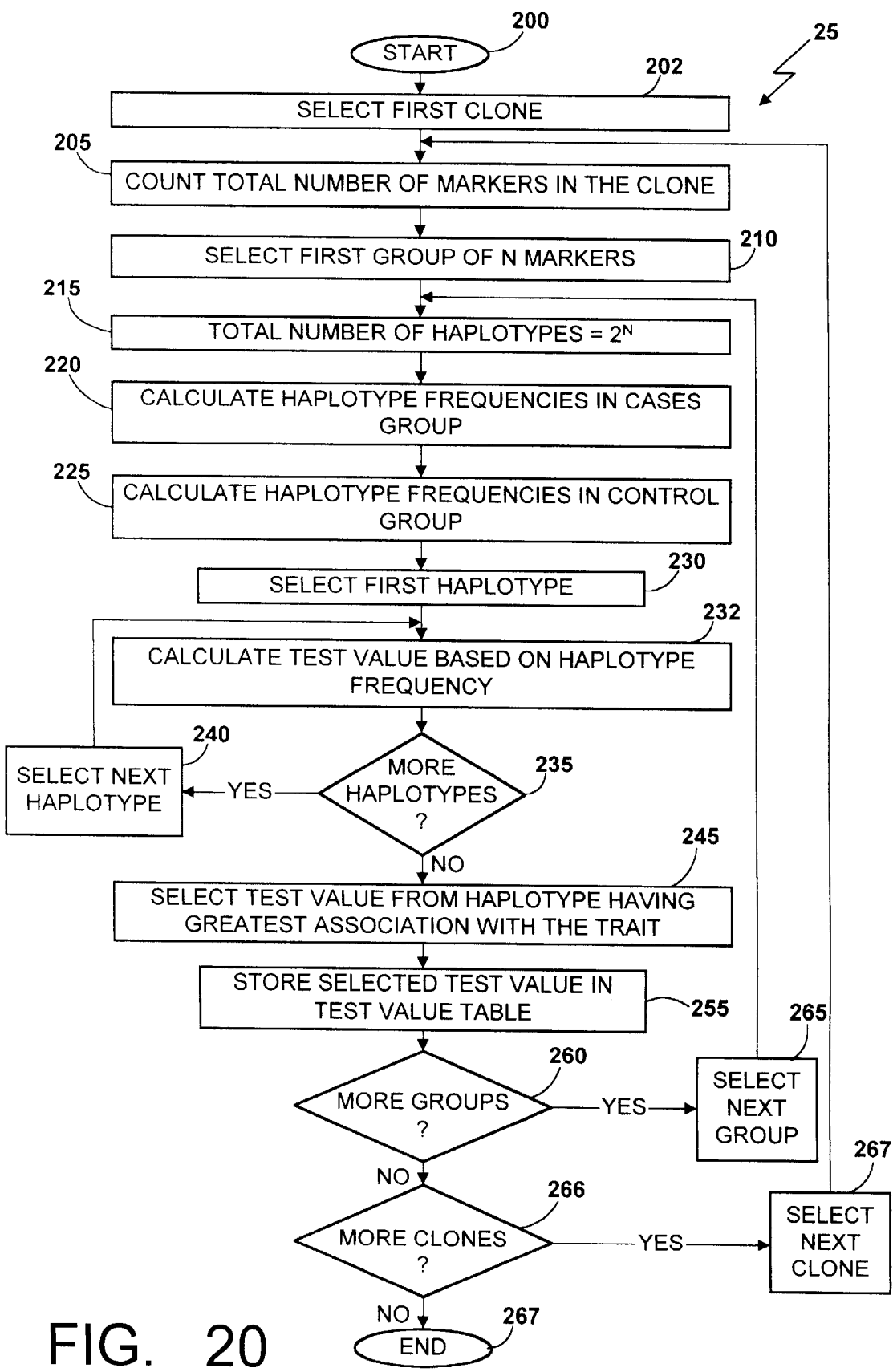
FIG. 20 illustrates a process for determining the test values of haplotype frequency differences between control and trait-associated populations within random clones.

Referring now to FIG. 20, the process 25 of generating the distribution of test-values in selected random clones begins at a start state 200 and moves to state 202 where the first clone is selected. The process moves to state 205 where the total number of markers in Hardy-Weinberg equilibrium in both case and control populations is counted. Once the total number of available markers is counted in state 205, the process 25 moves to state 210 where the first group of N markers is selected.

In one embodiment, N=3 so that each group of markers is analyzed as a triplet. In this embodiment, each haplotype comprises a group of three biallelic markers. However, it should be noted that each group could consist of either more or less markers. In one embodiment, a haplotype comprising only two markers is selected instead of a group of three or more associated markers. In another embodiment, a group of eight markers is selected for further analysis.

The process 25 then moves to a state 215 wherein the total number of possible haplotypes based on the total number N of markers within the first group is determined. The formula $2^N$ can be used to determine all of the possible haplotypes in a group of N markers. This formula is correct since, given any set of N biallelic markers, there are $2^N$ possible rearrangements of those markers on a nucleic acid sequence.

Once the total number of haplotypes is calculated in state 215, the process 25 moves to state 220 wherein haplotype frequencies in the cases group are estimated using the E-M algorithm as described above. When the $2^N$ haplotype frequencies are estimated in the cases group in state 220, the process 25 moves to state 225 wherein the $2^N$ haplotype frequencies are estimated in the control group using the same algorithm.

Once the haplotype frequencies are estimated in both groups, the process 25 moves to a state 230 wherein the first haplotype is selected. The process 25 then moves to state 232, wherein the chi-square test value based on haplotype frequency difference between the cases and control groups is calculated.

Once the chi-square statistic is calculated, the process 25 then moves to a decision state 235 to determine whether more haplotypes exist for the selected random clone. If a determination is made that more haplotypes do exist at the decision state 235, the process 25 moves to a state 240 to select the next haplotype. It should be noted that in every group of three biallelic markers there are $2^3$, or eight, possible haplotypes. Thus, this process will be repeated eight times for every group of three markers until each of the eight possible haplotypes is aligned with nucleic acid sequences from each of the control and trait-associated clones. If there are more haplotypes left to analyze in the selected group, the process 25 returns to state 232 to calculate the chi-square based on a difference in haplotype frequencies.

If a determination is made at the decision state 235 that the frequencies of all of the possible haplotypes in the selected group have been determined in the control and trait expressing populations, the process 25 moves to a state 245 to select the test value for the haplotype in the group with the greatest association with the selected trait. This analysis is described above, but is preferably carried out using a chi-squared test to compare the frequency of each haplotype in the control and trait expressing groups. The chi-squared test gives a value reflective of how tightly associated the individual haplotype is with the trait. The chi squared value from the haplotype in the group that has the greatest association with the trait is then stored at a state 255 to a test value table on the computer's had disk. Thus, for each group of biallelic markers, one chi squared value from the haplotype having the greatest association with the trait is chosen for inclusion in the test value table. This procedure is done in order to follow the procedures done with the trait-associated clone.

Once the selected chi squared value is stored to the test value table at the state 255, the process moves to a decision state 260 to determine whether more groups of, for example, sets of three biallelic markers exist in the selected clone to be analyzed. If more groups do exist in the nucleotide sequence of the selected clone, the process 25 moves to a state 265 and selects the next group of three markers. The process 25 then returns to the state 215 to determine the total number of haplotypes within the newly selected group. If a determination is made at decision state 260 that all groups of markers have been analyzed in the random clone, the process 25 moves to a decision state 266 to determine whether there are more clones available in the marker table stored in the computer. If more clones do exist, the process 25 moves to state 267 in order to select the next clone. The process 25 then returns to state 205 where the total number of markers in Hardy-Weinberg equilibrium in the selected clone is counted. If a determination is made at decision state 266 that no more clones are available in the marker table, the process 25 terminates at an end state 270.

Figure 21:
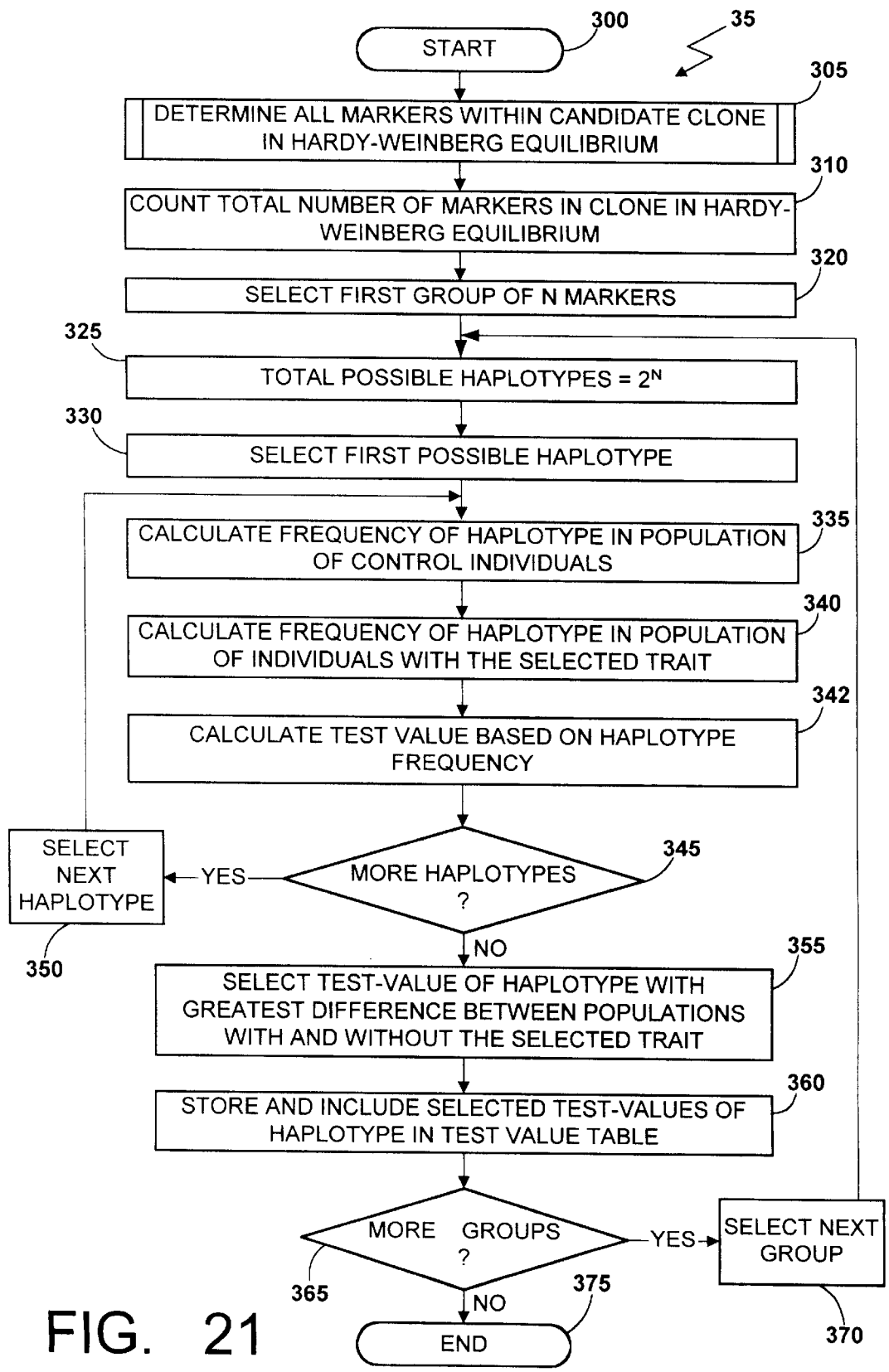
FIG. 21 illustrates a process for determining the test values of haplotype frequency differences between control and trait associated populations within a candidate clone.

Referring now to FIG. 21, the process 35 (FIG. 18) of calculating the test values in the candidate clone is described in more detail. The process 35 begins a start state 300 and moves to a process state 305 wherein the total number of biallelic markers in Hardy-Weinberg equilibrium in case and control groups in the candidate clone is determined. The process 105 is described in more detail in FIG. 23. The process 35 then counts the total number of markers in Hardy-Weinberg equilibrium at a state 310. It should be noted that determining the number of markers in Hardy-Weinberg equilibrium is advantageous because the method used to infer haplotype frequencies in the two populations studied (cases and controls) rely on this assumption, i.e. that the markers involved in the haplotype fit the Hardy-Weinberg equilibrium, as described above. The number of markers is preferably retrieved from a table that has been previously created to store the location of each marker within the trait-associated sequence.

The process 35 then moves to a state 320 wherein the first group of N markers is selected. In one embodiment, N=3 so that each group of markers that is analyzed as a triplet. In this embodiment, each haplotype comprises a group of three biallelic markers. However, it should be noted that each group could consist of either more or less markers.

The process 35 then moves to a state 325 wherein the total number of possible haplotypes based on the total number N of markers within the first group is determined. The formula $2^N$ can be used to determine all of the possible haplotypes in a group of N markers. This formula is correct since, given any set of N biallelic markers, there are $2^N$ possible combinations of those markers on a nucleic acid sequence.

Once the number of markers in Hardy-Weinberg equilibrium is determined in both populations, the process 35 moves to state 330 wherein the first possible haplotype is selected. The process 35 then moves to a state 335 wherein the haplotype frequencies are estimated in the control group using the E-M algorithm as described above. Once the haplotype frequencies are estimated in the control group, the process 35 moves to state 340, where the haplotype frequencies are estimated in the population of individuals with the selected trait.

Once the haplotype frequencies are estimated in both populations at study in states 335 and 340, the process 35 moves to state 342, wherein a chi-square statistic based on the differences in haplotype frequencies is computed.

Once this calculation is made, the process 35 then moves to a decision state 345 to determine whether more haplotypes exist for the candidate clone. If a determination is made that more haplotypes do exist at the decision state 345, the process 35 moves to a state 350 to select the next haplotype.

It should be noted that in every group of three biallelic markers there are $2^3$ or eight possible haplotypes. Thus, this process will be repeated eight times for every group of three markers until the frequencies of each of the eight possible haplotypes is determined in the control and case populations. If here are more haplotypes left to analyze in the selected group, the process 35 returns to the state 335 to calculate the frequency of the next haplotype of the group in the population of control individuals.

If a determination is made at the decision state 345 that the frequencies of all of the possible haplotypes in the selected group have been determined in the control and case populations, the process 35 moves to a state 355 to select the test value from the haplotype in the group with the greatest association with the selected trait. This analysis is described above, but is preferably carried out using a chi-squared test to determine the frequency difference of each haplotype in the control and case populations.

The chi-squared test gives a value reflective of how tightly associated the individual haplotype is with the trait. The chi squared value from the haplotype in the group that has the greatest association with the trait is then stored at a state 360 to a test value table on the computer's hard disk. Thus, one chi squared value from the haplotype having the greatest association with the trait is chosen.

Once the selected chi squared value is stored to the test value table at the state 360, the process moves to a decision state 365 to determine whether more groups of, for example, sets of three biallelic markers exist in the candidate clone to be analyzed. If more groups do exist in the candidate clone, the process 35 moves to a state 370 and selects the next group of three markers. The process 35 then returns to the state 325 to determine the total number of haplotypes within the newly selected group. If a determination is made at the decision state 365 that no more groups exist, the process 35 terminates at an end state 375.

Figure 23:
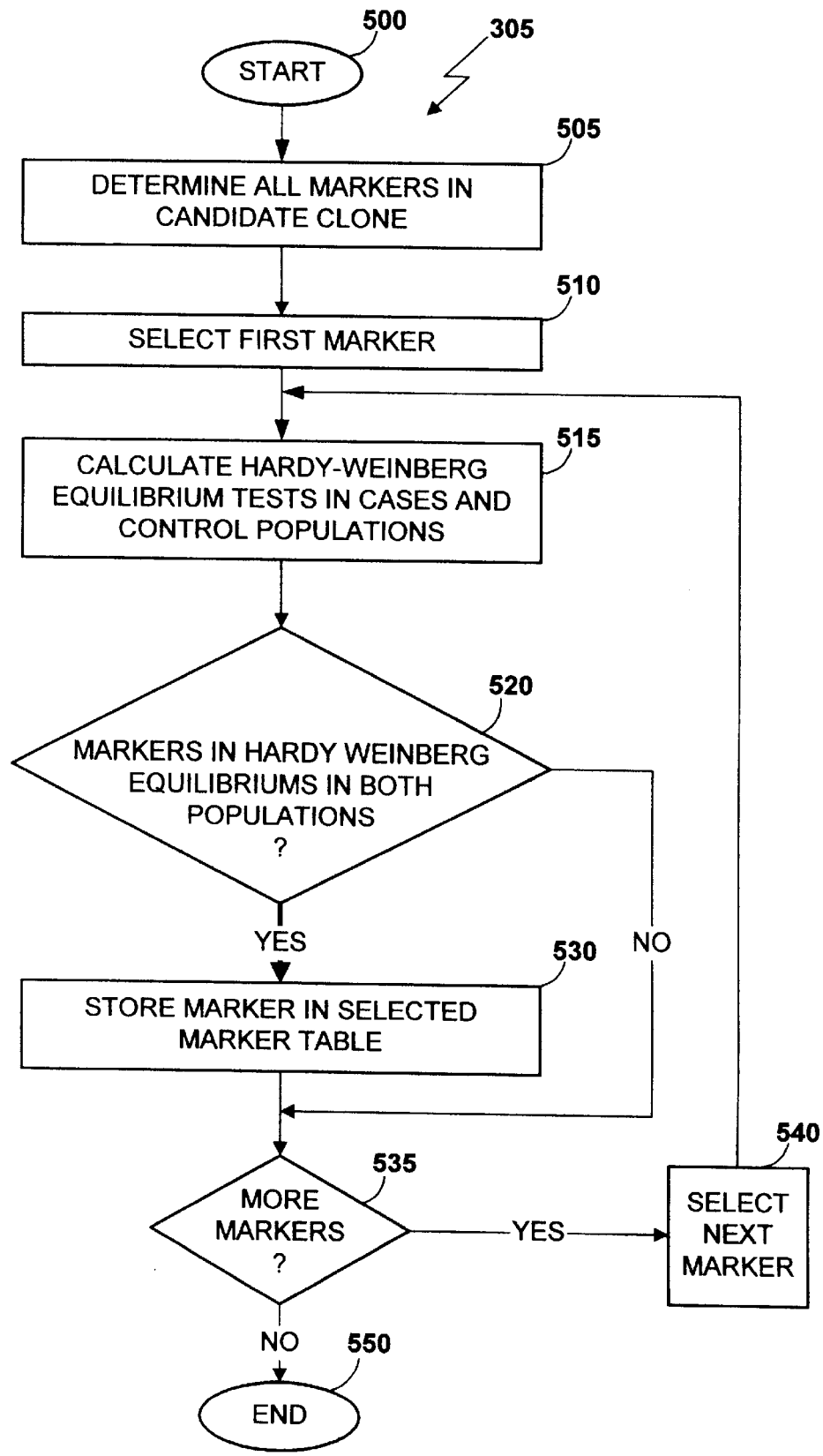
FIG. 23 illustrates the process for identifying markers in candidate clones which are in H-W equilibrium in the case and control populations.

Referring now to FIG. 23, the process 305 of determining the number of markers within the candidate clone that are in Hardy-Weinberg equilibrium in both case and control populations is described in more detail. The process 305 begins at a start state 500 and moves to state 505 where all markers in the candidate clone are counted from a marker table stored in the computer. Once the number of markers available is determined, the process 305 moves to state 510 where the first marker is selected. It then moves to state 515 wherein the Hardy-Weinberg equilibrium is calculated in case and in control populations for this marker. This test allows determination of whether the assumption of random mating as described above fits for this particular marker in the two populations at study. This step involves a chi-square statistical computation.

Once the Hardy-Weinberg equilibrium is computed in both case and control populations at state 515, the process 305 moves to decision state 520 to determine whether the marker fits the hypothesis of Hardy-Weinberg equilibrium in both populations. If a determination is made that the marker fits this hypothesis, the process 305 moves to state 530 where the marker is stored to a table. The process 305 then moves then to a decision state 535 to determine whether there are other available markers for Hardy-Weinberg testing.

If a determination is made at the decision state 520 that the marker does not fit the hypothesis of Hardy-Weinberg equilibrium, the process 305 moves to the decision state 535.

At the decision state 535, if a determination is made that other markers are available for testing, the process 305 moves to state 540 to select the next marker. The process 305 then returns to state 515 to calculate Hardy-Weinberg equilibriums for the selected marker. If a determination is made at decision state 535 that all markers available in the clone have been tested for Hardy-Weinberg equilibrium, the process 305 ends at an end state 550.

It should be noted that the determination of a Hardy-Weinberg equilibrium is advantageous because the method of estimation of haplotype frequencies relies on this hypothesis. However, if any other haplotype frequency estimation algorithm, relying on other assumptions, is used other selection processes based on such assumptions may be used.

Figure 24:
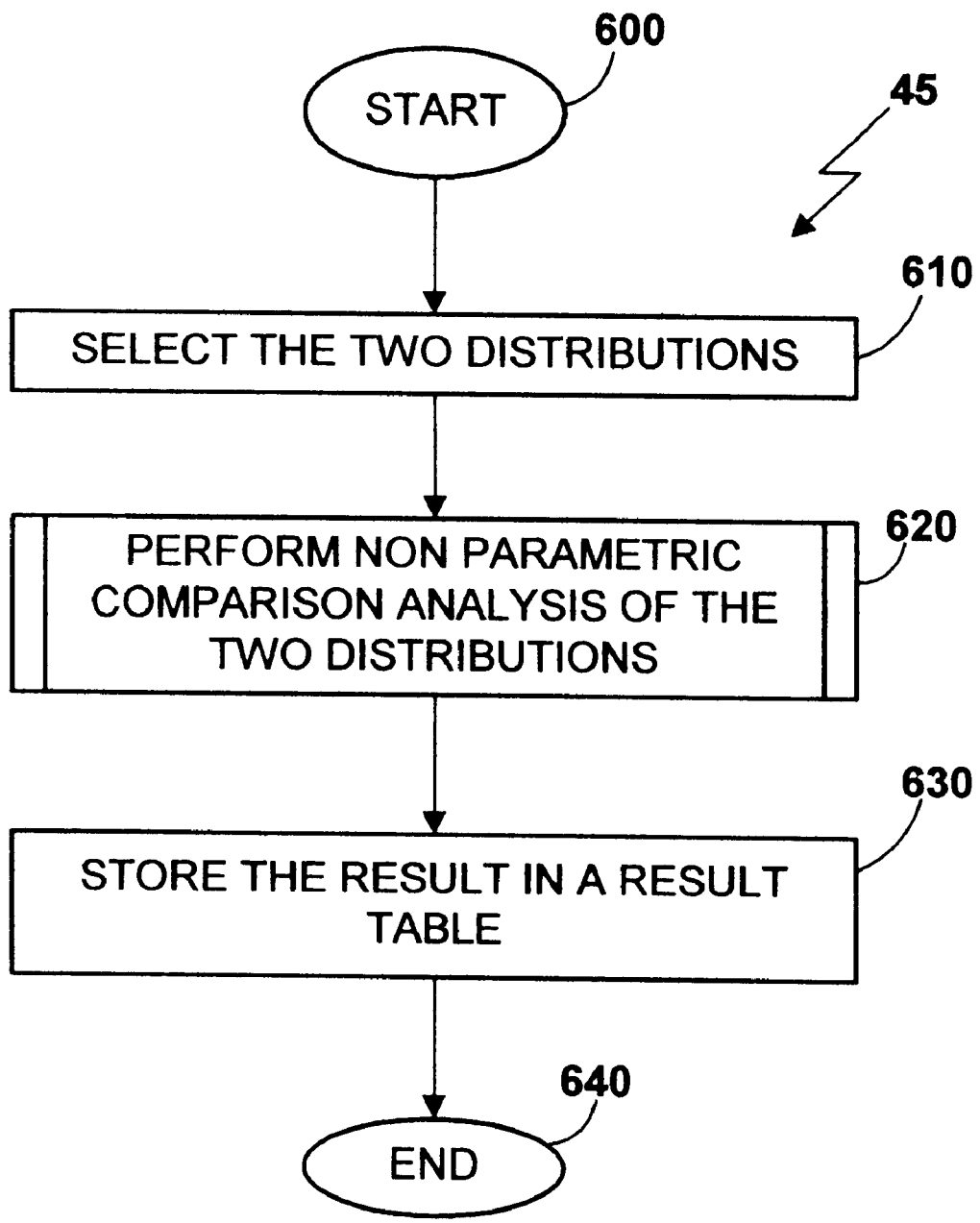
FIG. 24 illustrates the process for comparing the two distributions of test values.

Referring to FIG. 24, the two distributions of test-values are compared in the random clone and the candidate clone. The process 45 begins at a start state 600 and moves to state 610 where the two distributions are selected from the two test-values tables mentioned above. The process 45 then moves to a state 620 wherein a non parametric analysis is performed to compare these two distributions.

The two distributions can be compared using any method that is familiar to one of ordinary skill in the art. For example, a computer program can apply either the Wilcoxon rank test or the Kolmogorov-Smirnov test, which are discussed above. These software programs would simply apply either of the formulas to the data derived above relating to the statistical difference between particular haplotypes found in control and trait-associated individuals.

The process 45 then moves to state 630 where the results of the analysis are stored in a result table. The results can then be printed through a computer display, printer or any other well-known mechanism for notifying a result of a particular process. The process 630 then ends at an end state 640.

Several of the aspects of the present invention are described in the following examples, which are offered by way of illustration and not by way of limitation. Many other modifications and variations of the invention as herein set forth can be made without departing from the spirit and scope thereof and therefore only such limitations should be imposed as are indicated by the appended claims.

EXAMPLE 1

Construction of a BAC Library

Three different human genomic DNA libraries were produced by cloning partially digested DNA from a human lymphoblastoid cell line (derived from individual No. 8445, CEPH families) into the pBeloBAC11 vector (Kim et al., *Genomics* 34:213–218 (1996), the disclosure of which is incorporated herein by reference). One library was produced using a BamHI partial digestion of the genomic DNA from the lymphoblastoid cell line and contains 110,000 clones having an average insert size of 150 kb (corresponding to 5 human haploid genome equivalents). Another library was prepared from a HindIII partial digest and corresponds to 3 human genome equivalents with an average insert size of 150 kb. A third library was prepared from a NdeI partial digest and corresponds to 4 human genome equivalents with an average insert size of 150 kb.

Alternatively, the genomic DNA may be inserted into BAC vectors which possess both a high copy number origin of replication, which facilitates the isolation of the vector DNA, and a low copy number origin of replication. Cloning of a genomic DNA insert into the high copy number origin of replication inactivates the origin such that clones containing a genomic insert replicate at low copy number. The low copy number of clones having a genomic insert therein permits the inserts to be stably maintained. In addition, selection procedures may be designed which enable low copy number plasmids (i.e. vectors having genomic inserts therein) to be selected. Such vectors and selection procedures are described in U.S. patent application Ser. No. 09/058,746 entitled "High Throughput DNA Sequencing Vector", the entire contents of which are incorporated herein by reference.

It will be appreciated that the present methods may be practiced using BAC vectors other than those of Shizuya et al. (1992, supra), or derived from those, or vectors other than BAC vectors which possess the above-described characteristics.

EXAMPLE 2

Ordering of a BAC Library: Screening Clones with STSs

The BAC library is screened with a set of PCR-typeable STSs to identify clones containing the STSs. To facilitate PCR screening of several thousand clones, for example 200,000 clones, pools of clones are prepared.

Three-dimensional pools of the BAC libraries are prepared as described in Chumakov et al. and are screened for the ability to generate an amplification fragment in amplification reactions conducted using primers derived from the ordered STSs. (Chumakov et al. (1995), supra). A BAC library typically contains 200,000 BAC clones. Since the average size of each insert is 100–300 kb, the overall size of such a library is equivalent to the size of at least about 7 human genomes. This library is stored as an array of individual clones in 518 384-well plates. It can be divided into 74 primary pools (7 plates each). Each primary pool can then be divided into 48 subpools prepared by using a three-dimensional pooling system based on the plate, row and column address of each clone (more particularly, 7 subpools consisting of all clones residing in a given microtiter plate; 16 subpools consisting of all clones in a given row; 24 subpools consisting of all clones in a given column).

Amplification reactions are conducted on the pooled BAC clones using primers specific for the STSs. For example, the three dimensional pools may be screened with 45,000 STSs whose positions relative to one another and locations along the genome are known. Preferably, the three dimensional pools are screened with about 30,000 STSs whose positions relative to one another and locations along the genome are known. In a highly preferred embodiment, the three dimensional pools are screened with about 20,000 STSs whose positions relative to one another and locations along the genome are known.

Amplification products resulting from the amplification reactions are detected by conventional agarose gel electrophoresis combined with automatic image capturing and processing. PCR screening for a STS involves three steps: (1) identifying the positive primary pools; (2) for each positive primary pool, identifying the positive plate, row and column 'subpools' to obtain the address of the positive clone; (3) directly confirming the PCR assay on the identified clone. PCR assays are performed with primers specifically defining the STS.

Screening is conducted as follows. First BAC DNA containing the genomic inserts is prepared as follows. Bacteria containing the BACs are grown overnight at 37° C. in 120 $\mu$l of LB containing chloramphenicol (12 $\mu$g/ml). DNA is extracted by the following protocol:

Centrifuge 10 min at 4° C. and 2000 rpm

Eliminate supernatant and resuspend pellet in 120 $\mu$l TE 10-2 (Tris HCl 10 mM, EDTA 2 mM)

Centrifuge 10 min at 4° C. and 2000 rpm

Eliminate supernatant and incubate pellet with 20 $\mu$l lyzozyme 1 mg/ml during 15 min at room temperature Add 20 $\mu$l proteinase K 100 $\mu$g/ml and incubate 15 min at 60° C.

Add 8 $\mu$l DNAse 2 U/$\mu$l and incubate 1 hr at room temperature

Add 100 $\mu$l TE 10-2 and keep at −80° C.

PCR assays are performed using the following protocol:

| | |
|---|---|
| Final volume | 15 $\mu$l |
| BAC DNA | 1.7 ng/$\mu$l |
| MgCl$_2$ | 2 mM |
| dNTP (each) | 200 $\mu$M |
| primer (each) | 2.9 ng/$\mu$l |
| Ampli Taq Gold DNA polymerase | 0.05 unit/$\mu$l |
| PCR buffer (10x = 0.1 M TrisHCl pH 8.3 0.5 M KCl | 1x |

The amplification is performed on a Genius II thermocycler. After heating at 95° C. for 10 min, 40 cycles are performed. Each cycle comprises: 30 sec at 95° C., 54° C. for 1 min, and 30 sec at 72° C. For final elongation, 10 min at 72° C. end the amplification. PCR products are analyzed on 1% agarose gel with 0.1 mg/ml ethidium bromide.

EXAMPLE 3

Subcloning of BACs

The cells obtained from three liters overnight culture of each BAC clone are treated by alkaline lysis using conventional techniques to obtain the BAC DNA containing the genomic DNA inserts. After centrifugation of the BAC DNA in a cesium chloride gradient ca. 50 $\mu$g of BAC DNA are purified. 5–10 $\mu$g of BAC DNA are sonicated using three distinct conditions, to obtain fragments within a desired size range. The obtained DNA fragments are end-repaired in a 50 $\mu$l volume with two units of Vent polymerase for 20 min at 70° C., in the presence of the four deoxytriphosphates (100 $\mu$M). The resulting blunt-ended fragments are separated by electrophoresis on preparative low-melting point 1% agarose gels (60 Volts for 3 hours). The fragments lying within a desired size range, such as 600 to 6,000 bp, are excised from the gel and treated with agarase. After chloroform extraction and dialysis on Microcon 100 columns, DNA in solution is adjusted to a 100 ng/$\mu$l concentration. A ligation to a linearised, dephosphorylated, blunt-ended plasmid cloning vector is performed overnight by adding 100 ng of BAC fragmented DNA to 20 ng of pBluescript II Sk (+) vector DNA linearized by enzymatic digestion, and treating with alkaline phosphatase. The ligation reaction is performed in a 10 $\mu$l final volume in the presence of 40 units/$\mu$l T4 DNA ligase (Epicentre). The ligated products are electroporated into the appropriate cells (ElectroMAX *E.coli* DH10B cells). IPTG and X-gal are added to the cell mixture, which is then spread on the surface of an ampicillin-containing agar plate. After overnight incubation at 37° C., recombinant (white) colonies are randomly picked and arrayed in 96 well microplates for storage and sequencing.

Alternatively, BAC subcloning may be performed using vectors which possess both a high copy number origin of replication, which facilitates the isolation of the vector DNA, and a low copy number origin of replication. Cloning of a genomic DNA fragment into the high copy number origin of replication inactivates the origin such that clones containing a genomic insert replicate at low copy number. The low copy number of clones having a genomic insert therein permits the inserts to be stably maintained. In addition, selection procedures may be designed which enable low copy number plasmids (i.e. vectors having genomic inserts therein) to be selected. In a preferred embodiment, BAC subcloning will be performed in vectors having the above described features and moreover enabling high throughput sequencing of long fragments of genomic DNA. Such high throughput high quality sequencing may be obtained after generating successive deletions within the subcloned fragments to be sequenced, using transposition-based or enzymatic systems. Such vectors are described in the U.S. patent application Ser. No. 09/058,746.

It will be appreciated that other subcloning methods familiar to those skilled in the art may also be employed.

The resulting subclones are then partially sequenced using, for example, the procedures described below.

EXAMPLE 4

Partial Sequencing of BAC Subclones

The genomic DNA inserts in the subclones, such as the BAC subclones prepared above, are amplified by conducting PCR reactions on the overnight bacterial cultures, using primers complementary to vector sequences flanking the insertions.

The sequences of the insert extremities (on average 500 bases at each end, obtained under routine sequencing conditions) are determined by fluorescent automated sequencing on ABI 377 sequencers, using ABI Prism DNA Sequencing Analysis software. Following gel image analysis and DNA sequence extraction, sequence data are automatically processed with adequate software to assess sequence quality. A proprietary base-caller, automatically flags suspect peaks, taking into account the shape of the peaks, the inter-peak resolution, and the noise level. The proprietary base-caller also performs an automatic trimming. Any stretch of 25 or fewer bases having more than 4 suspect peaks is usually considered unreliable and is discarded.

The sequenced regions of the subclones, such as the BAC subclones prepared above, are then analyzed in order to identify biallelic markers lying therein. The frequency at which biallelic markers will be detected in the screening process varies with the average level of heterozygosity desired. For example, if biallelic markers having an average heterozygosity rate of greater than 0.42 are desired, they will occur every 2.5 to 3 kb on average. Therefore, on average, six 500 bp-genomic fragments have to be screened in order to derive 1 biallelic marker having an adequate informative content.

As a preferred alternative to sequencing the ends of an adequate number of BAC subclones, the above mentioned high throughput deletion-based sequencing vectors, which allow the generation of a high quality sequence information covering fragments of ca. 6 kb, may be used. Having sequence fragments longer than 2.5 or 3 kb enhances the chances of identifying biallelic markers therein. Methods of constructing and sequencing a nested set of deletions are disclosed in the U.S. patent application Ser. No. 09/058,746.

Nucleic acids to be evaluated for the presence of biallelic markers therein may be obtained from groups of individuals, such as groups of 100 individuals, as described in Example 5.

EXAMPLE 5

Extraction of DNA 30 ml of blood are taken from the individuals in the presence of EDTA. Cells (pellet) are collected after centrifugation for 10 minutes at 2000 rpm. Red cells are lysed by a lysis solution (50 ml final volume: 10 mM Tris pH7.6; 5 mM $MgCl_2$; 10 mM NaCl). The solution is centrifuged (10 minutes, 2000 rpm) as many times as necessary to eliminate the residual red cells present in the supernatant, after resuspension of the pellet in the lysis solution.

The pellet of white cells is lysed overnight at 42° C. with 3.7 ml of lysis solution composed of:

3 ml TE 10-2 (Tris-HCl 10 mM, EDTA 2 mM)/NaCl 0.4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) is added. After vigorous agitation, the solution is centrifuged for 20 minutes at 10000 rpm. For the precipitation of DNA, 2 to 3 volumes of 100% ethanol are added to the previous supernatant, and the solution is centrifuged for 30 minutes at 2000 rpm. The DNA solution is rinsed three times with 70% ethanol to eliminate salts, and centrifuged for 20 minutes at 2000 rpm. The pellet is dried at 37° C., and resuspended in 1 ml TE 10-1 or 1 ml water. The DNA concentration is evaluated by measuring the OD at 260 mn (1 unit OD =50 µg/ml DNA).

To evaluate the presence of proteins in the DNA solution, the OD 260/OD 280 ratio is determined. Only DNA preparations having a OD 260/OD 280 ratio between 1.8 and 2 are used in the subsequent steps described below.

Once genomic DNA from every individual in the given population has been extracted, it is preferred that a fraction of each DNA sample is separated, after which a pool of DNA is constituted by assembling equivalent DNA amounts of the separated fractions into a single one. The pooled DNA samples can be used to identify biallelic markers as described in Example 6.

EXAMPLE 6

Amplification of DNA from Peripheral Blood and Identification of Biallelic Markers The amplification of each sequence is performed on pooled DNA samples obtained as in Example 5 above, using PCR (Polymerase Chain Reaction) as follows:

| | |
|---|---|
| final volume | 25 µl |
| genomic DNA | 2 ng/µl |
| $MgCl_2$ | 2 mM |
| dNTP (each) | 200 µM |
| primer (each) | 2.9 ng/µl |
| Ampli Taq Gold DNA polymerase (Perkin) | 0.05 unit/µl |
| PCR buffer (10X = 0.1 M TrisHCl pH 8.3, 0.5 M KCl | 1X |

The synthesis of primers is performed following the phosphoramidite method, on a GENSET UFPS 24.1 synthesizer.

To reduce the expense of preparing amplification primers for use in the above procedures, short primers may be used. While primers and probes having between 15 and 20 (or more) nucleotides are usually highly specific to a given nucleic acid sequence, it may be inconvenient and expensive to synthesize a relatively long oligonucleotide for each analysis. In order to at least partially circumvent this problem, it is often possible to use smaller but still relatively specific oligonucleotides that are shorter in length to create a manageable library. For example, a library of oligonucleotides comprising about 8 to 10 nucleotides is conceivable and has already been used for sequencing of a 40,000 bp cosmid DNA (Studier, Proc. Natl. Acad. Sci. USA 86(18): 6917–6921 (1989), the disclosure of which is incorporated herein by reference).

Another potential way to obtain specific primers and probes with a small library of oligonucleotides is to generate longer, more specific primers and probes from combinations of shorter, less specific oligonucleotides. Libraries of shorter oligonucleotides, each one being from about five to eight nucleotides in length, have already been used (Kieleczawa et al., Science 258:1787–1791 (1992); Kotler et al., Proc. Natl. Acad. Sci. USA 90:4241–4245 (1993); Kaczorowski and Szybalski, Anal Biochem. 221:127–135 (1994), the disclosures of which are incorporated herein by reference). Suitable probes and primers of appropriate length can therefore be designed through the association of two or three shorter oligonucleotides to constitute modular primers. The association between primers can be either covalent resulting from the activity of DNA T4 ligase or non-covalent through base-stacking energy.

The amplification is performed on a Perkin Elmer 9600 Thermocycler or M J Research PTC200 with heating lid. After heating at 95° C. for 10 minutes, 40 cycles are performed. Each cycle comprises: 30 sec at 95° C., 1 minute at 54° C., and 30 sec at 72° C. For final elongation, 10 minutes at 72° C. ends the amplification.

The quantities of the amplification products obtained are determined on 96-well microtiter plates, using a fluorimeter and Picogreen as intercalating agent (Molecular Probes).

The sequences of the amplification products are determined using automated dideoxy terminator sequencing reactions with a dye-primer cycle sequencing protocol. The products of the sequencing reactions are run on sequencing gels and the sequences are determined using gel image analysis.

The sequence data are evaluated using software designed to detect the presence of biallelic sites among the pooled amplified fragments. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. The software evaluates the intensity ratio between the two peaks and the intensity ratio between a given peak and surrounding peaks of the same color.

However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products which contain biallelic markers to be identified.

EXAMPLE 7

Screening BAC Libraries with Biallelic Markers

Amplification primers enabling the specific amplification of DNA fragments carrying the biallelic markers may be used to screen clones in any genomic DNA library, preferably the BAC libraries described above, for the presence of the biallelic markers.

Pairs of primers are designed which allow the amplification of fragments carrying the biallelic markers obtained as described above. The amplification primers may be used to screen clones in a genomic DNA library for the presence of the biallelic markers.

The amplification primers for the biallelic markers may be any sequences which allow the specific amplification of any DNA fragment carrying the markers and may be designed using techniques familiar to those skilled in the art. The amplification primers may be oligonucleotides of 8, 10, 15, 20 or more bases in length which enable the amplification of any fragment carrying the polymorphic site in the markers. The polymorphic base may be in the center of the amplification product or, alternatively, it may be located off-center. For example, in some embodiments, the amplification product produced using these primers may be at least 100 bases in length (i.e. 50 nucleotides on each side of the polymorphic base in amplification products in which the polymorphic base is centrally located). In other embodiments, the amplification product produced using these primers may be at least 500 bases in length (i.e. 250 nucleotides on each side of the polymorphic base in amplification products in which the polymorphic base is centrally located). In still further embodiments, the amplification product produced using these primers may be at least 1000 bases in length (i.e. 500 nucleotides on each side of the polymorphic base in amplification products in which the polymorphic base is centrally located).

The localization of biallelic markers on BAC clones is performed essentially as described in Example 2.

The BAC clones to be screened are distributed in three dimensional pools as described in Example 2.

Amplification reactions are conducted on the pooled BAC clones using primers specific for the biallelic markers to identify BAC clones which contain the biallelic markers, using procedures essentially similar to those described in Example 2.

Amplification products resulting from the amplification reactions are detected by conventional agarose gel electrophoresis combined with automatic image capturing and processing. PCR screening for a biallelic marker involves three steps: (1) identifying the positive primary pools; (2) for each positive primary pools, identifying the positive plate, row and column 'subpools' to obtain the address of the positive clone; (3) directly confirming the PCR assay on the identified clone. PCR assays are performed with primers defining the biallelic marker.

Screening is conducted as follows. First BAC DNA is isolated as follows. Bacteria containing the genomic inserts are grown overnight at 37° C. in 120 µl of LB containing chloramphenicol (12 µg/ml). DNA is extracted by the following protocol:

Centrifuge 10 min at 4° C. and 2000 rpm

Eliminate supernatant and resuspend pellet in 120 µl TE 10-2 (Tris HCl 10 mM, EDTA 2 mM)

Centrifuge 10 min at 4° C. and 2000 rpm

Eliminate supernatant and incubate pellet with 20 µl lyzozyme 1 mg/ml during 15 min at room temperature Add 20 µl proteinase K 100 µg/ml and incubate 15 min at 60° C.

Add 8 µl DNAse 2 U/µl and incubate 1 hr at room temperature

Add 100 µl TE 10-2 and keep at −80° C.

PCR assays are performed using the following protocol:

| | |
|---|---|
| Final volume | 15 µl |
| BAC DNA | 1.7 ng/µl |
| MgCl$_2$ | 2 mM |
| dNTP (each) | 200 µM |
| primer (each) | 2.9 ng/µl |
| Ampli Taq Gold DNA polymerase | 0.05 unit/µl |
| PCR buffer (10x = 0.1 M TrisHCl pH 8.3 0.5 M KCl | 1x |

The amplification is performed on a Genius II thermocycler. After heating at 95° C. for 10 min, 40 cycles are performed. Each cycle comprises: 30 sec at 95° C., 54° C. for 1 min, and 30 sec at 72° C. For final elongation, 10 min at 72° C. end the amplification. PCR products are analyzed on 1% agarose gel with 0.1 mg/ml ethidium bromide.

EXAMPLE 8

Assignment of Biallelic Markers to Subchromosomal Regions

Metaphase chromosomes are prepared from phytohemagglutinin (PHA)-stimulated blood cell donors. PHAstimulated lymphocytes from healthy males are cultured for 72 h in RPMI-1640 medium. For synchronization, methotrexate (10 raw is added for 17 h, followed by addition of 5-bromodeoxyuridine (5-BudR, 0.1 mM) for 6 h Colcemid (1 mg/ml) is added for the last 15 min before harvesting the cells. Cells are collected, washed in RPMI, incubated with a hypotonic solution of KCl (75 mM) at 37° C. for 15 min and fixed in three changes of methanol:acetic acid (3:1). The cell suspension is dropped onto a glass slide and air-dried.

BAC clones carrying the biallelic markers used to construct the maps can be isolated as described above. These BACs or portions thereof, including fragments carrying said biallelic markers, obtained for example from amplification reactions using pairs of amplification primers as described above, can be used as probes to be hybridized with metaphasic chromosomes. It will be appreciated that the hybridization probes to be used in the contemplated method may be generated using alternative methods well known to those skilled in the art. Hybridization probes may have any length suitable for this intended purpose.

Probes are then labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5–10 min.

Slides kept at −20° C. are treated for 1 h at 37° C. with RNase A (100 mg/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 mg/100 ml in 20 mM Tris-HCl, 2 mM $CaCl_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al.,(1990) supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular biallelic marker may be localized to a particular cytogenetic R-band on a given chromosome.

EXAMPLE 9

Assignment of Biallelic Markers to Human Chromosomes

The biallelic markers used to construct the maps may be assigned to a human chromosome using monosomal analysis as described below.

The chromosomal localization of a biallelic marker can be performed through the use of somatic cell hybrid panels. For example 24 panels, each panel containing a different human chromosome, may be used (Russell et al., *Somat Cell Mol. Genet* 22:425–431 (1996); Drwinga et al., *Genomics* 16:311–314 (1993), the disclosures of which are incorporated herein by reference).

The biallelic markers are localized as follows. The DNA of each somatic cell hybrid is extracted and purified. Genomic DNA samples from a somatic cell hybrid panel are prepared as follows. Cells are lysed overnight at 42° C. with 3.7 ml of lysis solution composed of:

3 ml TE 10-2 (Tris HCl 10 mM, EDTA 2 mM)/NaCl 0.4 M

200 µl SDS 10%

500 µl K-proteinase (2 mg K-proteinase in TE 10-2/NaCl 0.4 M)

For the extraction of proteins, 1 ml saturated NaCl (6M) (1/3.5 v/v) is added. After vigorous agitation, the solution is centrifuged for 20 min at 10,000 rpm. For the precipitation of DNA, 2 to 3 volumes of 100% ethanol are added to the previous supernatant, and the solution is centrifuged for 30 min at 2,000 rpm. The DNA solution is rinsed three times with 70% ethanol to eliminate salts, and centrifuged for 20 min at 2,000 rpm. The pellet is dried at 37° C., and resuspended in 1 ml TE 10-1 or 1 ml water. The DNA concentration is evaluated by measuring the OD at 260 nm (1 unit OD=50 µg/ml DNA). To determine the presence of proteins in the DNA solution, the $OD_{260}/OD_{280}$ ratio is determined. Only DNA preparations having a $OD_{260}/OD_{280}$ ratio between 1.8 and 2 are used in the PCR assay.

Then, a PCR assay is performed on genomic DNA with primers defining the biallelic marker. The PCR assay is performed as described above for BAC screening. The PCR products are analyzed on a 1% agarose gel containing 0.2 mg/ml ethidium bromide.

EXAMPLE 10

Measurement of Linkage Disequilibrium

As originally reported by Strittmatter et al. and by Saunders et al. in 1993, the Apo E e4 allele is strongly associated with both late-onset familial and sporadic Alzheimer's disease (AD). (Saunders, A. M. *Lancet* 342: 710–711 (1993) and Strittmater, W. J. et al., *Proc. Natl. Acad. Sci. U.S.A.* 90:1977–1981 (1993), the disclosures of which are incorporated herein by reference). The 3 major isoforms of human Apolipoprotein E (apoE2, -E3, and -E4), as identified by isoelectric focusing, are coded for by 3 alleles (e 2, 3, and 4). The e 2, e 3, and e 4 isoforms differ in amino acid sequence at 2 sites, residue 112 (called site A) and residue 158 (called site B). The ancestral isoform of the protein is Apo E3, which at sites A/B contains cysteine/arginine, while ApoE2 and -E4 contain cysteine/cysteine and arginine/arginine, respectively (Weisgraber, K. H. et al., *J. Biol. Chem.* 256: 9077–9083 (1981); Rall, S. C. et al., *Proc. Natl. Acad. Sci. U.S.A.* 79:4696–4700 (1982), the disclosures of which are incorporated herein by reference).

Apo E e 4 is currently considered as a major susceptibility risk factor for AD development in individuals of different ethnic groups (specially in Caucasians and Japanese compared to Hispanics or African Americans), across all ages between 40 and 90 years, and in both men and women, as reported recently in a study performed on 5930 AD patients and 8607 controls (Farrer et al., *JAMA* 278:1349–1356 (1997), the disclosure of which is incorporated herein by reference). More specifically, the frequency of a C base coding for arginine 112 at site A is significantly increased in AD patients.

Although the mechanistic link between Apo E e 4 and neuronal degeneration characteristic of AD remains to be established, current hypotheses suggest that the Apo E genotype may influence neuronal vulnerability by increasing the deposition and/or aggregation of the amyloid beta peptide in the brain or by indirectly reducing energy availability to neurons by promoting atherosclerosis.

Using the methods described above, biallelic markers that are in the vicinity of the Apo E site A were generated and the association of one of their alleles with Alzheimer's disease was analyzed. An Apo E public marker (stSG94) was used to screen a human genome BAC library as previously described. A BAC, which gave a unique FISH hybridization signal on chromosomal region 19q13.2.3, the chromosomal region harboring the Apo E gene, was selected for finding biallelic markers in linkage disequilibrium with the Apo E gene as follows.

This BAC contained an insert of 205 kb that was subcloned as previously described. Fifty BAC subclones were randomly selected and sequenced. Twenty five subclone sequences were selected and used to design twenty five pairs of PCR primers allowing 500 bp-amplicons to be generated. These PCR primers were then used to amplify the corresponding genomic sequences in a pool of DNA from 100 unrelated individuals (blood donors of French origin) as already described.

Amplification products from pooled DNA were sequenced and analyzed for the presence of biallelic polymorphisms, as already described. Five amplicons were shown to contain a polymorphic base in the pool of 100 unrelated individuals, and therefore these polymorphisms were selected as random biallelic markers in the vicinity of the Apo E gene. The sequences of both alleles of these biallelic, markers (99-344/439 ; 99-355/219 ; 99-359/308; 99-365/344; 99-366/274) correspond to SEQ ID Nos: 1–5 and 7–11 (See the accompanying Sequence Listing). Corresponding pairs of amplification primers for generating amplicons containing these biallelic markers can be chosen from those listed as SEQ ID Nos: 13–17 and 19–23.

An additional pair of primers (SEQ ID Nos: 18 and 24) was designed that allows amplification of the genomic fragment carrying the biallelic polymorphism corresponding to the ApoE marker (99-2452/54; C/T; The C allele is designated SEQ ID NO: 6 in the accompanying sequence listing, while the T allele is designated SEQ ID NO: 12 in the accompanying Sequence Listing; publicly known as Apo E site A (Weisgraber et al. (1981), supra; Rall et al. (1982), supra) to be amplified.

The five random biallelic markers plus the Apo E site A marker were physically ordered by PCR screening of the corresponding amplicons using all available BACs originally selected from the genomic DNA libraries, as previously described, using the public Apo E marker stSG94. The amplicon's order derived from this BAC screening is as follows:

(99-344/99-366)-(99-365/99-2452)-99-359-99-355, where brackets indicate that the exact order of the respective amplicons couldn't be established.

Linkage disequilibrium among the six biallelic markers (five random markers plus the Apo E site A) was determined by genotyping the same 100 unrelated individuals from whom the random biallelic markers were identified.

DNA samples and amplification products from genomic PCR were obtained in similar conditions as those described above for the generation of biallelic markers, and subjected to automated microsequencing reactions using fluorescent ddNTPs (specific fluorescence for each ddNTP) and the appropriate microsequencing primers having a 3' end immediately upstream of the polymorphic base in the biallelic markers. The sequence of these microsequencing primers is indicated within the corresponding sequence listings of SEQ ID Nos: 25–30. Once specifically extended at the 3' end by a DNA polymerase using the complementary fluorescent dideoxynucleotide analog (thermal cycling), the microsequencing primer was precipitated to remove the unincorporated fluorescent ddNTPs. The reaction products were analyzed by electrophoresis on ABI 377 sequencing machines. Results were automatically analyzed by appropriate software further described in Example 13.

Linkage disequilibrium (LD) between all pairs of biallelic markers (Mi, Mj) was calculated for every allele combination (Mi1,Mj1; Mi1,Mj2; Mi2,Mj1; Mi2, Mj2) according to the maximum likelihood estimate (MLE) for delta (the composite linkage disequilibrium coefficient). The results of the LD analysis between the Apo E Site A marker and the five new biallelic markers (99-344/439; 99-355/219; 99-359/308; 99-365/344; 99-366/274) are summarized in Table 1 below:

TABLE 1

| Markers | d x 100 | SEQ ID Nos of the biallelic Markers | SEQ ID Nos of the amplification Primers |
|---|---|---|---|
| | ApoE Site A | 6 | 18 |
| | 99-2452/54 | 12 | 24 |
| 99-344/439 | 1 | 1 | 13 |
| | | 7 | 19 |
| 99-366/274 | 1 | 2 | 14 |
| | | 8 | 20 |
| 99-365/344 | 8 | 5 | 17 |
| | | 11 | 23 |
| 99-359/308 | 2 | 3 | 15 |
| | | 9 | 21 |
| 99-355/219 | 1 | 4 | 16 |
| | | 10 | 22 |

The above LD results indicate that among the five biallelic markers randomly selected in a region of about 200 kb containing the Apo E gene, marker 99-365/344T is in relatively strong linkage disequilibrium with the Apo E site A allele (99-2452/54C).

Therefore, since the Apo E site A allele is associated with Alzheimer's disease, one can predict that the T allele of marker 99-365/344 will probably be found associated with AD. In order to test this hypothesis, the biallelic markers of SEQ ID Nos: 1–6 and 7–12 were used in association studies as described below.

225 Alzheimer's disease patients were recruited according to clinical inclusion criteria based on the MMSE test. The 248 control cases included in this study were both ethnically- and age-matched to the affected cases. Both affected and control individuals corresponded to unrelated cases. The identities of the polymorphic bases of each of the biallelic markers was determined in each of these individuals using the methods described above. Techniques for conducting association studies are further described below.

The results of this study are summarized in Table 2 below:

TABLE 2

| | ASSOCIATION DATA | |
|---|---|---|
| MARKER | Difference in allele frequency between individuals with Alzheimer's and control individuals | Corresponding p-value |
| 99-344/439 | 3.3% | 9.54 E-02 |
| 99-366/274 | 1.6% | 2.09 E-01 |
| 99-365/344 | 17.7% | 6.9 E-10 |
| 99-2452/54 | 23.8% | 3.95 E-21 |

TABLE 2-continued

ASSOCIATION DATA

| MARKER | Difference in allele frequency between individuals with Alzheimer's and control individuals | Corresponding p-value |
|---|---|---|
| (ApoE Site A) | | |
| 99-359/308 | 0.4% | 9.2 E-01 |
| 99-355/219 | 2.5% | 2.54 E-01 |

The frequency of the Apo E site A allele in both AD cases and controls was found in agreement with that previously reported (ca. 10% in controls and ca. 34% in AD cases, leading to a 24% difference in allele frequency), thus validating the Apo E e4 association in the populations used for this study.

Moreover, as predicted from the LD analysis (Table 1), a significant association of the T allele of marker 99-365/344 with AD cases (18% increase in the T allele frequency in AD cases compared to controls, p value for this difference=6.9 E-10) was observed.

The above results indicate that any marker in LD with one given marker associated with a trait will be associated with the trait. It will be appreciated that, though in this case the ApoE Site A marker is the trait-causing allele (TCA) itself, the same conclusion could be drawn with any other non TCA marker associated with the studied trait.

These results further indicate that conducting association studies with a set of biallelic markers randomly generated within a candidate region at a sufficient density (here about one biallelic marker every 40 kb on average), allows the identification of at least one marker associated with the trait.

In addition, these results correlate with the physical order of the six biallelic markers contemplated within the present example (see above): marker 99-365/344, which had been found to be the closest in terms of physical distance to the ApoE Site A marker, also shows the strongest LD with the Apo E site A marker.

In order to further refine the relationship between physical distance and linkage disequilibrium between biallelic markers, a ca. 450 kb fragment from a genomic region on chromosome 8 was fully sequenced.

LD within ca. 230 pairs of biallelic markers derived therefrom was measured in a random French population and analyzed as a function of the known physical inter-marker spacing. This analysis confirmed that, on average, LD between 2 biallelic markers correlates with the physical distance that separates them. It further indicated that LD between 2 biallelic markers tends to decrease when their spacing increases. More particularly, LD between 2 biallelic markers tends to decrease when their inter-marker distance is greater than 50 kb, and is further decreased when the inter-marker distance is greater than 75 kb. It was further observed that when 2 biallelic markers were further than 150 kb apart, most often no significant LD between them could be evidenced. It will be appreciated that the size and history of the sample population used to measure LD between markers may influence the distance beyond which LD tends not to be detectable.

Assuming that LD can be measured between markers spanning regions up to an average of 150 kb long, biallelic marker maps will allow genome-wide LD mapping, provided they have an average inter-marker distance lower than 150 kb.

EXAMPLE 11

Identification of a Candidate Region Harboring a Gene Associated with a Detectable Trait The initial identification of a candidate genomic region harboring a gene associated with a detectable trait may be conducted using a genome-wide map comprising about 20,000 biallelic markers. The candidate genomic region may be further defined using a map having a higher marker density, such as a map comprising about 40,000 markers, about 60,000 markers, about 80,000 markers, about 100,000 markers, or about 120,000 markers.

The use of high density maps such as those described above allows the identification of genes which are truly associated with detectable traits, since the coincidental associations will be randomly distributed along the genome while the true associations will map within one or more discrete genomic regions. Accordingly, biallelic markers located in the vicinity of a gene associated with a detectable trait will give rise to broad peaks in graphs plotting the frequencies of the biallelic markers in T+ individuals versus T− individuals. In contrast, biallelic markers which are not in the vicinity of the gene associated with the detectable trait will produce unique points in such a plot. By determining the association of several markers within the region containing the gene associated with the detectable trait, the gene associated with the detectable trait can be identified using an association curve which reflects the difference between the allele frequencies within the T+ and T− populations for each studied marker. The gene associated with the detectable trait will be found in the vicinity of the marker showing the highest association with the trait.

Figure 4:
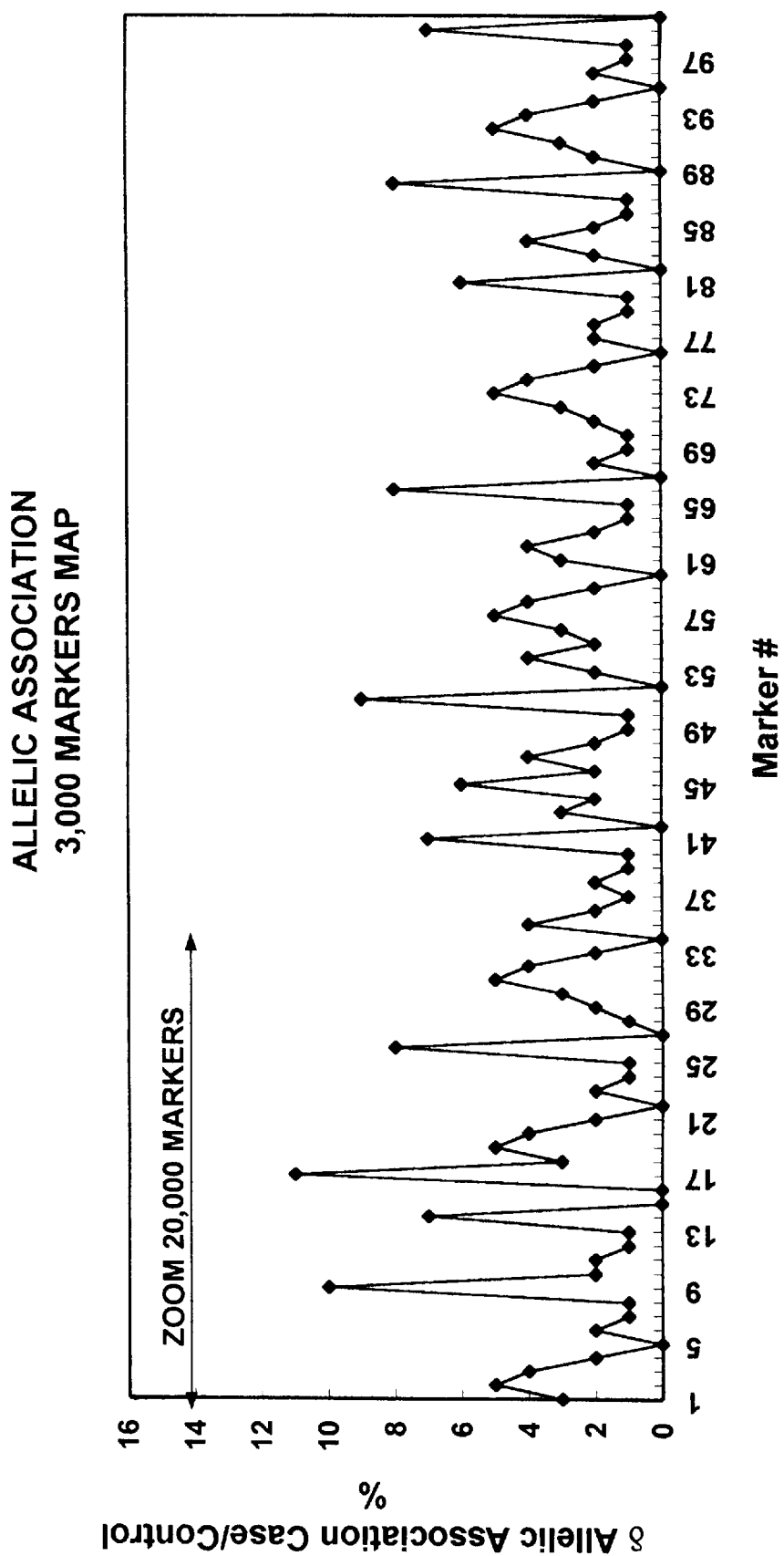
FIG. 4 is a hypothetical association analysis conducted with a map comprising about 3,000 biallelic markers.
Figure 5:
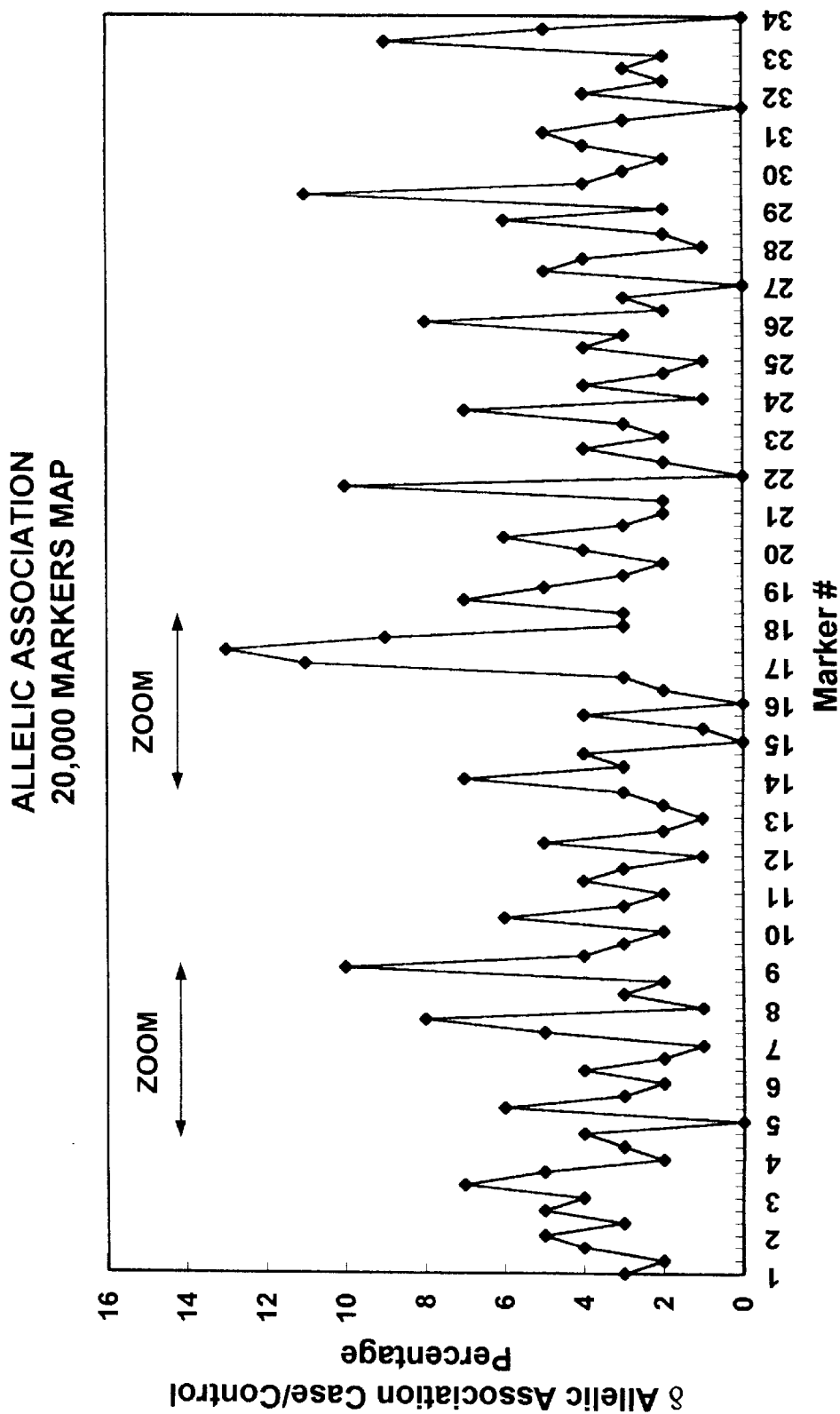
FIG. 5 is a hypothetical association analysis conducted with a map comprising about 20,000 biallelic markers.
Figure 6:
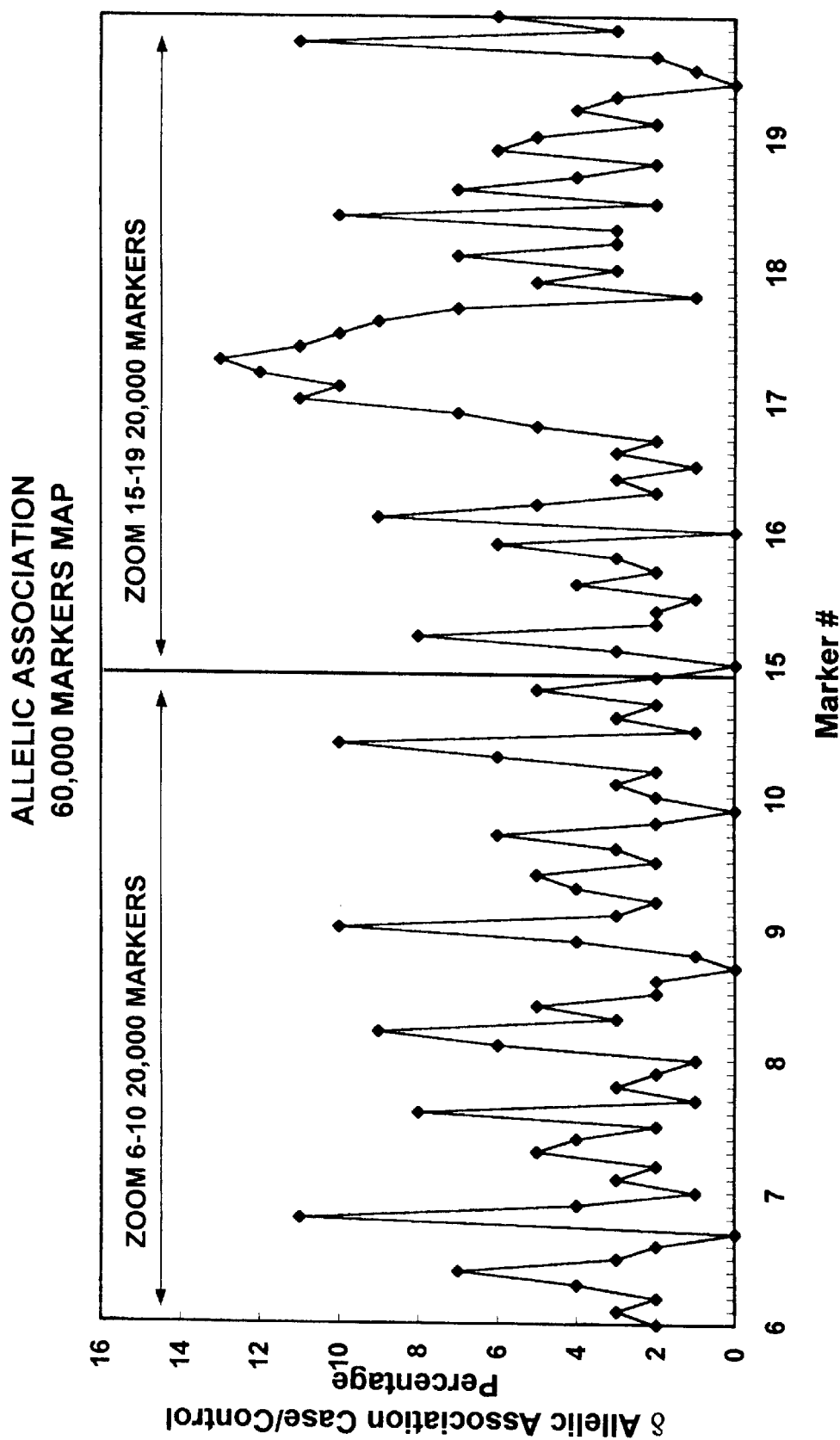
FIG. 6 is a hypothetical association analysis conducted with a map comprising about 60,000 biallelic markers.

FIGS. 4, 5, and 6 illustrate the above principles. As illustrated in FIG. 4, an association analysis conducted with a map comprising about 3,000 biallelic markers yields a group of points. However, when an association analysis is performed using a denser map which includes additional biallelic markers, the points become broad peaks indicative of the location of a gene associated with a detectable trait. For example, the biallelic markers used in the initial association analysis may be obtained from a map comprising about 20,000 biallelic markers, as illustrated in FIG. 5.

In the hypothetical example of FIG. 4, the association analysis with 3,000 markers suggests peaks near markers 9 and 17.

Next, a second analysis is performed using additional markers in the vicinity of markers 9 and 17, as illustrated in the hypothetical example of FIG. 5, using a map of about 20,000 markers. This step again indicates an association in the close vicinity of marker 17, since more markers in this region show an association with the trait. However, none of the additional markers around marker 9 shows a significant association with the trait, which makes marker 9 a potential false positive. In order to further test the validity of these two suspected associations, a third analysis may be obtained with a map comprising about 60,000 biallelic markers. In the hypothetical example of FIG. 6, more markers lying around marker 17 exhibit a high degree of association with the detectable trait. Conversely, no association is confirmed in the vicinity of marker 9. The genomic region surrounding marker 17 can thus be considered a candidate region for the hypothetical trait of this simulation.

EXAMPLE 12

Haplotype Analysis: Identification of Biallelic Markers Delineating a Genomic Region Associated with Alzheimer's Disease (AD)

As shown in Table 2 within Example 10, at an average map density of one marker per 40 kb only one marker (99-365/344) out of five random biallelic markers from a ca. 200 kb genomic region around the Apo E gene showed a clear association to AD (delta allelic frequency in cases and controls=18%; p value=6.9 E-10). The allelic frequencies of the other four random markers were not significantly different between AD cases and controls (p-values≧E-01). However, since linkage disequilibrium can usually be detected between markers located further apart than an average 40 kb as previously discussed, one should expect that, performing an association study with a local excerpt of a biallelic marker map covering ca. 200 kb with an average inter-marker distance of ca. 40 kb should allow the identification of more than one biallelic marker associated with AD.

A haplotype analysis was thus performed using the biallelic markers 99-344/439; 99-355/219; 99-359/308 ; 99-365/344 ; and 99-366/274 (of SEQ ID Nos: 1–5 and 7–11).

In a first step, marker 99-365/344 that was already found associated with AD was not included in the haplotype study. Only biallelic markers 99-344/439 ; 99-355/219 ; 99-359/308; and 99-366/274, which did not show any significant association with AD when taken individually, were used. This first haplotype analysis measured frequencies of all possible two-, three-, or four-marker haplotypes in the AD case and control populations. As shown in FIG. 7, there was one haplotype among all the potential different haplotypes based on the four individually non-significant markers ("haplotype 8", TAGG comprising SEQ ID No. 2 which is the T allele of marker 99-366/274, SEQ ID No. 1 which is the A allele of marker 99-344/439, SEQ ID No. 3 which is the G allele of marker 99-359/308 and SEQ ID No. 4 which is the G allele of marker 99-355/219), that was present at statistically significant different frequencies in the AD case and control populations (D=12%; p value=2.05 E-06). Moreover, a significant difference was already observed for a three-marker haplotype included in the above mentioned "haplotype 8" ("haplotype 7", TGG, D-10%D; p value =4.76 E-05). Haplotype 7 comprises SEQ ID No. 2 which is the T allele of marker 99-366/274, SEQ ID No. 3 which is the G allele of marker 99-359/308 and SEQ ID No. 4 which is the G allele of marker 99-355/219). The haplotype association analysis thus clearly increased the statistical power of the individual marker association studies by more than four orders of magnitude when compared to single-marker analysis (from p values≧E-01 for the individual markers—see Table 2—top value≦2 E-06 for the four-marker "haplotype 8").

Figure 8:
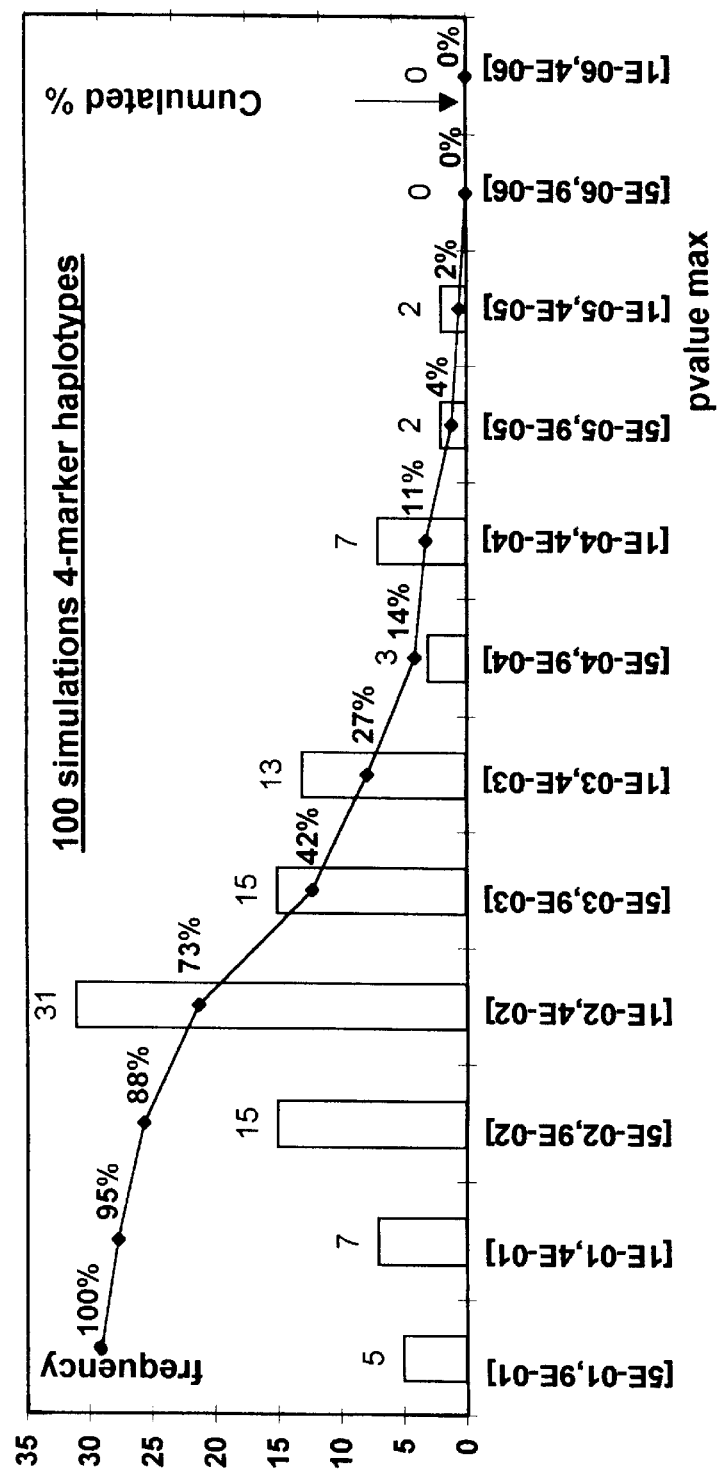
FIG. 8 is a simulated haplotype analysis using the biallelic markers in the Apo E region included in the haplotype analysis of FIG. 7.

The significance of the values obtained for this haplotype association analysis was evaluated by the following computer simulation. The genotype data from the AD cases and the unaffected controls were pooled and randomly allocated to two groups which contained the same number of individuals as the case/control groups used to produce the data summarized in FIG. 7. A four-marker haplotype analysis (99-344/439 ; 99-355/219 ; 99-359/308; and 99-366/274) was run on these artificial groups. This experiment was reiterated 100 times and the results are shown in FIG. 8. No haplotype among those generated was found for which the p-value of the frequency difference between both populations was more significant than 1 E-05. In addition, only 4% of the generated haplotypes showed p-values lower than 1 E-04. Since both these p-value thresholds are less significant than the 2 E-06 p-value showed by "haplotype 8", this haplotype can be considered significantly associated with AD.

In a second step, marker 99-365/344 was included in the haplotype analyzes. The frequency differences between the affected and non affected populations was calculated for all two-, three-, four- or five-marker haplotypes involving markers: 99-344/439; 99-355/219; 99-359/308 ; 99-366/274; and 99-365/344. The most significant p-values obtained in each category of haplotype (involving two, three, four or five markers) were examined depending on which markers were involved or not within the haplotype. This showed that all haplotypes which included marker 99-365/344 showed a significant association with AD (p-values in the range of E-04 to E-11), An additional way of evaluating the significance of the values obtained in the haplotype association analysis was to perform a similar AD case-control study on biallelic markers generated from BACs containing inserts corresponding to genomic regions derived from chromosomes 13 or 21 and not known to be involved in Alzheimer's disease. Performing similar haplotype and individual association analyzes as those described above and in Example 10 did not generate any significant association results (all p-values for haplotype analyzes were less significant than E-03; all p-values for single marker association studies were less significant than E-02).

In a preferred embodiment, the candidate genomic region may be evaluated using the methods described in Examples 20–23 below to determine whether it is likely to harbor a gene associated with Alzheimer's Disease.

The results described in Examples 10 and 12, generated from individual and haplotype studies using a biallelic marker set of an average density equal to ca. 40 kb in the region of an Alzheimer's disease trait causing gene, indicate that all biallelic markers of sufficient informative content located within a ca. 200 kb genomic region around a TCA can potentially be successfully used to localize a trait causing gene with the methods provided by the present invention. This conclusion is further supported by the results obtained through measuring the linkage disequilibrium between markers 99-365/344 or 99-359/308 and ApoE 4 Site A marker within Alzheimer's patients: as one could predict since LD is the supporting basis for association studies, LD between these pairs of markers was enhanced in the diseased population vs. the control population. In a similar way, the haplotype analysis enhanced the significance of the corresponding association studies.

EXAMPLE 13

Genotyping of Biallelic Markers using Microsequencing Procedures

Several microsequencing protocols conducted in liquid phase are well known to those skilled in the art. A first possible detection analysis allowing the allele characterization of the microsequencing reaction products relies on detecting fluorescent ddNTP-extended microsequencing primers after gel electrophoresis. A first alternative to this approach consists in performing a liquid phase microsequencing reaction, the analysis of which may be carried out in solid phase.

For example, the microsequencing reaction may be performed using 5'-biotinylated oligonucleotide primers and fluorescein-dideoxynucleotides. The biotinylated oligonucleotide is annealed to the target nucleic acid sequence immediately adjacent to the polymorphic nucleotide position of interest. It is then specifically extended at its 3'-end following a PCR cycle, wherein the labeled dideoxynucleotide analog complementary to the polymorphic base is incorporated. The biotinylated primer is then captured on a microtiter plate coated with streptavidin. The analysis is thus entirely carried out in a microtiter plate format. The incorporated ddNTP is detected by a fluorescein antibody-alkaline phosphatase conjugate.

In practice this microsequencing analysis is performed as follows. 20 µl of the microsequencing reaction is added to 80 µl of capture buffer (SSC 2×, 2.5% PEG 8000, 0.25 M Tris pH7.5, 1.8% BSA, 0.05% Tween 20) and incubated for 20 minutes on a microtiter plate coated with streptavidin (Boehringer). The plate is rinsed once with washing buffer (0.1 M Tris pH 7.5, 0.1 M NaCl, 0.1% Tween 2). 100 µl of anti-fluorescein antibody conjugated with phosphatase alkaline, diluted 1/5000 in washing buffer containing 1.8% BSA is added to the microtiter plate. The antibody is incubated on the microtiter plate for 20 minutes. After washing the microtiter plate four times, 100 µl of 4-methylumbelliferyl phosphate (Sigma) diluted to 0.4 mg/ml in 0.1 M diethanolamine pH 9.6, 10 mM $MgCl_2$ are added. The detection of the microsequencing reaction is carried out on a fluorimeter (Dynatech) after 20 minutes of incubation.

EXAMPLE 14

YAC Contig Construction in the Candidate Genomic Region

Substantial amounts of LOH data supported the hypothesis that genes associated with distinct cancer types are located within a particular region of the human genome. More specifically, this region was likely to harbor a gene associated with prostate cancer.

Association studies were performed as described below in order to identify this prostate cancer gene. A YAC contig containing the genomic region suspected of harboring a gene associated with prostate cancer was constructed as follows.

First, a YAC contig which contains the candidate genomic region was constructed as follows. The CEPH-Genethon YAC map for the entire human genome (Chumakov et al. (1995), supra) was used for detailed contig building in the genomic region containing genetic markers known to map in the candidate genomic region. Screening data available for several publicly available genetic markers were used to select a set of CEPH YACs localized within the candidate region. This set of YACs was tested by PCR with the above mentioned genetic markers as well as with other publicly available markers supposedly located within the candidate region. As a result of these studies, a YAC STS contig map was generated around genetic markers known to map in this genomic region. Two CEPH YACs were found to constitute a minimal tiling path in this region, with an estimated size of ca. 2 Megabases.

During this mapping effort, several publicly known STS markers were precisely located within the contig.

Example 15 below describes the identification of sets of biallelic markers within the candidate genomic region.

EXAMPLE 15

BAC Contig Construction and Biallelic Markers Isolation Within the Candidate Chromosomal Region Next, a BAC contig covering the candidate genomic region suspected of harboring a gene associated with prostate cancer was constructed as follows. BAC libraries were obtained as described in Woo et al., *Nucleic Acids Res.* 22:4922–4931 (1994), the disclosure of which is incorporated herein by reference. Briefly, the two whole human genome BamHI and HindIII libraries already described in Example 1 were constructed using the pBeloBAC11 vector (Kim et al. (1996), supra).

The BAC libraries were then screened with all of the above mentioned STSs, following the procedure described in Example 2 above.

The ordered BACs selected by STS screening and verified by FISH, were assembled into contigs and new markers were generated by partial sequencing of insert ends from some of them. These markers were used to fill the gaps in the contig of BAC clones covering the candidate chromosomal region having an estimated size of 2 megabases.

Figure 9:
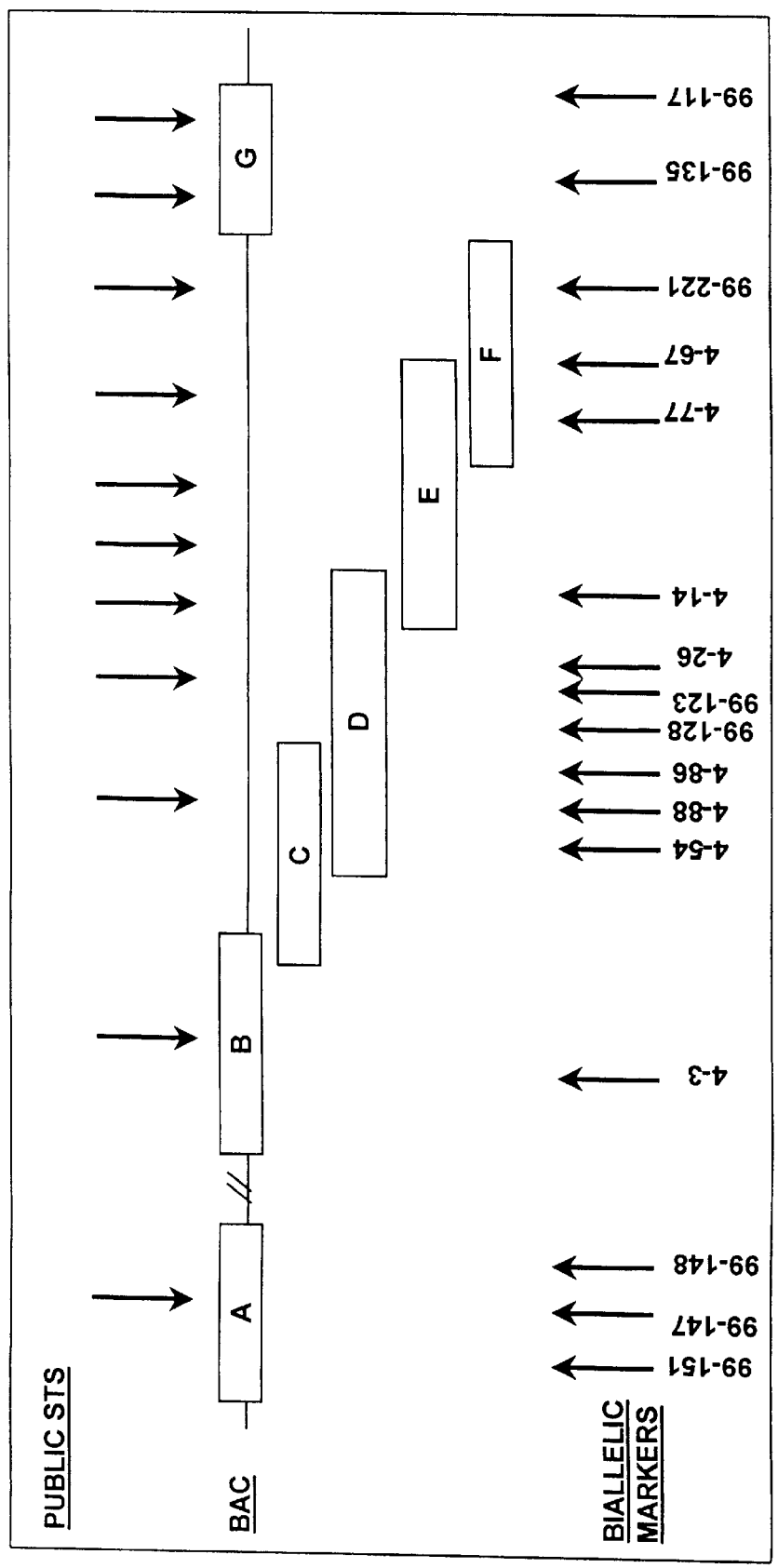
FIG. 9 shows a minimal array of overlapping clones which was chosen for further studies of biallelic markers associated with prostate cancer, the positions of STS markers known to map in the candidate genomic region along the contig, and the locations of biallelic markers along the BAC contig harboring a genomic region harboring a candidate gene associated with prostate cancer which were identified using the methods of the present invention.

FIG. 9 illustrates a minimal array of overlapping clones which was chosen for further studies, and the positions of the publicly known STS markers along said contig.

Selected BAC clones from the contig were subcloned and sequenced, essentially following the procedures described in Examples 3 and 4.

Biallelic markers lying along the contig were identified following the processes described in Examples 5 and 6.

FIG. 9 shows the locations of the biallelic markers along the BAC contig. This first set of markers corresponds to a medium density map of the candidate locus, with an inter-marker distance averaging 50 kb–150 kb.

A second set of biallelic markers was then generated as described above in order to provide a very high-density map of the region identified using the first set of markers which can be used to conduct association studies, as explained below. This very high density map has markers spaced on average every 2–50 kb.

The biallelic markers were then used in association studies. DNA samples were obtained from individuals suffering from prostate cancer and unaffected individuals as described in Example 16.

EXAMPLE 16

Collection of DNA Samples from Affected and Non-affected Individuals

Prostate cancer patients were recruited according to clinical inclusion criteria based on pathological or radical prostatectomy records. Control cases included in this study were both ethnically- and age-matched to the affected cases; they were checked for both the absence of all clinical and biological criteria defining the presence or the risk of prostate cancer, and for the absence of related familial prostate cancer cases. Both affected and control individuals were all unrelated.

The two following groups of independent individuals were used in the association studies. The first group, comprising individuals suffering from prostate cancer, contained 185 individuals. Of these 185 cases of prostate cancer, 47 cases were sporadic and 138 cases were familial. The control group contained 104 non-diseased individuals.

Haplotype analysis was conducted using additional diseased (total samples: 281) and control samples (total samples: 130), from individuals recruited according to similar criteria.

DNA was extracted from peripheral venous blood of all individuals as described in Example 5.

The frequencies of the biallelic markers in each population were determined as described in Example 17.

EXAMPLE 17

Genotyping Affected and Control Individuals

Genotyping was performed using the following microsequencing procedure. Amplification was performed on each DNA sample using primers designed as previously explained. The pairs of primers were used to generate amplicons harboring the biallelic markers 99-123, 4-26, 4-14, 4-77, 99-217, 4-67, 99-213, 99-221, 99-135, 99-1482, 4-73, and 4-65 using the protocols described in Example 6 above.

Microsequencing primers were designed for each of the biallelic markers, as previously described. After purification of the amplification products, the microsequencing reaction mixture was prepared by adding, in a 20 µl final volume: 10 pmol microsequencing oligonucleotide, 1 U Thermosequenase (Amersham E79000G), 1.25 µl Thermosequenase buffer (260 mM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized as homozygous or heterozygous based on the height ratio.

Association analyzes were then performed using the biallelic markers as described below.

EXAMPLE 18

Association Analysis

Figure 10:
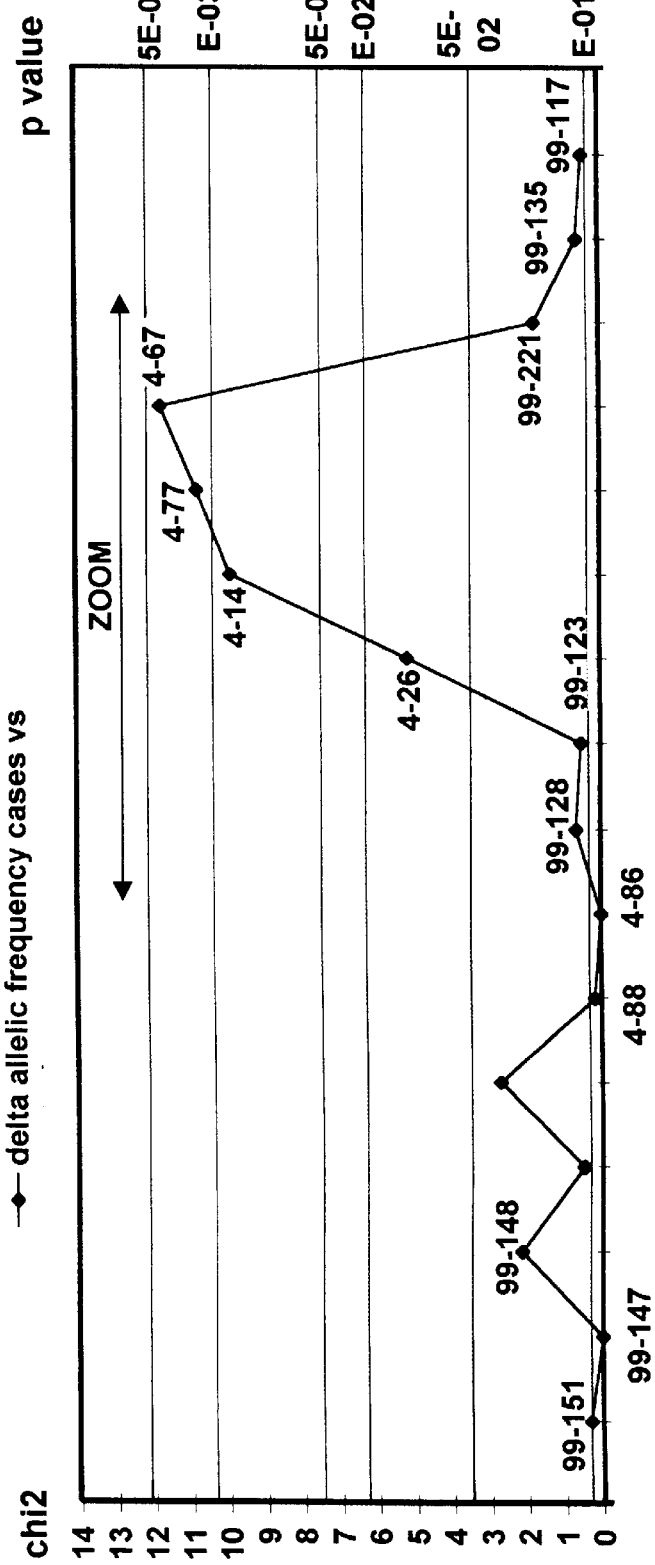
FIG. 10 is a rough localization of a candidate gene for prostate cancer which was obtained by determining the frequencies of the biallelic markers of FIG. 9 in affected and unaffected populations.

Association studies were run in two successive steps. In a first step, a rough localization of the candidate gene was achieved by determining the frequencies of the biallelic markers of FIG. 9 in the affected and unaffected populations. The results of this rough localization are shown in FIG. 10. This analysis indicated that a gene responsible for prostate cancer was located near the biallelic marker designated 4-67.

In a second phase of the analysis, the position of the gene responsible for prostate cancer was further refined using the very high density set of markers including the 99-123, 4-26, 4-14, 4-77, 99-217, 4-67, 99-213, 99-221, 99-135, 99-1482, 4-73, and 4-65 markers.

Figure 11:
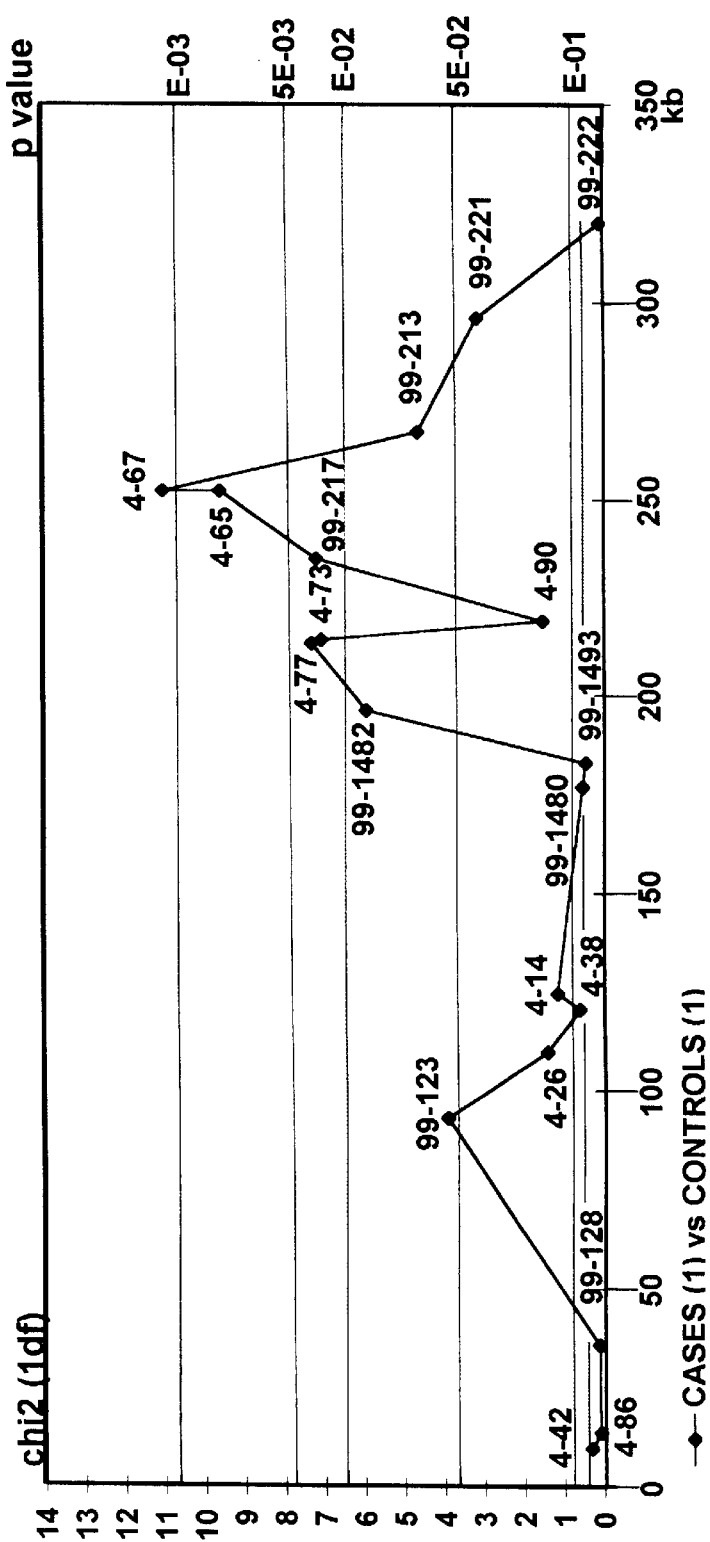
FIG. 11 is a further refinement of the localization of the candidate gene for prostate cancer using additional biallelic markers which were not included in the rough localization illustrated in FIG. 10.

As shown in FIG. 11, the second phase of the analysis confirmed that the gene responsible for prostate cancer was near the biallelic marker designated 4-67, most probably within a ca. 150 kb region comprising the marker.

A haplotype analysis was also performed as described in Example 19.

EXAMPLE 19

Haplotype analysis

The allelic frequencies of each of the alleles of biallelic markers 99-123, 4-26, 4-14, 4-77, 99-217, 4-67, 99-213, 99-221, and 99-135 were determined in the affected and unaffected populations. Table 3 lists the internal identification numbers of the markers used in the haplotype analysis, the alleles of each marker, the most frequent allele in both unaffected individuals and individuals suffering from prostate cancer, the least frequent allele in both unaffected individuals and individuals suffering from prostate cancer, and the frequencies of the least frequent alleles in each population.

TABLE 3

|         |                  | Frequency of least frequent allele** |          |
|---------|------------------|--------|----------|
| Markers | Polymorphic base* | Cases  | Controls |
| 99-123  | C/T              | 0.35   | 0.3      |
| 4-26    | A/G              | 0.39   | 0.45     |
| 4-14    | C/T              | 0.35   | 0.41     |
| 4-77    | C/G              | 0.33   | 0.24     |
| 99-217  | C/T              | 0.31   | 0.23     |
| 4-67    | C/T              | 0.26   | 0.16     |
| 99-213  | T/C              | 0.45   | 0.38     |
| 99-221  | C/A              | 0.43   | 0.43     |
| 99-135  | A/G              | 0.25   | 0.3      |

*most frequent allele/least frequent allele
**standard deviations
−0.023 to 0.031 for controls
−0.018 to 0.021 for cases Among all the theoretical potential different haplotypes based on 2 to 9 markers, 11 haplotypes showing a strong association with prostate cancer were selected. The results of these haplotype analyzes are shown in FIG. 12.

FIGS. 11, and 12 aggregate association analysis results with sequencing results—generated following the procedures further described in Example 21—which permitted the physical order and/or the distance between markers to be estimated.

Figure 13A:
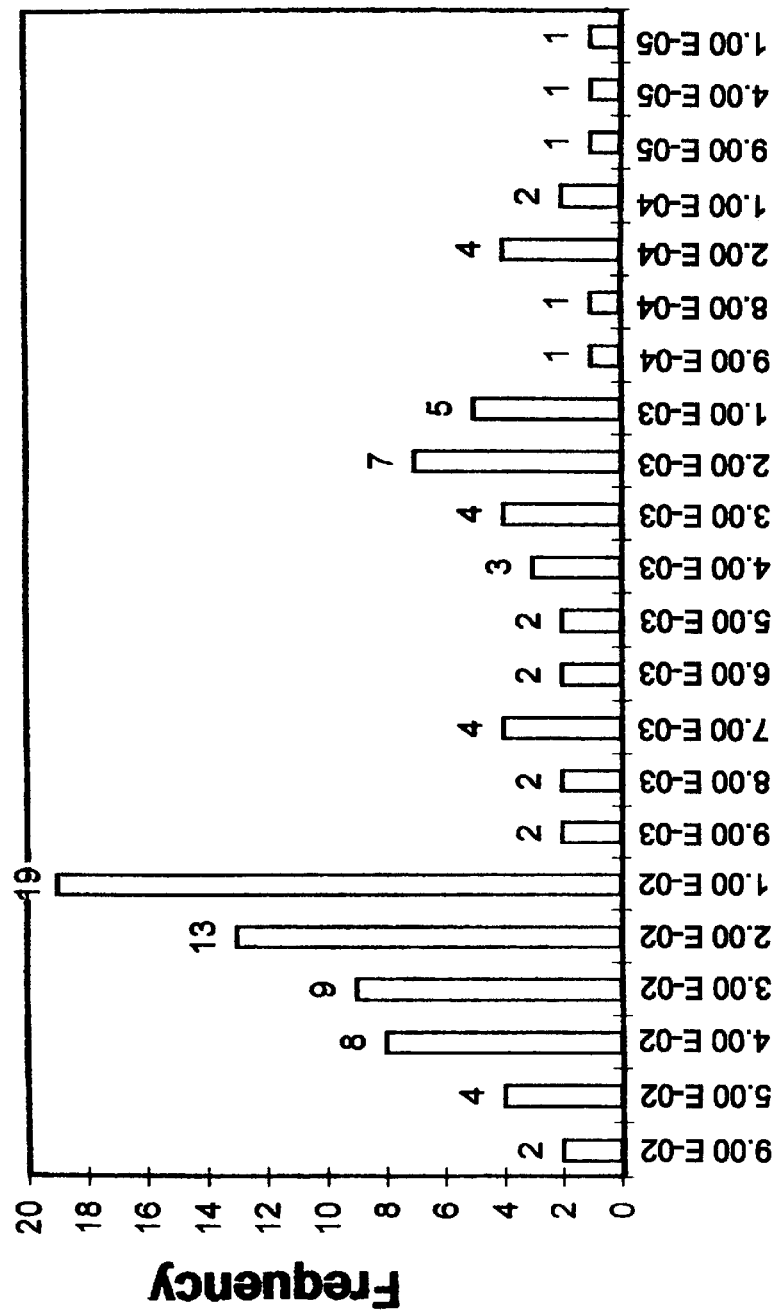
FIG. 13 is a simulated haplotype using the six markers included in haplotype 5 of FIG. 12.
Figure 13B:
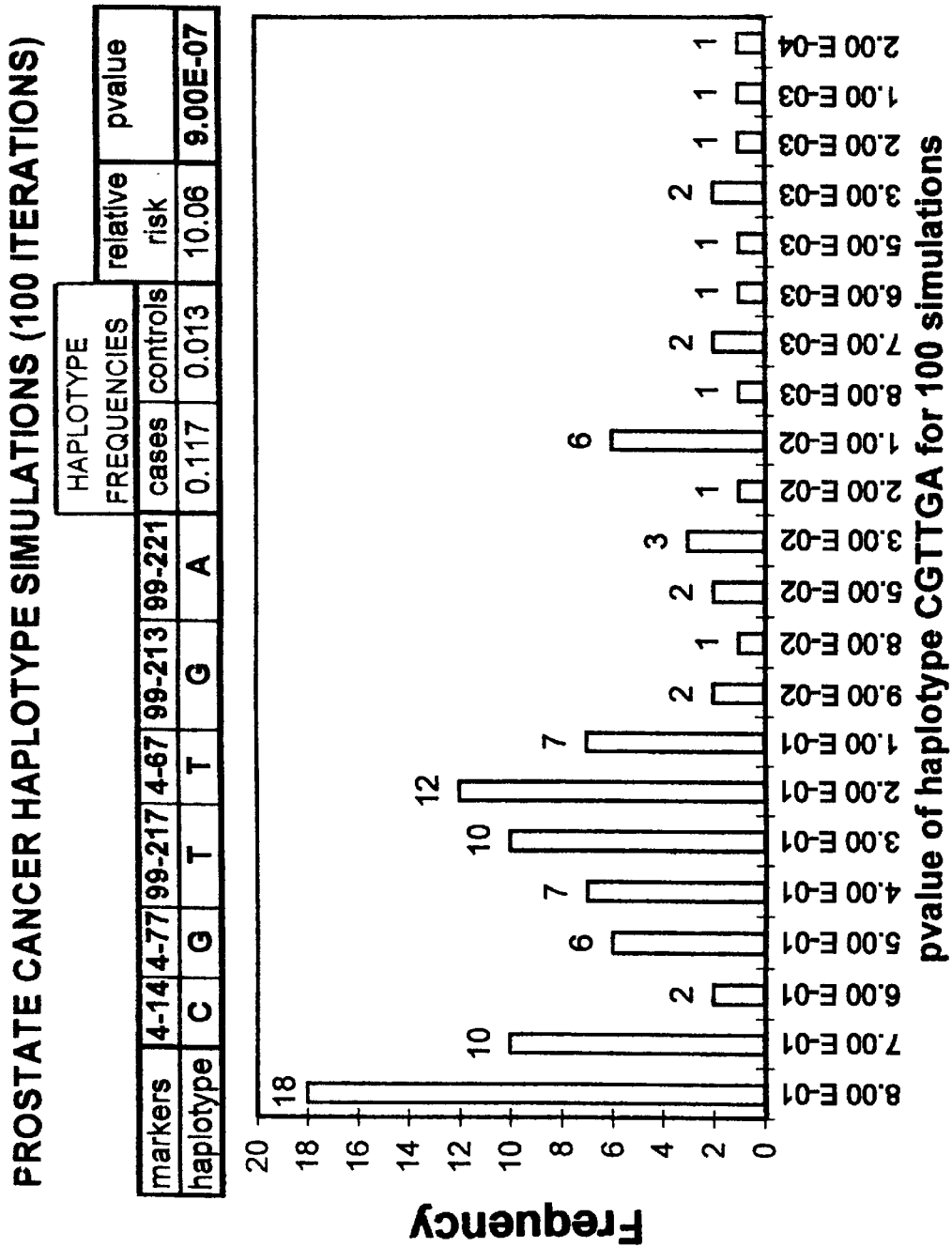

Thus, using the data of FIG. 13 and evaluating the associations for single marker alleles or for haplotypes will permit estimation of the risk a corresponding carrier has to develop prostate cancer. It will be appreciated that significance thresholds of relative risks will be more finely assessed according to the population tested.

EXAMPLE 20

Construction of the Random Region Distribution and the Candidate Region Distribution for a First Genomic Region Suspected of Harboring a Gene Associated with Prostate Cancer In a BAC insert suspected of harboring a gene associated with prostate cancer 35 biallelic markers were identified over a genomic region of 161 kb (i.e. an average intermarker distance of approximately 4.5 kb). The 35 markers were divided into groups of 3 markers each and the frequencies of each of the eight possible haplotypes of markers (a total of 6,545 combinations of 3 markers) in the groups were estimated in individuals suffering from prostate cancer and control individuals who did not have prostate cancer using the Expectation-Maximization algorithm of Excoffier and Slatkin. For each group of 3 markers, the frequency of each of the eight possible haplotypes in individuals having prostate cancer and control individuals were compared using a chi-squared analysis, which measures the difference between the two frequencies weighted by the sample sizes and haplotype frequencies. The chi squared value for the haplotype having the greatest association with prostate cancer was selected for inclusion in the candidate region distribution. Every combination of 3 markers was used in the analysis. Thus, there were 6,545 chi-squared values included in the candidate region distribution.

The random region distribution was obtained as follows. A total of thirty biallelic markers from BAC inserts were used to generate the random region distribution. The number of markers per BAC in the random BACs ranged from 3 to 9, with a median at 3. All the markers fit the Hardy-Weinberg equilibrium.

For each BAC insert, the markers on that insert were divided into groups of 3 markers. The frequencies of each of the eight possible haplotypes of markers (a total of 240 combinations of 3 markers) in the groups were estimated in individuals suffering from prostate cancer and control individuals who did not have prostate cancer using the Expectation-Maximization algorithm of Excoffier L and Slatkin. For each group of 3 markers, the frequency of each haplotype in individuals having prostate cancer and control individuals were compared using a chi-squared analysis and the chi squared value for the haplotype having the greatest association with prostate cancer was selected for inclusion in the random region distribution. Every combination of 3 markers was used in the analysis. Thus, there were 240 chi-squared values included in the random region distribution.

Table 4 below shows the number of BACs, the number of markers, the number of 3 marker combinations, and the sample sizes used to construct the random region distribution and the candidate region distribution.

TABLE 4 description of markers and population used in the analysis

| Region | # of bacs | # of markers | # of 3 mks-combinations | Sample size (# of Cases vs # of controls) |
|---|---|---|---|---|
| Bac containing the Gene | 1 | 35 | 6545 | [180; 350] vs [100; 130]* |
| Random bacs | 30 | 116 | 240 | [180; 350] vs [100; 130] |

*for cases samples size varied from 180 to 350. For controls sample sizes vary from 100 to 130.

Figure 16A:
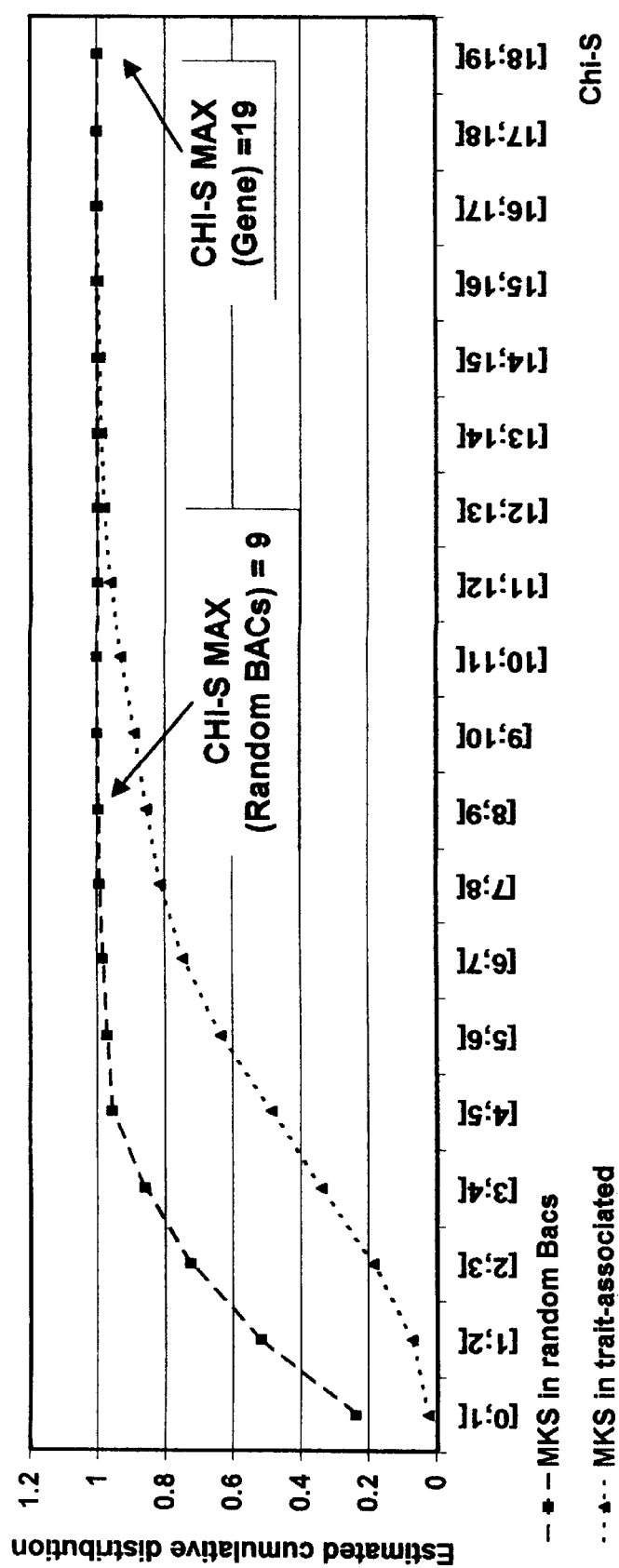
FIG. 16A depicts the estimated distribution function in random BACs and a candidate BAC harboring a first gene associated with prostate cancer.
Figure 16B:
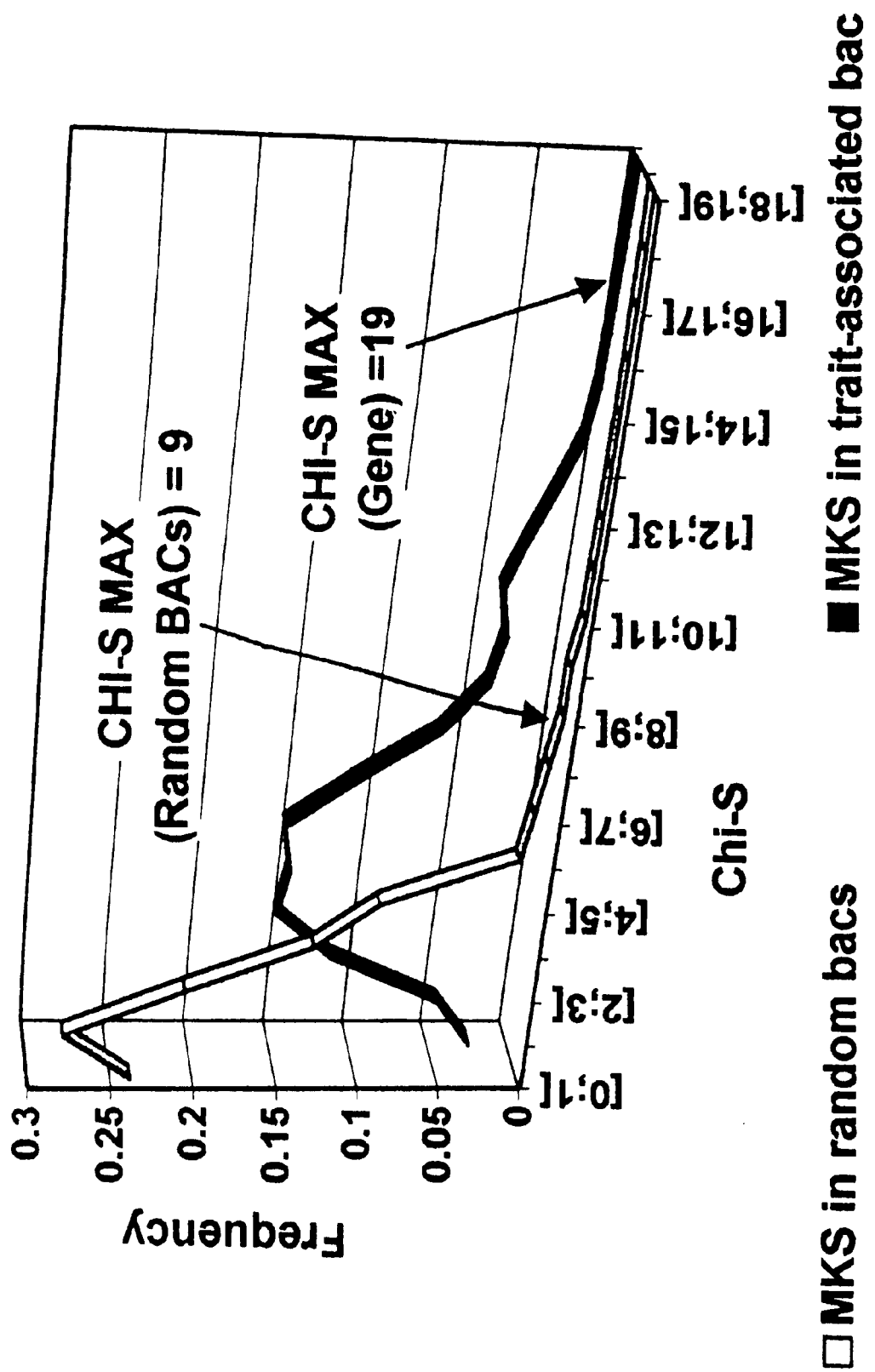
FIG. 16B compares the random region distribution and the candidate region distribution of FIG. 16A.

FIG. 16A depicts the estimated cumulative distribution function in the random BACs and the candidate BAC. FIG. 16B depicts the corresponding estimated density functions in random and candidate bacs (Saporta 1990, supra).

EXAMPLE 21

Comparison of the Random Region Distribution and the Candidate Region Distribution for a First Genomic Region Suspected of Harboring a Gene Associated with Prostate Cancer The validity of the random region distribution was assessed as follows. The group of markers being considered for inclusion in the random region distribution were randomly split into two equal halves. This led to two sets of random markers which will be referred to as BAC(1) and BAC(2). The distributions obtained from the markers in the candidate genomic region and from the entire set of random markers (i.e. BAC(1)+BAC(2)) were compared with the results indicated on the first line of Table 5 below. The distributions obtained from the markers in the candidate genomic region and the BAC(1) group of random markers were compared with the results indicated on the second line of Table 5 below. The distributions from the markers in the candidate genomic region and the BAC(2) group of random markers were compared with the results indicated on the third line of Table 5 below. The distributions from the BAC(1) group of random markers and the BAC(2) group of random markers were compared with the results indicated on fourth line of Table 5 below. As shown in lines 1–3 of Table 5, the distributions of the markers in the candidate genomic region and the various groups of random markers were significantly different, indicating that the candidate genomic region does in fact harbor a gene associated with prostate cancer. In contrast, the distributions of the markers in the BAC(1) and BAC(2) random genomic regions were not significantly different, indicating that these markers were in fact appropriate for inclusion in the random region distribution.

TABLE 5

| | WILCOXON TEST | | | | | SMIRNOV TEST | | | |
|---|---|---|---|---|---|---|---|---|---|
| TEST | SR* | SRE** | IzI | chi-S (Z) 1df | Prob > z | Dmax | chi-S (Dmax) | t | Prob > t |
| BAC vs GENE1 | 250055 | 814330 | 18.93 | 358 | 7.68E − 80 | 0.56 | 2.75 | 8.45 | <0.0001 |
| BAC(1) vs GENE1 | 122423 | 2E + 07 | 13.28 | 176 | 2.62E − 40 | 0.54 | 3.53 | 5.91 | <0.0001 |
| BAC(2) vs GENE1 | 113232 | 2E + 07 | 13.72 | 188 | 8.69E − 43 | 0.59 | 2.75 | 6.39 | <0.0001 |
| BAC(1) vs BAC(2) | 14729 | 14460 | 0.5 | 0.25 | 6.17E − 01 | 0.09 | 2.94 | 0.71 | 6.95E − 01 |

*SR: Sum of the ranks of Chi-S values
**SRE: Sum of the ranks of Chi-S values expected if the candidate region did not harbor a gene associated with trait Using the Wilcoxon method outlined above, the sum of the ranks of the chi-squared values was 250055. Under the null hypothesis, the sum of the ranks of the chi-squared values would be expected to be 814430. Accordingly, the observed z value was −19. This z-value is associated with a p-value less than $10^{-4}$. Thus, the candidate region distribution and the random region distribution are significantly different. Accordingly, there is a very high probability that the candidate genomic region harbors a gene associated with prostate cancer.

A similar result was observed using the Kolmogorov-Smirnov method. The Dmax obtained was 0.56 for a chi-square value of 2.75. This result is again highly significant probability less than $10^{-4}$).

The $F_1^*(x)$ and the $F_2^*(x)$ cumulative distribution functions were calculated for the random region distribution and the candidate region distribution as described above. The results are shown in FIG. 16A. As shown in FIG. 16A, the candidate region distribution was significantly different from the random region distribution. As shown in FIG. 16A, the curve from the candidate BAC is always inferior to the curve from the random BACs. This type of difference is expected if a gene associated with the trait is present in the candidate BAC such that the chi-squared values in the candidate BAC are greater. On FIG. 16B, the curve for the trait associated BAC is shifted to the right.

EXAMPLE 22

Construction of the Random Region Distribution and the Candidate Region Distribution for a Second Genomic Region Suspected of Harboring a Gene Associated with Prostate Cancer An analysis similar to that performed in Examples 20 and 21 was performed for a second genomic region suspected of harboring a gene associated with prostate cancer. However, in this case two different groups of markers in the candidate genomic region were used in the analyses. The first group included all the markers available in the candidate region (Table 6, line 1). The second group included only markers that were not in complete linkage disequilibrium with one another. (Table 6, line 2)

TABLE 6

| REGION | # of bacs | # of markers | # of 3 ms combinations | sample size (# of cases vs of controls) |
|---|---|---|---|---|
| BAC containing the Gene 21 | 1 | 9 (all mks not in complete linkage disequilibrium) | 84 | [90.250] vs [100.130] |
| BAC containing the Gene 22 | 1 | 26 (all mks in the Bac) | 2600 | [90.250] vs [100.130] |
| Random BACs | 30 | 116 | 240 | [180.350] vs [100.130] |

Figure 17A:
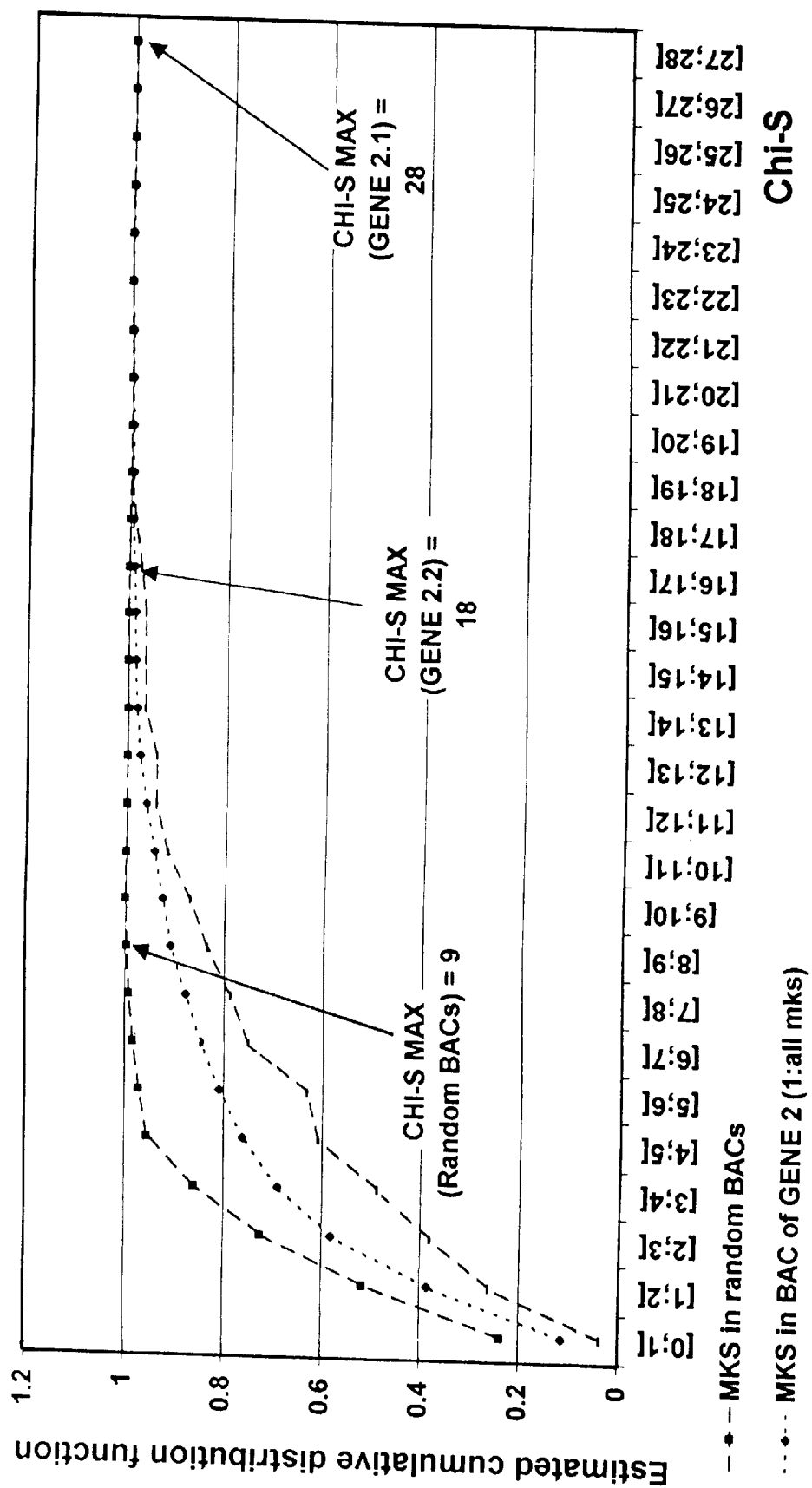
FIG. 17A depicts the estimated distribution function in random BACs and a candidate BAC harboring a second gene associated with prostate cancer.

FIG. 17A depicts the estimated cumulative distribution function in the random BACs and the candidate BAC.

EXAMPLE 23

Comparison of the Random Region Distribution and the Candidate Region Distribution for a Second Genomic Region Suspected of Harboring a Gene Associated with Prostate Cancer The following distributions were compared to one another. The distribution obtained with all markers from the candidate region (gene 2.1) was compared to the distribution from the random genomic regions (Table 7, line 1). The same distribution from the candidate region was compared with the distribution from a first random half, BAC(1) of the markers from the random genomic regions (Table 7, line 2). The same distribution of markers from candidate region was compared with the distribution from a second random half BAC(2) of the markers from the random genomic regions (Table 7, line 3). Each of these approaches indicated that the candidate genomic region harbored a gene associated with prostate cancer.

The distribution obtained from the second group of markers (see Example 22) from the candidate region (gene 2.2) was compared to the distribution from the random markers (Table 7, line 4). The distribution obtained from the second group of markers from the candidate region was compared to the distribution from a first random half of markers (BAC(1)) from the random genomic regions (Table 7, line 5). The distribution obtained from the second group of markers from the candidate region was compared to the distribution from a second random half of markers (BAC(2)) from the random genomic regions (Table 7, line 6). All three approaches indicated that the candidate genomic region is very likely to harbor a gene associated with prostate cancer.

In contrast, the distributions of the markers in the BAC(1) and BAC(2) random genomic regions were not significantly different, indicating that these markers were in fact appropriate for inclusion in the random distribution.

TABLE 7

| | WILCOXON TEST | | | | | SMIRNOV TEST | | | |
|---|---|---|---|---|---|---|---|---|---|
| TEST | SR* | SRE** | IzI | chi-S (Z) 1df | Prob > z | Dmax | chi-S (Dmax) | t | Prob > t |
| BAC vs GENE2.1 | 260653 | 340920 | 6.6 | 43 | 5.47E − 11 | 0.21 | 4.44 | 3.09 | 2.00E − 04 |
| BAC(1) vs GENE2.1 | 125400 | 353700 | 4.5 | 20 | 7.74E − 06 | 0.20 | 4.44 | 2.15 | 2.00E − 04 |
| BAC(2) vs GENE2.1 | 121053 | 4E + 08 | 5.02 | 25 | 5.73E − 07 | 0.21 | 4.41 | 2.34 | 1.00E − 04 |
| BAC vs GENE2.2 | 18667 | 39000 | 6.8 | 46 | 1.18E − 11 | 0.41 | 4.44 | 3.23 | 1.00E − 04 |
| BAC(1) vs GENE2.2 | 81083 | 8610 | 5.96 | 35 | 3.30E − 09 | 0.40 | 4.44 | 2.8 | 1.00E − 04 |
| BAC(2) vs GENE2.2 | 11154 | 8610 | 6.12 | 38 | 7.07E − 10 | 0.20 | 4.41 | 2.93 | 1.00E − 04 |
| BAC(1) vs BAC(2) | 14729 | 14460 | 0.5 | 0.25 | 6.17E − 01 | 0.09 | 2.84 | 0.71 | 6.95E − 01 |

*SR: Sum of the ranks of Chi-S values
**SRE: Sum of the ranks of Chi-S values expected if the candidate region did not harbor a gene associated with trait It is worth noting that the p-values obtained using the second group of markers in the candidate region tend to be more significant than the ones obtained using all markers in the candidate region, which encompasses some markers which are strongly linked to one another. It is also wo noting that these results were obtained with 9 markers having an average intermarker spacing of 40 kb. This is also shown in FIG. 17A and 17B, which show a greater difference between the distribution from markers in the candidate region and the random region distribution when the distribution of markers in the candidate region is generated using only markers that are not in complete linkage disequilibrium.

Figure 17B:
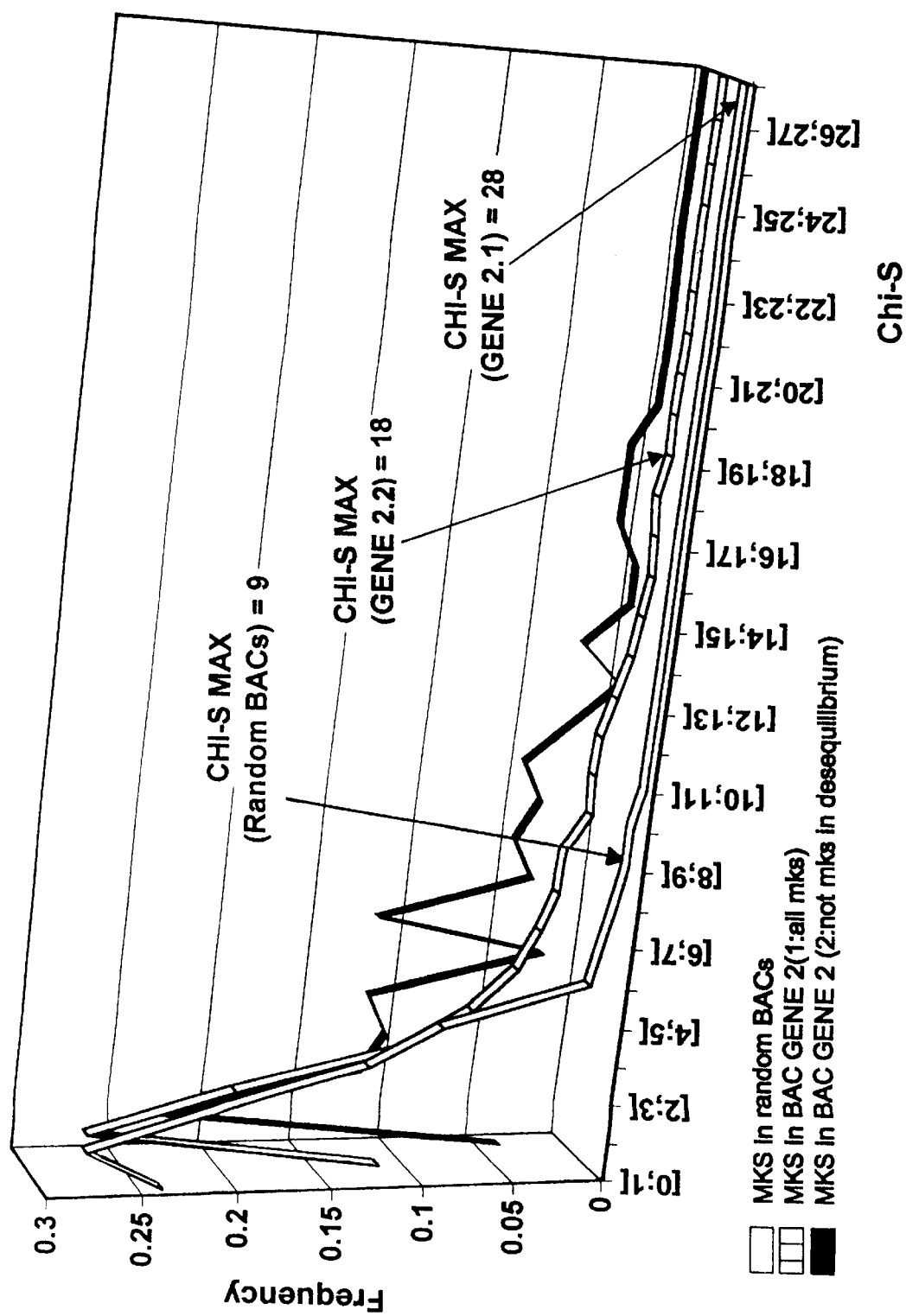
FIG. 17B compares the random region distribution and the candidate region distribution of FIG. 17A.

FIG. 17B shows a comparison of these distributions.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All references cited in this application are incorporated herein by reference in their entirety.

SEQUENCE LISTING FREE TEXT

The following free text appears in the accompanying Sequence Listing:

microsequencing oligo
potential microsequencing oligo
polymorphic base
allele
upstream amplification primer
downstream amplification primer
extracted from sequence

What is claimed is:

1. A method of confirming that a candidate genomic region harbors a gene associated with a detectable trait comprising the steps of:

constructing a candidate region distribution of test values using a plurality of first biallelic markers in a candidate genomic region suspected of harboring said gene associated with said detectable trait, said candidate region distribution of test values being indicative of the difference in the frequencies of said plurality of first biallelic markers in said candidate region in individuals who possess said detectable trait and control individuals who do not possess said detectable trait;

constructing a random region distribution of test values using a plurality of second biallelic markers in random genomic regions which are not suspected of harboring said gene associated with said detectable trait, said random region distribution of test values being indicative of the difference in the frequencies of said plurality of second biallelic markers in said random genomic regions in individuals who possess said detectable trait and control individuals who do not possess said detectable trait; and determining whether said candidate region distribution of test values and said random region distribution of test values are significantly different from one another, wherein a significant difference indicates that said candidate genomic region harbors a gene associated with said detectable trait.

2. The method of claim 1, wherein said step of constructing a candidate region distribution of test values comprises performing a haplotype analysis on each possible combination of biallelic markers in each group in a series of groups of first biallelic markers in said candidate region, calculating test values for each possible combination, and including the test value for the haplotype which has the greatest association with said trait in said candidate region distribution of test values for each group in said series of groups of first biallelic markers in said candidate genomic region and wherein said step of constructing a random region distribution of test values comprises performing a haplotype analysis on each possible combination of biallelic markers in each group in a series of groups of second biallelic markers in said random genomic regions, calculating test values for each possible combination, and including the test value for the haplotype which has the greatest association with said trait in said random region distribution of test values for each group in said series of groups of second biallelic markers in said random genomic regions.

3. The method of claim 2, wherein said steps of performing a haplotype analysis on each possible combination of biallelic markers in each group in said series of groups of first biallelic markers in said candidate genomic region and calculating said test values for each combination comprises the steps of:

calculating the frequencies for each combination of biallelic markers in each group in said series of groups of first biallelic markers in said candidate genomic region in individuals expressing said detectable trait;

calculating the frequencies for each combination of biallelic markers in each group in said series of groups of first biallelic markers in said candidate genomic region in individuals who do not express said detectable trait; and comparing the haplotype frequencies in individuals who express said trait and individuals who do not express said trait by performing a chi-squared analysis to yield said test values.

4. The method of claim 3, wherein said steps of performing a haplotype analysis on each possible combination of biallelic markers in each group in said series of groups of second biallelic markers in said random genomic regions and calculating said test values for each combination comprises the steps of:

calculating the frequencies for each combination of biallelic markers in each group in said series of groups of second biallelic markers in said random genomic regions in individuals expressing said detectable trait;

calculating the frequencies for each combination of biallelic markers in each group in said series of groups of second biallelic markers in said random genomic regions in individuals in individuals who do not express said detectable trait; and comparing the haplotype frequencies in individuals who express said trait and individuals who do not express said trait by performing a chi-squared analysis to yield said test values.

5. The method of claim 4, wherein said step of comparing said candidate region distribution of test values to said random region distribution of test values comprises performing a Wilcoxon rank test.

6. The method of claim 4, wherein said step of comparing said candidate region distribution of test values to said random region distribution of test values comprises performing a Kolmogorov-Smirnov test.

7. The method of claim 4, said step of comparing said candidate region distribution of test values to said random region distribution of test values comprises performing both a Wilcoxon rank test and a Kolmogorov-Smirnov test.

8. The method of claim 4, wherein each of said groups of markers in said series of groups of first biallelic markers in said candidate genomic region and each of said groups of biallelic markers in said series of groups of second biallelic markers in said random genomic regions comprises 3 biallelic markers.

9. The method of claim 4, wherein each of said groups of biallelic markers in said series of groups of first biallelic markers in said candidate genomic region and each of said groups of biallelic markers in said series of groups of second biallelic markers in said random genomic regions comprises at least 3 biallelic markers.

10. The method of claim 4, wherein said biallelic markers in each of said groups in said series of groups of first biallelic markers in said candidate genomic region have an average intermarker distance selected from the group consisting of one marker every 3 kb, one marker every 5 kb, one marker every 10 kb, one marker every 20 kb, and one marker every 30 kb.

11. The method of claim 10, wherein said biallelic markers in each of said groups in said series of groups of second biallelic markers in said random genomic regions have an average intermarker distance selected from the group consisting of one marker every 3 kb, one marker every 5 kb, one marker every 10 kb, one marker every 20 kb, and one marker every 30 kb.

12. The method of claim 4 further comprising selecting random genomic regions for use in said haplotype analysis which have at least 3 biallelic markers therein.

13. The method of claim 12, further comprising selecting random genomic regions for use in said haplotype analysis in which said second biallelic markers have an average intermarker distance sufficient for conducting a haplotype analysis.

14. The method of claim 13 further comprising selecting random genomic regions for use in said haplotype analysis wherein said at least 3 biallelic markers are in Hardy-Weinberg equilibrium in individuals expressing said detectable trait and control individuals who do not express said detectable trait.

15. The method of claim 14 further comprising selecting random genomic regions for use in said haplotype analysis in which said at least 3 biallelic markers are not in complete linkage disequilibrium to be useful in conducting a haplotype analysis.

16. The method of claim 3 further comprising selecting biallelic markers in said candidate genomic region which are in Hardy-Weinberg equilibrium in individuals expressing said detectable trait and control individuals who do not express said detectable trait for use in said haplotype analysis.

17. The method of claim 16 further comprising determining the total number of markers in said candidate genomic region.

18. The method of claim 4 further comprising the step of verifying that the second biallelic markers in said random genomic regions are appropriate for use in the haplotype analysis by:

randomly dividing said second biallelic markers in said random genomic regions into a first verification group and a second verification group, wherein said first verification group and said second verification group contain a substantially identical number of biallelic markers;

constructing a first verification distribution of test values for the biallelic markers in said first verification group by performing a haplotype analysis on each possible combination of biallelic markers in each group in a series of groups of biallelic markers in said first verification group, calculating test values for each possible combination, and including the test value for the haplotype which has the greatest association with said trait in said first verification distribution of test values for each group in said series of groups of biallelic markers in said first verification group;

constructing a second verification distribution of test values for the biallelic markers in said second verification group by performing a haplotype analysis on each possible combination of biallelic markers in each group in a series of groups of biallelic markers in said second verification group, calculating test values for each possible combination, and including the test value for the haplotype which has the greatest association with said trait in said second verification distribution of test values for each group in said series of groups of biallelic markers in said second verification group; and determining whether said first verification distribution and said second verification distribution are significantly different from one another, wherein said second biallelic markers in said random genomic regions are appropriate for use in the haplotype analysis if said first verification distribution and said second verification distribution are not significantly different from one another.

19. The method of claim 18 wherein said steps of performing a haplotype analysis on each possible combination of biallelic markers in each group in said series of groups of biallelic markers in said first and second verification groups and calculating said test values for each combination comprises the steps of:

calculating the frequencies for each combination of biallelic markers in said first verification group in each group in said series of groups of biallelic markers in individuals expressing said detectable trait;

calculating the frequencies for each combination of biallelic markers in said first verification group in each group in said series of groups of biallelic markers in individuals who do not express said detectable trait;

comparing the haplotype frequencies of said biallelic markers in said first verification group in individuals who express said trait and individuals who do not express said trait by performing a chi-squared analysis to yield said test values;

calculating the frequencies for each combination of biallelic markers in said second verification group in each group in said series of groups of biallelic markers in individuals expressing said detectable trait;

calculating the frequencies for each combination of biallelic markers in said second verification group in each group in said series of groups of biallelic markers in individuals who do not express said detectable trait;

comparing the haplotype frequencies of said biallelic markers in said second verification group in individuals who express said trait and individuals who do not express said trait by performing a chi-squared analysis to yield said test values.

20. The method of claim 19, wherein said step of determining whether said first verification distribution and said second verification distribution are significantly different from one another comprises performing a Wilcoxon rank test on said first and second verification distributions.

21. The method of claim 19, wherein said step of determining whether said first verification distribution and said second verification distribution are significantly different from one another comprises performing a Kolmogorov-Smirnov test on said first and second verification distributions.

22. The method of claim 19, wherein said step of determining whether said first verification distribution and said second verification distribution are significantly different from one another comprises performing a both a Kolmogorov-Smirnov test and a Wilcoxon rank test on said first and second verification distributions.

23. The method of claim 19, wherein each of said groups of biallelic markers in said series of groups of biallelic markers in said first verification group and each of said groups of biallelic markers in said series of groups of biallelic markers in said second verification group contains 3 biallelic markers.

24. The method of claim 19, wherein each of said groups of biallelic markers in said series of groups of biallelic markers in said first verification group and each of said groups of biallelic markers in said series of groups of biallelic markers in said second verification group contains more than 3 biallelic markers.

25. The method of claim 1, wherein said method is performed by a computer.

26. The method of claim 25, wherein said computer provides an output indicative of whether said candidate region distribution of test values and said random region distribution of test values are significantly different.

27. The method of claim 26 further comprising further evaluating said candidate genomic region to identify candidate genes which might be associated with said detectable trait if said output indicates that said candidate region distribution of test values and said random region distribution of test values are significantly different.

28. The method of claim 1 further comprising further evaluating said candidate genomic region to identify candidate genes which might be associated with said detectable trait if said candidate region distribution of test values and said random region distribution of test values are significantly different.

29. The method of claim 4 wherein the frequencies for each combination of biallelic markers in each group in said series of groups of first biallelic markers in said candidate genomic region and the frequencies for each combination of biallelic markers in each group in said series of groups of second biallelic markers in said random genomic regions in individuals expressing said detectable trait are calculated using the Expectation Maximization algorithm; and the frequencies for each combination of biallelic markers in each group in said series of groups of first biallelic markers in said candidate genomic region and the frequencies for each combination of second biallelic markers in each group in said series of groups of second biallelic markers in said random genomic regions in individuals who do not express said detectable trait are calculated using the Expectation Maximization algorithm.

30. A method of determining whether a candidate genomic region harbors a gene associated with a detectable trait comprising determining whether the association of a plurality of biallelic markers located in said candidate genomic region with said detectable trait is significantly different than the association of a plurality of biallelic markers located in a plurality of random genomic regions, wherein the determination of whether the association of said plurality of biallelic markers located in said candidate genomic region with said detectable trait is significantly different than the association of said plurality of biallelic markers located in a plurality of random genomic regions comprises:

constructing a candidate region distribution of test values using said biallelic markers in said candidate genomic region, said candidate region distribution of test values being indicative of the difference in the haplotype frequencies of said biallelic markers in said candidate region in individuals who possess said detectable trait and control individuals who do not possess said detectable trait;

constructing a random region distribution of test values using said biallelic markers in said genomic region said random region distribution of test values being indicative of the difference in the haplotype frequencies of said biallelic markers in said random genomic regions in individuals who possess said detectable trait and control individuals who do not possess said detectable trait; and comparing said candidate region distribution of test values with said random region distribution of test values.

31. The method of claim 30, wherein said step of constructing a candidate region distribution of test values comprises performing a haplotype analysis on each possible combination of biallelic markers in each group in a series of groups of biallelic markers in said candidate region, calculating test values for each possible combination, and including the test value for the haplotype which has the greatest association with said trait in said candidate region distribution of test values for each group in said series of groups of biallelic markers in said candidate genomic region and wherein said step of constructing a random region distribution of test values comprises performing a haplotype analysis on each possible combination of biallelic markers in each group in a series of groups of biallelic markers in said random genomic regions, calculating test values for each possible combination, and including the test value for the haplotype which has the greatest association with said trait in said random region distribution of test values for each group in said series of groups of biallelic markers in said random genomic regions.

32. A computer system for confirming that a candidate genomic region harbors a gene associated with a detectable trait, wherein the computer system comprises instructions that when executed perform the method of:

constructing a candidate region distribution of test values using a plurality of first biallelic markers in a candidate genomic region suspected of harboring said gene associated with said detectable trait, said candidate region distribution of test values being indicative of the difference in the frequencies of said plurality of first biallelic markers in said candidate region in individuals who possess said detectable trait and control individuals who do not possess said detectable trait;

constructing a random region distribution of test values using a plurality of second biallelic markers in random genomic regions, said random region distribution of test values being indicative of the difference in the frequencies of said plurality of second biallelic markers in said random genomic regions in individuals who possess said detectable trait and control individuals who do not possess said detectable trait; and determining whether said candidate region distribution of test values and said random region distribution of test values are significantly different from one another, wherein a significant difference indicates that said candidate genomic region harbors a gene associated with said detectable trait.

33. The computer system of claim 32, wherein said instructions for constructing a candidate region distribution of test values comprise instructions for performing a haplotype analysis on each possible combination of biallelic markers in each group in a series of groups of first biallelic markers in said candidate region, calculating test values for each possible combination, and including the test value for the haplotype which has the greatest association with said trait in said candidate region distribution of test values for each group in said series of groups of first biallelic markers in said candidate genomic region and wherein said instructions for constructing a random region distribution of test values comprise instructions for performing a haplotype analysis on each possible combination of biallelic markers in each group in a series of groups of second biallelic markers in said random genomic regions, calculating test values for each possible combination, and including the test value for the haplotype which has the greatest association with said trait in said random region distribution of test values for each group in said series of groups of second biallelic markers in said random genomic regions.

34. The computer system of claim 33, wherein said instructions for performing a haplotype analysis on each possible combination of biallelic markers in each group in said series of groups of first biallelic markers in said candidate genomic region and calculating said test values for each combination comprise instructions for:

calculating the frequencies for each combination of biallelic markers in each group in said series of groups of first biallelic markers in said candidate genomic region in individuals expressing said detectable trait;

calculating the frequencies for each combination of biallelic markers in each group in said series of groups of second biallelic markers in said candidate genomic region in individuals who do not express said detectable trait; and comparing the haplotype frequencies in individuals who express said trait and individuals who do not express said trait by performing a chi-squared analysis to yield said test values.

35. The computer system of claim 34, wherein said instructions for performing a haplotype analysis on each possible combination of biallelic markers in each group in said series of groups of second biallelic markers in said random genomic regions and calculating said test values for each combination comprise instructions for:

calculating the frequencies for each combination of biallelic markers in each group in said series of groups of second markers in said random genomic regions in individuals expressing said detectable trait;

calculating the frequencies for each combination of biallelic markers in each group in said series of groups of second biallelic markers in said random genomic regions in individuals in individuals who do not express said detectable trait; and comparing the haplotype frequencies in individuals who express said trait and individuals who do not express said trait by performing a chi-squared analysis to yield said test values.

36. The computer system of claim 35, wherein said instructions for comparing said candidate region distribution of test values to said random region distribution of test values comprise instructions for performing a Wilcoxon rank test.

37. The computer system of claim 35, wherein said instructions for comparing said candidate region distribution of test values to said random region distribution of test values comprise instructions for performing a Kolmogorov-Smirnov test.

38. The computer system of claim 35, wherein said instructions for comparing said candidate region distribution of test values to said random region distribution of test values comprise instructions for performing both a Wilcoxon rank test and a Kolmogorov-Smirnov test.

39. A programmed storage device comprising instructions that when executed perform the steps of:

constructing a candidate region distribution of test values using a plurality of first biallelic markers in a candidate genomic region suspected of harboring said gene associated with said detectable trait, said trait-associated distribution of test values being indicative of the difference in the frequencies of said plurality of first biallelic markers in said candidate region in individuals who possess said detectable trait and control individuals who do not possess said detectable trait;

constructing a random region distribution of test values using a plurality of second biallelic markers in random genomic regions, said random region distribution of test values being indicative of the difference in the frequencies of said plurality of second biallelic markers in said random genomic regions in individuals who possess said detectable trait and control individuals who do not possess said detectable trait; and determining whether said candidate region distribution of test values and said random region distribution of test values are significantly different from one another, wherein a significant difference indicates that said candidate genomic region harbors a gene associated with said detectable trait.

40. The programmed storage device of claim 39, wherein said instructions for constructing a candidate distribution of test values comprise instructions for performing a haplotype analysis on each possible combination of biallelic markers in each group in a series of groups of first biallelic markers in said candidate region, calculating test values for each possible combination, and including the test value for the haplotype which has the greatest association with said trait in said candidate region distribution of test values for each group in said series of groups of first biallelic markers in said candidate genomic region and wherein said instructions for constructing a random region distribution of test values comprise instructions for performing a haplotype analysis on each possible combination of biallelic markers in each group in a series of groups of second biallelic markers in said random genomic regions, calculating test values for each possible combination, and including the test value for the haplotype which has the greatest association with said trait in said random region distribution of test values for each group in said series of groups of second biallelic markers in said random genomic regions.

41. The programmed storage device of claim 40, wherein said instructions for performing a haplotype analysis on each possible combination of biallelic markers in each group in said series of groups of first biallelic markers in said candidate genomic region and calculating said test values for each combination comprise instructions for:

calculating the frequencies for each combination of biallelic markers in each group in said series of groups of (first) biallelic markers in said candidate genomic region in individuals expressing said detectable trait;

calculating the frequencies for each combination of biallelic markers in each group in said series of groups of first biallelic markers in said candidate genomic region in individuals who do not express said detectable trait; and comparing the haplotype frequencies in individuals who express said trait and individuals who do not express said trait by performing a chi-squared analysis to yield said test values.

42. The programmed storage device of claim 41, wherein said instructions for performing a haplotype analysis on each possible combination of biallelic markers in each group in said series of groups of second biallelic markers in said random genomic regions and calculating said test values for each combination comprise instructions for:

calculating the frequencies for each combination of biallelic markers in each group in said series of groups of second biallelic markers in said random genomic regions in individuals expressing said detectable trait;

calculating the frequencies for each combination of biallelic markers in each group in said series of groups of second biallelic markers in said random genomic regions in individuals in individuals who do not express said detectable trait; and comparing the haplotype frequencies in individuals who express said trait and individuals who do not express said trait by performing a chi-squared analysis to yield said test values.

43. The programmed storage device of claim 42, wherein said instructions for comparing said candidate region distribution of test values to said random region distribution of test values comprise instructions for performing a Wilcoxon rank test.

44. The programmed storage device of claim 42, wherein said instructions for comparing said candidate region distribution of test values to said random region distribution of test values comprise instructions for performing a Kolmogorov-Smirnov test.

45. The programmed storage device of claim 42, wherein said instructions for comparing said candidate region distribution of test values to said random region distribution of test values comprise instructions for performing both a Wilcoxon rank test and a Kolmogorov-Smirnov test.

46. The programmed storage device of claim 39, wherein said programmed storage device is selected from the group consisting of a hard disk a floppy disk, Random Access Memory, Read Only Memory and Electrically Eraseable Programable Read Only Memory.

* * * * *

SEQUENCE LISTING

```
<160> NUMBER OF SEQ ID NOS: 30

<210> SEQ ID NO 1
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base A
<220> FEATURE:
<221> NAME/KEY: misc_binding
<222> LOCATION: 1..23
<223> OTHER INFORMATION: potential microsequencing oligo 99-344-mis1
<220> FEATURE:
<221> NAME/KEY: misc_binding
<222> LOCATION: 25..43
<223> OTHER INFORMATION: microsequencing oligo 99-344-mis2, complement

<400> SEQUENCE: 1
tgctgccaag gatccatgtc agcatgctcc tctctgagcc ctggtct                47

<210> SEQ ID NO 2
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base T
<220> FEATURE:
<221> NAME/KEY: misc_binding
<222> LOCATION: 5..23
<223> OTHER INFORMATION: microsequencing oligo 99-366-mis1
<220> FEATURE:
<221> NAME/KEY: misc_binding
<222> LOCATION: 25..47
<223> OTHER INFORMATION: potential microsequencing oligo 99-366-mis2,
      complement

<400> SEQUENCE: 2
agggcctggc ttcagggaca gcttaggaaa tgtttgttga gttagtg                 47

<210> SEQ ID NO 3
<211> LENGTH: 47
<212> TYPE: DNA
<213> ORGANISM: Homo sapiens
<220> FEATURE:
<221> NAME/KEY: allele
```

```
<222> LOCATION: 24
<223> OTHER INFORMATION: polymorphic base G
<220> FEATURE:
<221> NAME/KEY: misc_binding
<222> LOCATION: 1..23
<223> OTHER INFORMATION: potential microsequencing oligo 99-359-mis1
<220> FEATURE:
<221> NAME/KEY: misc_binding
<222> LOCATION: 25..43
<223> OTHER INFORMATION: microsequencing oligo 99-359-mis2, complement

<400> SEQUENCE: 3
ctacagagtc atcgcctcca tccggtctca acaaatcctg gcagctc                    47

<210> SEQ ID NO 4
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base G
<220> FEATURE:
<221> NAME/KEY: misc_binding
<222> LOCATION: 1..23
<223> OTHER INFORMATION: potential microsequencing oligo 99-355-mis1
<220> FEATURE:
<221> NAME/KEY: misc_binding
<222> LOCATION: 25..43
<223> OTHER INFORMATION: microsequencing oligo 99-355-mis2, complement

<400> SEQUENCE: 4
ggagtttcgg ggagtttcgg gagggttcct gggaagaagc tcctccc                    47

<210> SEQ ID NO 5
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base C
<220> FEATURE:
<221> NAME/KEY: misc_binding
<222> LOCATION: 5..23
<223> OTHER INFORMATION: microsequencing oligo 99-365-mis1
<220> FEATURE:
<221> NAME/KEY: misc_binding
<222> LOCATION: 25..47
<223> OTHER INFORMATION: potential microsequencing oligo 99-365-mis2,
      complement

<400> SEQUENCE: 5
cctaccaagc aagcagcccc agcctagggt cagacagggt gagcctc                    47

<210> SEQ ID NO 6
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base C
<220> FEATURE:
<221> NAME/KEY: misc_binding
<222> LOCATION: 5..23
<223> OTHER INFORMATION: microsequencing oligo 99-2452-mis1
<220> FEATURE:
<221> NAME/KEY: misc_binding
<222> LOCATION: 25..47
<223> OTHER INFORMATION: potential microsequencing oligo 99-2452-mis2,
      complement
<220> FEATURE:
```

```
<221> NAME/KEY: misc_feature
<222> LOCATION: 1..47
<223> OTHER INFORMATION: extracted from sequence gb:M10065 (3909..3955)

<400> SEQUENCE: 6
tgggcgcgga catggaggac gtgcgcggcc gcctggtgca gtaccgc                    47

<210> SEQ ID NO 7
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base G, A in SEQID1
<220> FEATURE:
<221> NAME/KEY: misc_binding
<222> LOCATION: 1..23
<223> OTHER INFORMATION: potential microsequencing oligo 99-344-mis1
<220> FEATURE:
<221> NAME/KEY: misc_binding
<222> LOCATION: 25..43
<223> OTHER INFORMATION: microsequencing oligo 99-344-mis2, complement

<400> SEQUENCE: 7
tgctgccaag gatccatgtc agcgtgctcc tctctgagcc ctggtct                    47

<210> SEQ ID NO 8
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base C, T in SEQID2
<220> FEATURE:
<221> NAME/KEY: misc_binding
<222> LOCATION: 5..23
<223> OTHER INFORMATION: microsequencing oligo 99-366-mis1
<220> FEATURE:
<221> NAME/KEY: misc_binding
<222> LOCATION: 25..47
<223> OTHER INFORMATION: potential microsequencing oligo 99-366-mis2,
      complement

<400> SEQUENCE: 8
agggcctggc ttcagggaca gctcaggaaa tgtttgttga gttagtg                    47

<210> SEQ ID NO 9
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base A, G in SEQID3
<220> FEATURE:
<221> NAME/KEY: misc_binding
<222> LOCATION: 1..23
<223> OTHER INFORMATION: potential microsequencing oligo 99-359-mis1
<220> FEATURE:
<221> NAME/KEY: misc_binding
<222> LOCATION: 25..43
<223> OTHER INFORMATION: microsequencing oligo 99-359-mis2, complement

<400> SEQUENCE: 9
ctacagagtc atcgcctcca tccagtctca acaaatcctg gcagctc                    47

<210> SEQ ID NO 10
<211> LENGTH: 47
<212> TYPE: DNA
```

```
<213> ORGANISM: Homo sapiens
<220> FEATURE:
<221> NAME/KEY: allele
<222> LOCATION: 24
<223> OTHER INFORMATION: polymorphic base A, G in SEQID4
<220> FEATURE:
<221> NAME/KEY: misc_binding
<222> LOCATION: 1..23
<223> OTHER INFORMATION: potential microsequencing oligo 99-355-mis1
<220> FEATURE:
<221> NAME/KEY: misc_binding
<222> LOCATION: 25..43
<223> OTHER INFORMATION: microsequencing oligo 99-355-mis2, complement

<400> SEQUENCE: 10
ggagtttcgg ggagtttcgg gagagttcct gggaagaagc tcctccc                    47

<210> SEQ ID NO 11
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base T, C in SEQID5
<220> FEATURE:
<221> NAME/KEY: misc_binding
<222> LOCATION: 5..23
<223> OTHER INFORMATION: microsequencing oligo 99-365-mis1
<220> FEATURE:
<221> NAME/KEY: misc_binding
<222> LOCATION: 25..47
<223> OTHER INFORMATION: potential microsequencing oligo 99-365-mis2,
      complement

<400> SEQUENCE: 11
cctaccaagc aagcagcccc agcttagggt cagacagggt gagcctc                    47

<210> SEQ ID NO 12
<211> LENGTH: 47
<212> TYPE: DNA
<213> ORGANISM: Homo sapiens
<220> FEATURE:
<221> NAME/KEY: allele
<222> LOCATION: 24
<223> OTHER INFORMATION: polymorphic base T, C in SEQID6
<220> FEATURE:
<221> NAME/KEY: misc_binding
<222> LOCATION: 5..23
<223> OTHER INFORMATION: microsequencing oligo 99-2452-mis1
<220> FEATURE:
<221> NAME/KEY: misc_binding
<222> LOCATION: 25..47
<223> OTHER INFORMATION: potential microsequencing oligo 99-2452-mis2,
      complement

<400> SEQUENCE: 12
tgggcgcgga catggaggac gtgtgcggcc gcctggtgca gtaccgc                    47

<210> SEQ ID NO 13
<211> LENGTH: 20
<212> TYPE: DNA
<213> ORGANISM: Homo sapiens
<220> FEATURE:
<221> NAME/KEY: primer_bind
<222> LOCATION: 1..20
<223> OTHER INFORMATION: upstream amplification primer for SEQID 1 and
      SEQID 7

<400> SEQUENCE: 13
gctctcatat tcattgggtg                                                  20
```

```
<210> SEQ ID NO 14
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: upstream amplification primer for SEQID 2 and
      SEQID 8

<400> SEQUENCE: 14
tctctcccgt gttaaatg                                                18

<210> SEQ ID NO 15
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: upstream amplification primer for SEQID 3 and
      SEQID 9

<400> SEQUENCE: 15
aatcttcttg ctcctgtc                                                18

<210> SEQ ID NO 16
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: upstream amplification primer for SEQID 4 and
      SEQID 10

<400> SEQUENCE: 16
aggttagggg tgtatttc                                                18

<210> SEQ ID NO 17
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: upstream amplification primer for SEQID 5 and
      SEQID 11

<400> SEQUENCE: 17
agactgtgac cttagacc                                                18

<210> SEQ ID NO 18
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: upstream amplification primer for SEQID 6 and
      SEQID 12
<220> FEATURE:
<221> NAME/KEY: misc_feature
<222> LOCATION: 1..18
<223> OTHER INFORMATION: Extracted from sequence gb:M10065 (3791..3808)

<400> SEQUENCE: 18
gacgagacca tgaaggag                                                18
```

-continued

```
<210> SEQ ID NO 19
<211> LENGTH: 19
<212> TYPE: DNA
<213> ORGANISM: Homo sapiens
<220> FEATURE:
<221> NAME/KEY: primer_bind
<222> LOCATION: 1..19
<223> OTHER INFORMATION: downstream amplification primer for SEQID 1 and
      SEQID 7

<400> SEQUENCE: 19
tggctgcggt tagatgctc                                                      19

<210> SEQ ID NO 20
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: downstream amplification primer for SEQID 2 and
      SEQID 8

<400> SEQUENCE: 20
aggggtaact cttgattg                                                       18

<210> SEQ ID NO 21
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: downstream amplification primer for SEQID 3 and
      SEQID 9

<400> SEQUENCE: 21
accaaggcat agcttctc                                                       18

<210> SEQ ID NO 22
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: downstream amplification primer for SEQID 4 and
      SEQID 10

<400> SEQUENCE: 22
atacagccag ggagatag                                                       18

<210> SEQ ID NO 23
<211> LENGTH: 18
<212> TYPE: DNA
<213> ORGANISM: Homo sapiens
<220> FEATURE:
<221> NAME/KEY: primer_bind
<222> LOCATION: 1..18
<223> OTHER INFORMATION: downstream amplification primer for SEQID 5 and
      SEQID 11

<400> SEQUENCE: 23
aattgctacc cccaattc                                                       18

<210> SEQ ID NO 24
<211> LENGTH: 18
<212> TYPE: DNA
```

```
<213> ORGANISM: Homo sapiens
<220> FEATURE:
<221> NAME/KEY: primer_bind
<222> LOCATION: 1..18
<223> OTHER INFORMATION: downstream amplification primer for SEQID 6 and
      SEQID 12
<220> FEATURE:
<221> NAME/KEY: misc_feature
<222> LOCATION: 1..18
<223> OTHER INFORMATION: Extracted from sequence gb:M10065 (complement
      4378 4395)

<400> SEQUENCE: 24
tcgaaccagc tcttgagg                                                   18

<210> SEQ ID NO 25
<211> LENGTH: 23
<212> TYPE: DNA
<213> ORGANISM: Homo sapiens
<220> FEATURE:
<221> NAME/KEY: misc_binding
<222> LOCATION: 1..23
<223> OTHER INFORMATION: potential microsequencing oligo 99-344.mis1

<400> SEQUENCE: 25
tgctgccaag gatccatgtc agc                                             23

<210> SEQ ID NO 26
<211> LENGTH: 19
<212> TYPE: DNA
<213> ORGANISM: Homo sapiens
<220> FEATURE:
<221> NAME/KEY: misc_binding
<222> LOCATION: 1..19
<223> OTHER INFORMATION: microsequencing oligo 99-366.mis1

<400> SEQUENCE: 26
cctggcttca gggacagct                                                  19

<210> SEQ ID NO 27
<211> LENGTH: 23
<212> TYPE: DNA
<213> ORGANISM: Homo sapiens
<220> FEATURE:
<221> NAME/KEY: misc_binding
<222> LOCATION: 1..23
<223> OTHER INFORMATION: potential microsequencing oligo 99-359.mis1

<400> SEQUENCE: 27
ctacagagtc atcgcctcca tcc                                             23

<210> SEQ ID NO 28
<211> LENGTH: 23
<212> TYPE: DNA
<213> ORGANISM: Homo sapiens
<220> FEATURE:
<221> NAME/KEY: misc_binding
<222> LOCATION: 1..23
<223> OTHER INFORMATION: potential microsequencing oligo 99-355.mis

<400> SEQUENCE: 28
ggagtttcgg ggagtttcgg gag                                             23

<210> SEQ ID NO 29
<211> LENGTH: 19
<212> TYPE: DNA
<213> ORGANISM: Homo sapiens
<220> FEATURE:
<221> NAME/KEY: misc_binding
```

```
-continued

<222> LOCATION: 1..19
<223> OTHER INFORMATION: microsequencing oligo 99-365.mis

<400> SEQUENCE: 29
ccaagcaagc agccccagc                                                    19

<210> SEQ ID NO 30
<211> LENGTH: 19
<212> TYPE: DNA
<213> ORGANISM: Homo sapiens
<220> FEATURE:
<221> NAME/KEY: misc_binding
<222> LOCATION: 1..19
<223> OTHER INFORMATION: microsequencing oligo 99-2452.mis

<400> SEQUENCE: 30
cgcggacatg gaggacgtg                                                    19
```